(12) United States Patent
Tseng et al.

(10) Patent No.: US 11,318,169 B2
(45) Date of Patent: *May 3, 2022

(54) COMPOSITIONS AND METHODS FOR PREVENTING THE PROLIFERATION AND EPITHELIAL-MESENCHYMAL TRANSITION OF EPITHELIAL CELLS

(71) Applicant: TissueTech, Inc., Miami, FL (US)

(72) Inventors: Scheffer Tseng, Pinecrest, FL (US); Ek Kia Tan, Miami, FL (US); Hua He, Miami, FL (US)

(73) Assignee: TISSUETECH, INC., Miami, FL (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/421,191

(22) Filed: May 23, 2019

(65) Prior Publication Data

US 2019/0343890 A1  Nov. 14, 2019

Related U.S. Application Data

(63) Continuation of application No. 15/160,487, filed on May 20, 2016, now Pat. No. 10,342,831.

(60) Provisional application No. 62/164,281, filed on May 20, 2015.

(51) Int. Cl.
| | |
|---|---|
| *A61K 35/50* | (2015.01) |
| *A61K 35/51* | (2015.01) |
| *A61P 27/02* | (2006.01) |
| *A61K 9/00* | (2006.01) |
| *A61K 47/36* | (2006.01) |

(52) U.S. Cl.
CPC ............ *A61K 35/50* (2013.01); *A61K 9/0019* (2013.01); *A61K 35/51* (2013.01); *A61K 47/36* (2013.01); *A61P 27/02* (2018.01); *A61K 2236/10* (2013.01)

(58) Field of Classification Search
None
See application file for complete search history.

(56) References Cited

U.S. PATENT DOCUMENTS

| | | | |
|---|---|---|---|
| 3,598,122 | A | 8/1971 | Zaffaroni et al. |
| 3,598,123 | A | 8/1971 | Zaffaroni et al. |
| 3,710,795 | A | 1/1973 | Higuchi et al. |
| 3,731,683 | A | 5/1973 | Zaffaroni et al. |
| 3,742,951 | A | 7/1973 | Zaffaroni et al. |
| 3,814,097 | A | 6/1974 | Ganderton et al. |
| 3,921,636 | A | 11/1975 | Zaffaroni et al. |
| 3,972,995 | A | 8/1976 | Tsuk et al. |
| 3,993,072 | A | 11/1976 | Zaffaroni et al. |
| 3,993,073 | A | 11/1976 | Zaffaroni et al. |
| 3,996,934 | A | 12/1976 | Zaffaroni et al. |
| 4,031,894 | A | 6/1977 | Urquhart et al. |
| 4,060,084 | A | 11/1977 | Chandrasekaran et al. |
| 4,069,307 | A | 1/1978 | Higuchi et al. |
| 4,077,407 | A | 3/1978 | Theeuwes et al. |
| 4,141,973 | A * | 2/1979 | Balazs ................ C08B 37/0072 514/54 |
| 4,201,211 | A | 5/1980 | Chandrasekaran et al. |
| 4,230,105 | A | 10/1980 | Harwood et al. |
| 4,292,299 | A | 9/1981 | Suzuki et al. |
| 4,292,303 | A | 9/1981 | Keith et al. |
| 4,305,502 | A | 12/1981 | Gregory et al. |
| 4,327,725 | A | 5/1982 | Cortese et al. |
| 4,347,841 | A | 9/1982 | Benyo et al. |
| 4,476,116 | A | 10/1984 | Anik |
| 4,624,848 | A | 11/1986 | Lee |
| 4,871,549 | A | 10/1989 | Ueda et al. |
| 4,968,509 | A | 11/1990 | Radebaugh et al. |
| 5,002,071 | A | 3/1991 | Harrell |
| 5,011,692 | A | 4/1991 | Fujioka et al. |
| 5,017,381 | A | 5/1991 | Maruyama et al. |
| 5,052,558 | A | 10/1991 | Carter |
| 5,093,487 | A | 3/1992 | Brown et al. |
| 5,116,817 | A | 5/1992 | Anik |
| 5,192,744 | A | 3/1993 | Bouck et al. |
| 5,229,135 | A | 7/1993 | Philippon et al. |
| 5,260,068 | A | 11/1993 | Chen |
| 5,260,069 | A | 11/1993 | Chen |
| 5,336,168 | A | 8/1994 | Sibalis |
| 5,437,287 | A | 8/1995 | Phillips et al. |
| 5,456,923 | A | 10/1995 | Nakamichi et al. |
| 5,461,140 | A | 10/1995 | Heller et al. |
| 5,508,040 | A | 4/1996 | Chen |
| 5,516,527 | A | 5/1996 | Curatolo |
| 5,554,593 | A | 9/1996 | Nakaya et al. |
| 5,567,441 | A | 10/1996 | Chen |
| 5,622,721 | A | 4/1997 | Dansereau et al. |
| 5,665,378 | A | 9/1997 | Davis et al. |
| 5,686,105 | A | 11/1997 | Kelm et al. |

(Continued)

FOREIGN PATENT DOCUMENTS

| | | |
|---|---|---|
| CN | 1720055 A | 1/2006 |
| CN | 1903073 A | 1/2007 |

(Continued)

OTHER PUBLICATIONS

Edmund, Mod Probl Ophthalmol, 1974, 12:370-377. (Year: 1974).*

(Continued)

*Primary Examiner* — Allison M Fox
(74) *Attorney, Agent, or Firm* — Wilson Sonsini Goodrich & Rosati

(57) ABSTRACT

Compositions and preparations of fetal support tissue that prevent or reduce the proliferation and epithelial-mesenchymal transition (EMT) of epithelial cells, wherein the epithelial cells may be human epithelial cells and the human epithelial cells may be conjunctival, retinal, corneal, limbal, or renal epithelial cells. Methods of preventing or reducing the proliferation, cell migration, and EMT of epithelial cells in an individual in need thereof, wherein the epithelial cells may be human epithelial cells and the human epithelial cells may be conjunctival, retinal, corneal, limbal, or renal epithelial cells. Methods of preventing or treating proliferative vitreoretinopathy in an individual in need thereof.

9 Claims, 31 Drawing Sheets

(56) References Cited

U.S. PATENT DOCUMENTS

| | | | |
|---|---|---|---|
| 5,700,410 | A | 12/1997 | Nakamichi et al. |
| 5,837,280 | A | 11/1998 | Kenealy et al. |
| 5,837,284 | A | 11/1998 | Mehta et al. |
| 5,840,329 | A | 11/1998 | Bai |
| 5,869,090 | A | 2/1999 | Rosenbaum |
| 5,932,545 | A | 8/1999 | Henkin et al. |
| 5,977,175 | A | 11/1999 | Lin |
| 6,046,160 | A | 4/2000 | Obi-Tabot |
| 6,152,142 | A | 11/2000 | Tseng |
| 6,203,755 | B1 | 3/2001 | Odland |
| 6,326,019 | B1 | 12/2001 | Tseng |
| 6,391,452 | B1 | 5/2002 | Antonsen et al. |
| 6,465,014 | B1 | 10/2002 | Moroni et al. |
| 6,521,179 | B1 | 2/2003 | Girardot et al. |
| 6,573,249 | B2 | 6/2003 | Lezdey et al. |
| 6,632,648 | B1 | 10/2003 | Kampinga et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 8,071,135 | B2 | 12/2011 | Liu et al. |
| 8,093,365 | B2 | 1/2012 | Wisniewski et al. |
| 8,105,634 | B2 | 1/2012 | Liu et al. |
| 8,153,162 | B2 | 4/2012 | Tseng et al. |
| 8,182,840 | B2 | 5/2012 | Tseng et al. |
| 8,182,841 | B2 | 5/2012 | Tseng et al. |
| 8,187,639 | B2 | 5/2012 | Tseng et al. |
| 8,323,701 | B2 | 12/2012 | Daniel et al. |
| 8,372,437 | B2 | 2/2013 | Daniel |
| 8,420,126 | B2 | 4/2013 | Tseng et al. |
| 8,440,235 | B2 | 5/2013 | Tseng et al. |
| 8,455,009 | B2 | 6/2013 | Tseng et al. |
| 8,460,714 | B2 | 6/2013 | Tseng et al. |
| 8,840,665 | B2 | 9/2014 | Young et al. |
| 8,932,805 | B1 | 1/2015 | Brahm |
| 8,961,617 | B2 | 2/2015 | Young |
| 8,980,630 | B2 | 3/2015 | Woodbury et al. |
| 9,161,954 | B2 | 10/2015 | Tseng et al. |
| 9,161,955 | B2 | 10/2015 | Tseng et al. |
| 9,161,956 | B2 | 10/2015 | Tseng et al. |
| 9,162,011 | B2 | 10/2015 | Stilwell et al. |
| 9,175,066 | B2 | 11/2015 | Tseng et al. |
| 9,180,145 | B2 | 11/2015 | Brown et al. |
| 9,198,939 | B2 | 12/2015 | Tseng et al. |
| 9,498,327 | B1 | 11/2016 | Brahm |
| 9,662,355 | B2 | 5/2017 | Koob et al. |
| 9,682,160 | B2 | 6/2017 | Tseng et al. |
| 9,694,109 | B1 | 7/2017 | Brahm |
| 9,724,370 | B2 | 8/2017 | Tseng et al. |
| 9,750,771 | B2 | 9/2017 | Tseng et al. |
| 9,750,772 | B2 | 9/2017 | Tseng et al. |
| 9,795,639 | B1 | 10/2017 | Brahm |
| 9,801,975 | B2 | 10/2017 | Stilwell et al. |
| 9,801,976 | B2 | 10/2017 | Stilwell et al. |
| 9,803,176 | B2 | 10/2017 | Patel et al. |
| 9,814,746 | B2 | 11/2017 | Werber et al. |
| 9,821,013 | B2 | 11/2017 | Mcfetridge et al. |
| 9,827,293 | B2 | 11/2017 | Koob et al. |
| 9,913,466 | B2 | 3/2018 | Chang et al. |
| 9,919,078 | B1 | 3/2018 | Brahm |
| 9,920,301 | B2 | 3/2018 | Taghizadeh |
| 9,931,423 | B2 | 4/2018 | Tseng et al. |
| 9,944,900 | B2 | 4/2018 | Gage et al. |
| 9,956,248 | B2 | 5/2018 | Tom et al. |
| 9,956,252 | B2 | 5/2018 | Tseng et al. |
| 9,993,506 | B1 | 6/2018 | Brahm |
| 10,006,003 | B2 | 6/2018 | Spencer et al. |
| 10,029,030 | B2 | 7/2018 | Koob et al. |
| 10,039,793 | B2 | 8/2018 | Brown et al. |
| 10,040,821 | B2 | 8/2018 | Tseng et al. |
| 10,253,065 | B2 | 4/2019 | Tseng et al. |
| 10,272,119 | B2 | 4/2019 | Tseng et al. |
| 10,314,688 | B2 | 6/2019 | Shepard et al. |
| 10,342,831 | B2 | 7/2019 | Tseng et al. |
| 10,568,914 | B1 | 2/2020 | Brahm |
| 10,646,519 | B2 | 5/2020 | Tom et al. |
| 10,688,220 | B2 | 6/2020 | Hopkinson et al. |
| 2003/0064093 | A1 | 4/2003 | Jordan |
| 2003/0180181 | A1 | 9/2003 | Greib et al. |
| 2003/0187515 | A1 | 10/2003 | Hariri et al. |
| 2004/0043026 | A1 | 3/2004 | Tuan et al. |
| 2004/0057938 | A1 | 3/2004 | Ghinelli |
| 2004/0059430 | A1 | 3/2004 | Kim et al. |
| 2004/0126323 | A1 | 7/2004 | Shevchuk et al. |
| 2005/0064391 | A1 | 3/2005 | Segal et al. |
| 2006/0078993 | A1 | 4/2006 | Phan et al. |
| 2008/0050814 | A1 | 2/2008 | Allickson |
| 2008/0102135 | A1 | 5/2008 | Ollivier |
| 2008/0131522 | A1 | 6/2008 | Liu et al. |
| 2008/0193554 | A1 | 8/2008 | Dua et al. |
| 2011/0212158 | A1 | 9/2011 | Tom et al. |
| 2011/0311491 | A1 | 12/2011 | Edinger et al. |
| 2012/0010708 | A1 | 1/2012 | Young et al. |
| 2012/0010727 | A1 | 1/2012 | Young et al. |
| 2012/0020933 | A1 | 1/2012 | Young et al. |
| 2012/0035744 | A1 | 2/2012 | Young et al. |
| 2012/0141595 | A1 | 6/2012 | Tseng et al. |
| 2012/0263731 | A1 | 10/2012 | Fraunhofer et al. |
| 2012/0294910 | A1 | 11/2012 | Daniel et al. |
| 2013/0156863 | A1 | 6/2013 | Tseng et al. |
| 2013/0197665 | A1 | 8/2013 | Daniel et al. |
| 2013/0209524 | A1 | 8/2013 | Young |
| 2013/0211502 | A1 | 8/2013 | Young |
| 2013/0211504 | A1 | 8/2013 | Young |
| 2013/0211511 | A1 | 8/2013 | Young |
| 2013/0236506 | A1 | 9/2013 | Young |
| 2013/0289724 | A1 | 10/2013 | Young |
| 2013/0344162 | A1 | 12/2013 | Morse et al. |
| 2013/0344163 | A1 | 12/2013 | Tseng et al. |
| 2014/0050788 | A1 | 2/2014 | Daniel et al. |
| 2014/0052247 | A1 | 2/2014 | Daniel et al. |
| 2014/0052274 | A1 | 2/2014 | Koob et al. |
| 2014/0106447 | A1 | 4/2014 | Brown et al. |
| 2014/0255496 | A1 | 9/2014 | Daniel et al. |
| 2014/0271776 | A1 | 9/2014 | Vines et al. |
| 2014/0302162 | A1 | 10/2014 | Morse et al. |
| 2015/0017255 | A1 | 1/2015 | Koob et al. |
| 2015/0086634 | A1 | 3/2015 | Koob et al. |
| 2015/0216912 | A1 | 8/2015 | Koob |
| 2015/0250829 | A1 | 9/2015 | Daniel et al. |
| 2015/0320906 | A1 | 11/2015 | Broussard et al. |
| 2015/0328264 | A1 | 11/2015 | Lucey et al. |
| 2015/0335686 | A1 | 11/2015 | Spencer et al. |
| 2016/0067287 | A1 | 3/2016 | Mcqueen et al. |
| 2016/0082152 | A1 | 3/2016 | Brahm |
| 2016/0095931 | A1 | 4/2016 | Tseng et al. |
| 2016/0106785 | A1 | 4/2016 | Tseng et al. |
| 2016/0184368 | A1 | 6/2016 | Tseng et al. |
| 2016/0303171 | A1 | 10/2016 | Tseng et al. |
| 2016/0324902 | A1 | 11/2016 | Tseng et al. |
| 2016/0346332 | A1 | 12/2016 | Spencer et al. |
| 2017/0027993 | A1 | 2/2017 | Ichim |
| 2017/0136071 | A1 | 5/2017 | Danilkovitch et al. |
| 2017/0203004 | A1 | 7/2017 | Murphy et al. |
| 2017/0252380 | A1 | 9/2017 | Cox, Jr. et al. |
| 2017/0260500 | A1 | 9/2017 | Goodman et al. |
| 2017/0368105 | A1 | 12/2017 | Sinclair et al. |
| 2018/0008649 | A1 | 1/2018 | Aberman et al. |
| 2018/0017577 | A1 | 1/2018 | Franco |
| 2018/0055622 | A1 | 3/2018 | Tokish et al. |
| 2018/0059109 | A1 | 3/2018 | Hsuan et al. |
| 2018/0110900 | A1 | 4/2018 | Korenfeld |
| 2018/0112184 | A1 | 4/2018 | Kim et al. |
| 2018/0117121 | A1 | 5/2018 | Koob et al. |
| 2018/0119093 | A1 | 5/2018 | Kukharchuk et al. |
| 2018/0126036 | A1 | 5/2018 | Early |
| 2018/0127721 | A1 | 5/2018 | Phan |
| 2018/0132908 | A1 | 5/2018 | Brahm et al. |
| 2018/0140641 | A1 | 5/2018 | Harrell |
| 2018/0163177 | A1 | 6/2018 | Lo et al. |
| 2018/0177716 | A1 | 6/2018 | Noh et al. |
| 2018/0177989 | A1 | 6/2018 | Prentice |
| 2018/0193387 | A1 | 7/2018 | Tseng et al. |
| 2018/0221418 | A1 | 8/2018 | Daniel et al. |

(56) References Cited

U.S. PATENT DOCUMENTS

| | | | |
|---|---|---|---|
| 2018/0264049 | A1 | 9/2018 | Wagner et al. |
| 2018/0271914 | A1 | 9/2018 | Steed et al. |
| 2018/0271917 | A1 | 9/2018 | Fu |
| 2018/0338998 | A1 | 11/2018 | Petrucci |
| 2018/0344777 | A1 | 12/2018 | Harris et al. |
| 2018/0346874 | A1 | 12/2018 | Harris et al. |
| 2018/0362920 | A1 | 12/2018 | Guo |
| 2018/0362923 | A1 | 12/2018 | Guo |
| 2018/0362932 | A1 | 12/2018 | Guo |
| 2019/0070335 | A1 | 3/2019 | Karagianis |
| 2019/0127702 | A1 | 5/2019 | Kerkis et al. |
| 2019/0134100 | A1 | 5/2019 | Cao et al. |
| 2019/0141987 | A1 | 5/2019 | Patel et al. |
| 2019/0169231 | A1 | 6/2019 | Tseng et al. |
| 2019/0177684 | A1 | 6/2019 | Ha et al. |
| 2020/0069739 | A1 | 3/2020 | Tom et al. |
| 2020/0077987 | A1 | 3/2020 | Harrell |
| 2020/0155613 | A1 | 5/2020 | Beaudry et al. |

FOREIGN PATENT DOCUMENTS

| | | | |
|---|---|---|---|
| EP | 1604695 | A1 | 12/2005 |
| JP | 74043153 | B | 11/1974 |
| JP | H01256967 | A | 10/1989 |
| KR | 20010098716 | A | 11/2001 |
| WO | WO-9837903 | A1 | 9/1998 |
| WO | WO-03077794 | A2 | 9/2003 |
| WO | WO-03097809 | A1 | 11/2003 |
| WO | WO-2004026244 | A2 | 4/2004 |
| WO | WO-2004060388 | A1 | 7/2004 |
| WO | WO-2005060988 | A1 | 7/2005 |
| WO | WO-2006094247 | A2 | 9/2006 |
| WO | WO-2007038686 | A2 | 4/2007 |
| WO | WO-2007071048 | A1 | 6/2007 |
| WO | WO-2010124296 | A2 | 10/2010 |
| WO | WO-2011031489 | A2 | 3/2011 |
| WO | WO-2012149486 | A1 | 11/2012 |
| WO | WO-2012170905 | A1 | 12/2012 |
| WO | WO-2014011813 | A1 | 1/2014 |
| WO | WO-2015052714 | A1 | 4/2015 |
| WO | WO-2016187555 | A1 | 11/2016 |

OTHER PUBLICATIONS

Lozano-Lopez et al, Retinal Cases & Brief Reports, 2012, 6(2):156-158/ (Year: 2012).*
Riau et al, Biomaterials, 2010, 31:216-225. (Year: 2010).*
Ahmed et al. Expression and localization of alphavbeta6 integrin in extraplacental fetal membranes: possible role in human parturition. Mol Hum Reprod 10(3):173-179 (2004).
Allred et al. A novel ELISA for measuring CD36 protein in human adipose tissue. J Lipid Res 2(2):408-415 (2011).
Bae et al. Characterization of the Promoter Region of the Human Transforming Growth Factor-β Type II Receptor Gene. J. Biol. Chem. 270(49):29460-29468 (1995).
Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).
Border et al. Transforming Growth Factor-β in Disease: The Dark Side of Tissue Repair. J. Clin. Invest. 90:1-7 (1992).
Chen et al. Amniotic Membrane Transplantation for Severe Neurotrophic Corneal Ulcers. Br. J. Ophthalmol. 84:826-833 (2000).
Chen et al. Functions of hyaluronan in wound repair. Wound Rep Reg 7:79-89 (1999).
Chen et al. Recombinant Adenovirus Coexpressing Covalent Peptide/MHC Class II Complex and B7-1: In Vitro and In Vivo Activation of Myelin Basic Protein-Specific T Cells. J. Immunol. 167:1297-1305 (2001).
Colon et al. Transfer of Inter-α-inhibitor Heavy Chains to Hyaluronan by Surface-linked Hyaluronan-TSG-6 Complexes. J. Biol. Chem. 2009. 284:2320-2331.
Derynk et al. TGF-β receptor signaling. Biochem. Biophys. Acta. 1333:F105-F150 (1997).
Dogru et al. Corneal sensitivity and ocular surface changes following preserved amniotic membrane transplantation for non-healing corneal ulcers. Eye 17:139-148 (2003).
English Translation of JP74043153B (App. S45-107284) (9 pgs.) (Pub. Nov. 19, 1974).
Ericsson et al. Chapter 17: Protein extraction from solid tissue. Methods Mol Biol. 675:307-312 (2011).
Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).
Fortunato et al. Interleukin-10 inhibition of interleukin-6 in human amniochorionic membrane: Transcriptional regulation. Am. J. Obstet. Gynecol. 175:1057-1065 (1996).
Fortunato et al. The effect of transforming growth factor and interleukin-10 on interleukin-8 release by human amniochorion may regulate histologic chorioamnionitis. Am. J. Obstet. Gynecol. 179(3):794-799 (1998).
Fries et al. Inter-alpha-inhibitor, hyaluronan and inflammation. Acta Biochim Polonica 50(3):735-742 (2003).
Gabbiani. The myofibroblast in wound healing and fibrocontractive diseases. J. Pathol. 200:500-503 (2003).
Grande. Role of Transforming Growth Factor-β in Tissue Injury and Repair. Proc. Soc. Exp. Biol. Med. 214:27-40 (1997).
Guo. Carbopol® Polymers for Pharmaceutical Drug Delivery Applications. Drug Delivery Technology 3(6):1-4 (2003).
Hales et al. TGF-β-1 induces lens cells to accumulate α-smooth muscle actin, a marker for subcapsular cataracts. Curr. Eye Res. 13:885-890 (1994).
Hall et al. Liquid Extraction Surface Analysis Mass Spectrometry Method for Identifying the Presence and Severity of Nonalcoholic Fatty Liver Disease. Anal. Chem. 89(9):5161-5170 (2017).
Hanada et al. Regulation of cytokine signaling and inflammation. Cytokine & Growth Factor Reviews 13(4-5):413-421 (2002).
Hao et al. Identification of Antiangiogenic and Antiinflammatory Proteins in Human Amniotic Membrane. Cornea 19(3):348-352 (2000).
Hatano et al. Transplantation of amniotic membrane and limbal autograft in the treatment of recurrent pterygium. Clinical Ophthalmology 50(6):1101-1104 (1996) (English Abstract).
He et al. A simplified system for generating recombinant adenoviruses. PNAS USA 95:2509-2514 (1998).
He et al. Biochemical Characterization and Function of Complexes formed by Hyaluronan and the Heavy Chains of Inter-α-inhibitor (HC-HA) Purified from Extracts of Human Amniotic Membrane. J Biol Chem 284(30):20136-20146 (Jul. 24, 2009).
He et al. Immobilized heavy chain-hyaluronic acid polarizes lipopolysaccharide-activated macrophages toward M2 phenotype. J Biol Chem 288(36):25792-25803 (2013).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) May 1-May 5, 2016 (Washington State Convention Center, Seattle, Washington) Abstract No. 5384-B005 (2 pgs).
He et al. Role of Hyaluronan, Inter-Alpha-Trypsin Inhibitor, and TSG-6 Complex in Amniotic Membrane in Inhibiting TFG-Beta Transcription. ARVO Annual Meeting Abstract. Investigative Ophthalmology & Visual Science 47:599 (May 2006).
He et al. Suppression of activation and induction of apoptosis in RAW264.7 cells by amniotic membrane extract. Invest Ophthalmol. Vis. Sci. 49:4468-4475 (2008).
Hilmy et al. Physical and chemical properties of freeze-dried amnio-chorion membranes sterilized by y irradiation. Atom Indonesia 13(2):1-3 (1987) Abstract only.
Hirashima et al. Inter-alpha-trypsin inhibitor is concentrated in the pericellular environment of mouse granulosa cells through hyaluronan-binding. Eur J Obstet Gynecol Reprod Biol. 73 :79-84 (1997).

(56) References Cited

OTHER PUBLICATIONS

Hori. Amniotic Membrane Transplantation and Immune Reaction. Folia Ophthalmologica Japonica 56(9):722-727 (2005) (English Abstract).

Howes et al. Receptor for Advanced Glycation End Products and Age-Related Macular Degeneration. Invest. Ophthalmol. Vis. Sci. 45(10):3713-3720 (2004).

Huang et al. A Serum-derived Hyaluronan-associated Protein (SHAP) Is the Heavy Chain of the Inter a-Trypsin Inhibitor. J Biol Chem 268(35):26725-76730 (1993).

Jadin et al. Characterization of a Novel Recombinant Hyaluronan Binding Protein for Tissue Hyaluronan Detection. Journal of Histochemistry & Cytochemistry 62(9):672-683 (2014).

Jester et al. Corneal Stromal Wound Healing in Refractive Surgery: the Role of Myofibroblasts. Prog. Retin. Eye Res. 18(3):311-356 (1999).

Jester et al. Induction of α-Smooth Muscle Actin Expression and Myofibroblast Transformation in Cultured Cornea Keratocytes. Cornea 15(5):505-516 (1996).

Keelan et al. Activin A Exerts both Pro- and -Anti-inflammatory Effects on Human Term Gestational Tissues. Placenta 21:38-43 (2000).

Kida et al. The SHAP-HA complex in sera from patients with rheumatoid arthritis and osteoarthritis. J Rheumatol 26(6):1230-1238 (1999).

Kishida et al. Hyaluronan (HA) and serum-derived hyaluronan-associated protein (SHAP)-HA complex as predictive markers of cervical ripening in premature labor. 49(2):105-108 (2008).

Kobayashi et al. Identification of structural domains in inter-alpha-trypsin inhibitor involved in calcium oxalate crystallization. Kidney Int 53:1727-1735 (1998).

Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).

Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) meeting on May 3-May 7, 2015 (Colorado Convention Center Denver, CO) Abstract No. 1126-B029 (2 pgs).

Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) meeting on May 3-May 7, 2015 (Colorado Convention Center Denver, CO) Abstract No. 2287-B0192 (2 pgs).

Kuznetsova et al. The N-terminal module of thrombospondin-1 interacts with the link domain of TSG-6 and enhances its covalent association with the heavy chains of inter-alpha-trypsin inhibitor. J Biol Chem 280:30899-30908 (2005).

Lawrence. Transforming Growth Factor-β: a general review. Eur. Cytokine Netw. 7:363-374 (1996).

Lee et al. Adhesion between Amniotic Membrane and Retinal Tissue and Inhibition of Amniotic Membrane on Cell Transformation. J Korean Ophthalmol Soc. 44(2):459-471 (2003) (Abstract Only).

Lee et al. An Agarose Gel Electrophoretic Method for Analysis of Hyaluronan Molecular Weight Distribution. Anal. Biochem. 219:278-287 (1994).

Li et al. An Experimental Study of the Effects of Human Amniotic Membrane on Human Retinal Pigment Epithelial Cell Proliferation in vitro. Acta Acadamiae Medicinae Militaris Tertia 25(5):407-409 (2003) (English Abstract).

Li et al. Reversal of myofibroblasts by amniotic membrane stromal extract. J Cell Physiol. 215(3):657-664 (2008).

Lieberman et al. Pharmaceutical Dosage Forms. 2 Ed. 1:209-214 (1990).

Logan et al. Decorin Attenuates Gliotic Scar Formation in the Rat Cerebral Hemisphere. Exp. Neurol. 159:504-510 (1999).

Marek et al. TGF-β-(transforming growth factor-β) in chronic inflammatory conditions—a new diagnostic and prognostic marker? Med. Sci. Monitl. 8(7):RA145-RA151 (2002).

Massague et al. Controlling TGF-β signaling. Genes and Development 14:627-644 (2000).

Moalli et al. Pathogen Recognition by the Long Pentraxin PTX3. Journal of Biomedicine and Biotechnology 2011:Article ID 830421 (15 pgs.) (2011).

Moller-Pedersen et al. Neutralizing antibody to TGF-β modulates stromal fibrosis but not regression of photoablative effect following PRK. Curr. Eye Res. 17:736-747 (1998).

Monteleone et al. SMAD7 in TGF-β-mediated negative regulation of gut inflammation. Trends in Immunology 25(10):513-517 (2004).

Na et al. Analysis of Human Amniotic Membrane Components as Proteinase Inhibitors for Development of Therapeutic Agent for Recalcitrant Keratitis. Trophoblast Res. 13:453-466 (1999).

Nakao et al. SMAD7: a new key player in TGF-b-associated disease. Trends in Molecular Medicine 8(8):361-363 (2002).

Neumann et al. High molecular weight hyaluronic acid inhibits advanced glycation endproduct-induced NF-kB activation and cytokine expression. FEBS Ltrs. 453:283-287(1999).

Obayashi et al. Role of serum-derived hyaluronan-associated protein-hyaluronan complex in ovarian cancer. Oncol Rep 19(5):1245-1251 (2008).

Ochsner et al. Decreased expression of tumor necrosis factor-alpha-stimulated gene 6 in cumulus cells of the cyclooxygenase2 and EP2 null mice. Endocrinology 144:1008-1019 (2003).

Oikawa et al. Inhibition of Angiogenesis by 15-Deoxyspergualin. J. Antibiotics 44(9):1033-1035 (1991).

PCT/US2006/37906 International Preliminary Report on Patentability dated Apr. 1, 2008.

PCT/US2006/37906 International Search Report and Written Opinion dated Jul. 11, 2007.

PCT/US2010/032452 International Preliminary Report on Patentability dated Oct. 25, 2011.

PCT/US2010/032452 International Search Report dated Dec. 27, 2010.

PCT/US2010/46675 International Preliminary Report on Patentability dated Feb. 28, 2012.

PCT/US2010/46675 International Search Report and Written Opinion dated May 30, 2011.

PCT/US2011/042679 International Preliminary Report on Patentability dated Jan. 8, 2013.

PCT/US2011/042679 International Search Report and Written Opinion dated Mar. 9, 2012.

PCT/US2013/049983 International Preliminary Report on Patentability dated Jan. 22, 2015.

PCT/US2013/049983 International Search Report and Written Opinion dated Nov. 29, 2013.

PCT/US2016/033558 International Preliminary Report on Patentability dated Nov. 30, 2017.

PCT/US2016/033558 International Search Report and Written Opinion dated Oct. 25, 2016.

Petraglia et al. Inhibin and Activin in Human Fetal Membranes: Evidence of a Local Effect on Prostaglandin Release. J. Clin. Endocrinol. Metab. 77(2):542-548 (1993).

Relucenti et al. Cumulus oophorus extracellular matrix in the human oocyte: a role for adhesive proteins. Ital J Anat Embryol 110(2 Supp 1):219-224 (2005).

Riley et al. Production of inhibin forms by the fetal membranes, decidua, placenta and fetus at parturition. Hum. Reprod. 15:578-583 (2000).

Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).

Roubelakis et al. Amniotic fluid and amniotic membrane stem cells: marker discovery. Stem Cells Int. 2012:107836 (2012).

Rugg et al. Characterization of complexes formed between TSG-6 and inter-alpha-inhibitor that act as intermediates in the covalent transfer of heavy chains onto hyaluronan. J Biol Chem 280(27):25674-25686 (2005).

(56) References Cited

OTHER PUBLICATIONS

Sakurai et al. Characterization of the Role of PTX3 In Enhancing The Anti-angiogenic Action Of HC.HA Purified From The Chorion. Arvo Annual Meeting Abstract Search And Program Planner. 2011:4881 (May 2011).
Saltzman. Drug Administration and Drug Effectiveness. Chapter 2. Drug Delivery—Engineering Principles for Drug Therapy. Oxford Press. p. 9-19 (2001).
Salustri et al. PTX3 plays a key role in the organization of the cumulus oophorus extracellular matrix and in in vivo fertilization. Development 131:1577-1586 (2004).
Sanggaard et al, The transfer of heavy chains from bikunin proteins to hyaluronan requires both TSG-6 and HC2. J Biol Chem 283(27):18530-18537 (2008).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Shen et al. The SHAP-hyaluronan complex in serum from patients with chronic liver diseases caused by hepatitis virus infection. Hepatol Res 34(3):178-186 (2006).
Singh et al. Encyclopedia of Pharmaceutical Technology 2nd Ed. pp. 751-753 (2002).
Singh et al. Microbiological safety and clinical efficacy of radiation sterilized amniotic membranes for treatment of second-degree burns. Burns 33:505-510 (2007).
Solomon et al. Suppression of Interleukin 1a and interleukin 1b in human limbal epithelial cells cultured on the amniotic membrane stromal matrix. Br. J. Ophthalmol 85:444-449 (2001).
Sun et al. Link protein as an enhancer of cumulus cell-oocyte complex expansion. Mol Reprod Dev 63:223-231 (2002).
Sur et al. Anti-inflammatory and anti-platelet aggregation activity of human placental extract. Acta Pharmacol Sin 24(2):187-192 (2003).
Tan et al. Structural and Biological Comparison of Cryopreserved and Fresh Amniotic membrane Tissues. Journal Biomaterial and Tissue Engineering 4:379-388 (2014).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Tseng et al. How Does Amniotic Membrane Work? Ocular Surface J. 2(3):177-187 (2004).
Tseng et al. Suppression of Transforming Growth Factor-Beta Isoforms, TGF-β Receptor Type II, and Myofibroblast Differentiation in Cultured Human Corneal and Limbal Fibroblasts by Amniotic Membrane Matrix. J. Cell Physiol. 179:325-335 (1999).
U.S. Appl. No. 11/528,902 Office Action dated Apr. 2, 2009.
U.S. Appl. No. 11/528,902 Office Action dated Dec. 16, 2009.
U.S. Appl. No. 11/528,902 Office Action dated Jan. 27, 2011.
U.S. Appl. No. 11/528,902 Office Action dated Sep. 8, 2010.
U.S. Appl. No. 11/528,980 Office Action dated Aug. 11, 2009.
U.S. Appl. No. 11/528,980 Office Action dated Jan. 10, 2011.
U.S. Appl. No. 11/528,980 Office Action dated Nov. 13, 2008.
U.S. Appl. No. 11/528,980 Office Action dated Oct. 15, 2010.
U.S. Appl. No. 11/529,658 Office Action dated Apr. 3, 2009.
U.S. Appl. No. 11/529,658 Office Action dated Dec. 16, 2009.
U.S. Appl. No. 11/529,658 Office Action dated Jan. 27, 2011.
U.S. Appl. No. 11/529,658 Office Action dated Sep. 3, 2010.
U.S. Appl. No. 11/535,924 Office Action dated Dec. 16, 2009.
U.S. Appl. No. 11/535,924 Office Action dated Jan. 31, 2011.
U.S. Appl. No. 11/535,924 Office Action dated Mar. 31, 2009.
U.S. Appl. No. 11/535,924 Office Action dated Sep. 8, 2010.
U.S. Appl. No. 13/262,725 Office Action dated Feb. 25, 2015.
U.S. Appl. No. 13/262,725 Office Action dated Jul. 17, 2014.
U.S. Appl. No. 13/322,896 Office Action dated Jan. 20, 2016.
U.S. Appl. No. 13/322,896 Office Action dated Jul. 6, 2015.
U.S. Appl. No. 13/322,896 Office Action dated Oct. 22, 2014.
U.S. Appl. No. 13/322,896 Office Action dated Oct. 4, 2016.
U.S. Appl. No. 13/322,896 Office Action dated Sep. 6, 2017.
U.S. Appl. No. 13/453,840 Office Action dated Aug. 21, 2012.
U.S. Appl. No. 13/704,231 Office Action dated Aug. 16, 2017.
U.S. Appl. No. 13/704,231 Office Action dated Aug. 2, 2016.
U.S. Appl. No. 13/704,231 Office Action dated Feb. 11, 2016.
U.S. Appl. No. 13/704,231 Office Action dated Jan. 19, 2017.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,204 Office Action dated Jan. 22, 2016.
U.S. Appl. No. 13/802,204 Office Action dated Jun. 15, 2018.
U.S. Appl. No. 13/802,204 Office Action dated Oct. 4, 2016.
U.S. Appl. No. 13/802,204 Office Action dated Sep. 7, 2017.
U.S. Appl. No. 13/802,264 Office Action dated Jul. 16, 2015.
U.S. Appl. No. 13/802,264 Office Action dated Nov. 28, 2014.
U.S. Appl. No. 13/802,359 Office Action dated Dec. 10, 2014.
U.S. Appl. No. 13/802,447 Office Action dated Dec. 15, 2014.
U.S. Appl. No. 14/414,047 Office Action dated Feb. 13, 2017.
U.S. Appl. No. 14/414,047 Office Action dated Jul. 19, 2017.
U.S. Appl. No. 14/414,047 Office Action dated Jul. 8, 2016.
U.S. Appl. No. 14/848,143 Office Action dated Jun. 21, 2017.
U.S. Appl. No. 14/848,143 Office Action dated Oct. 20, 2016.
U.S. Appl. No. 14/848,148 Office Action dated Mar. 20, 2017.
U.S. Appl. No. 14/848,148 Office Action dated Oct. 28, 2016.
U.S. Appl. No. 14/848,153 Office Action dated Apr. 21, 2017.
U.S. Appl. No. 14/848,153 Office Action dated Oct. 25, 2016.
U.S. Appl. No. 14/869,609 Office Action dated Jun. 2, 2017.
U.S. Appl. No. 14/869,609 Office Action dated May 14, 2018.
U.S. Appl. No. 14/869,609 Office Action dated Oct. 17, 2016.
U.S. Appl. No. 14/880,135 Office Action dated Dec. 23, 2016.
U.S. Appl. No. 14/886,946 Office Action dated Apr. 18, 2016.
U.S. Appl. No. 14/886,946 Office Action dated Jan. 8, 2018.
U.S. Appl. No. 14/886,946 Office Action dated May 19, 2017.
U.S. Appl. No. 14/886,946 Office Action dated May 28, 2019.
U.S. Appl. No. 14/886,946 Office Action dated Oct. 5, 2016.
U.S. Appl. No. 14/886,946 Office Action dated Sep. 7, 2018.
U.S. Appl. No. 14/933,106 Office Action dated Aug. 31, 2018.
U.S. Appl. No. 14/996,051 Office Action dated Apr. 2, 2018.
U.S. Appl. No. 14/996,051 Office Action dated Jul. 24, 2017.
U.S. Appl. No. 14/996,051 Office Action dated Sep. 7, 2018.
U.S. Appl. No. 15/160,487 Office Action dated Jun. 1, 2018.
U.S. Appl. No. 15/160,487 Office Action dated Oct. 10, 2018.
U.S. Appl. No. 15/195,189 Office Action dated May 30, 2018.
U.S. Appl. No. 15/214,706 Office Action dated Mar. 15, 2018.
U.S. Appl. No. 15/214,706 Office Action dated Oct. 4, 2018.
U.S. Appl. No. 15/215,228 Office Action dated May 30, 2018.
U.S. Appl. No. 15/636,227 Office Action dated Sep. 27, 2018.
U.S. Appl. No. 15/879,042 Office Action dated Jul. 8, 2019.
U.S. Appl. No. 16/274,123 Office Action dated May 28, 2019.
Verbeek et al. Induction of alpha-smooth muscle actin expression in cultured human brain pericytes by transforming growth factor-beta 1. Am. J. Pathol. 144:372-382 (1994).
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).
Wu et al. Wound healing effects of porcine placental extracts on rats with thermal injury. Br J Dermatol 148(2):236-245 (2003).
Yabushita et al. Clinicopathological Role of Serum-Derived Hyaluronan-Associated Protein (SHAP)-Hyaluronan Complex in Endometrial Cancer. Obstet Gynecol Inc. 2011:739150 (2011).
Yamaguchi et al. Negative regulation of transforming growth factor-β by the proteoglycan decorin. Nature 346(6281):281-284 (1990).
Yingsung et al. Molecular heterogeneity of the SHAP-hyaluronan complex. Isolation and characterization of the complex in synovial fluid from patients with rheumatoid arthritis. J Biol Chem 2878(35):32710-32718 (2003).

(56) References Cited

OTHER PUBLICATIONS

Yoneda et al. Hyaluronic acid associated with the surfaces of cultured fibroblasts is linked to a serum-derived 85-kDa protein. J Biol Chem 265(9):5247-5257 (1990).

Yoshida. Placenta Power: For Health and Beauty—A useful guide for those seeking placenta-based remedies. Downloaded from http://www.melsmon.co.jp/img/commom/PlacentaPowerp002-121_04-09-08.pdf. (p. 1-41) (Aug. 2001).

Zhang et al. Constitutive Expression of Inter-α-inhibitor (IαI) Family Proteins and Tumor Necrosis Factor-stimulatedGene-6 (TSG-6) by Human Amniotic Membrane Epithelial and Stromal Cells Supporting Formation of the Heavy Chain-Hyaluronan (HC-HA) Complex. J of Biological Chemistry 287(15):12433-12444 (2012).

Zhang et al. Constitutive Expression of Pentraxin 3 (PTX3) Protein by Human Amniotic Membrane Cells Leads to Formation of the Heavy Chain (HC)-Hyaluronan (HA)-PTX3 Complex. J Biol Chem 289(19):13531-13542 (2014).

Zhao et al. Evidence for the covalent binding of SHAP, heavy chains of inter-alpha-trypsin inhibitor, to hyaluronan. J Biol Chem 270:26657-26663 (1995).

Zhuo et al. Inter-α-trypsin Inhibitor, a Covalent Protein-Glycosaminoglycan-Protein Complex. J Biol Chem 279(37):38079-38082 (2004).

Zhuo et al. SHAP potentiates the CD44-mediated leukocyte adhesion to the hyaluronan substratum. J Biol Chem 281(29):20303-20314 (2006).

He. Prevention of Proliferative Vitreoretinopathy by HC-HA/PTX3. Available at https://grantome.com/grant/NIH/R43-EY025447-01 (project started May 1, 2015).

Sood et al. Gene expression patterns in human placenta. PNAS 103(16):5478-5483 (2006).

U.S. Appl. No. 14/886,946 Office Action dated Oct. 25, 2019.
U.S. Appl. No. 14/996,051 Office Action dated Dec. 5, 2019.
U.S. Appl. No. 16/274,123 Office Action dated Nov. 27, 2019.
U.S. Appl. No. 16/898,309 Office Action dated Mar. 7, 2022.

* cited by examiner

COMPOSITIONS AND METHODS FOR PREVENTING THE PROLIFERATION AND EPITHELIAL-MESENCHYMAL TRANSITION OF EPITHELIAL CELLS

CROSS REFERENCE

This application is a continuation of application Ser. No. 15/160,487, filed on May 20, 2016, now issued as U.S. Pat. No. 10,342,831, issued on Jul. 9, 2019, which claims the benefit of and right of priority to U.S. Provisional Application No. 62/164,281 filed May 20, 2015, both of which are incorporated herein by reference in their entireties.

STATEMENT AS TO FEDERALLY SPONSORED RESEARCH

This invention was made with government support under Contract number R44EY025447 by the National Institutes of Health. The government has certain rights in this invention.

SUMMARY OF THE INVENTION

Disclosed herein, in certain embodiments, are methods for preventing or reducing proliferation, cell migration, or epithelial-mesenchymal transition (EMT) of epithelial cells in an individual in need thereof, comprising: administering to the individual a therapeutically effective amount of a composition, comprising: (a) a preparation of fetal support tissue; and (b) a pharmaceutically acceptable diluent, excipient, vehicle, or carrier, thereby preventing or reducing the proliferation, cell migration, or EMT of epithelial cells, wherein the epithelial cells are not retinal pigment epithelial cells. In some embodiments, the EMT is associated with a disease or disorder other than proliferative vitreoretinopathy (PVR). In some embodiments, the EMT is associated with a disease or disorder selected from cancer, proliferative diabetic retinopathy, fibrotic lesion, and Retro-corneal membrane. In some embodiments, the fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the epithelial cells are selected from conjunctival epithelial cells, corneal epithelial cells, limbal epithelial cells, and renal epithelial cells. In some embodiments, the epithelial cells are human epithelial cells. In some embodiments, the human epithelial cells are retinal pigment epithelial cells (RPE). In some embodiments, the human epithelial cells are conjunctival epithelial cells. In some embodiments, the human epithelial cells are corneal epithelial cells. In some embodiments, the human epithelial cells are limbal epithelial cells. In some embodiments, the human epithelial cells are renal epithelial cells. In some embodiments, the preparation of fetal support tissue is an extract of fetal support tissue, a homogenate, a powder, morselized fetal support tissue, pulverized fetal support tissue, ground fetal support tissue, purified HC-HA/PTX3, or a combination thereof. In some embodiments, the composition is a gel, a solution, or a suspension. In some embodiments, the composition is in an injectable form. In some embodiments, the preparation of fetal support tissue comprises substantially isolated HC-HA/PTX3. In some embodiments, the preparation of fetal support tissue consists of substantially isolated HC-HA/PTX3. In some embodiments, the preparation of fetal support tissue comprises reconstituted HC-HA/PTX3. In some embodiments, the preparation of fetal support tissue comprises high molecular weight hyaluronan (HA) that is cross-linked by a covalent bond to the heavy chain of inter-α-trypsin inhibitor (IαI), the high molecular weight HA having a molecular weight greater than 1000 kDa. In some embodiments, the preparation of fetal support tissue comprises pentraxin 3 (PTX-3). In some embodiments, the preparation of fetal support tissue comprises tumor necrosis factor-stimulated gene 6 protein (TSG-6). In some embodiments, the preparation of fetal support tissue comprises thrombospondin-1 (TSP-1). In some embodiments, the ratio of total protein to HA in the composition is between 500 parts protein:1 part HA and 500 parts HA:1 parts protein. In some embodiments, the composition prevents the proliferation and EMT of epithelial cells by counteracting the actions of growth factors and cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF, and IFN-γ. In some embodiments, the composition further comprises an aqueous adjuvant. In some embodiments, the composition is for local administration. In some embodiments the composition if formulated for injection. In some embodiments, the composition is formulated for intraocular injection, subretinal injection, intravitreal injection, periocular injection, subconjunctival injection, retrobulbar injection, intracameral injection, or sub-Tenon's injection.

Disclosed herein, in certain embodiments, are methods method for treating or preventing Proliferative Vitreoretinopathy (PVR) in an individual in need thereof, comprising administering to the individual a therapeutically effective amount of an injectable composition, consisting essentially of: (a) substantially isolated HC-HA/PTX3, reconstituted HC-HA/PTX3, or a combination thereof; and (b) a pharmaceutically acceptable diluent, excipient, vehicle, or carrier, thereby treating or preventing PVR. In some embodiments, the composition consists of: (a) substantially isolated HC-HA/PTX3, reconstituted HC-HA/PTX3, or a combination thereof; and (b) a pharmaceutically acceptable diluent, excipient, vehicle, or carrier. In some embodiments, the composition consists of reconstituted HC-HA/PTX3 and a pharmaceutically acceptable diluent, excipient, vehicle, or carrier. In some embodiments, the composition consists of substantially isolated HC-HA/PTX3 and a pharmaceutically acceptable diluent, excipient, vehicle, or carrier. In some embodiments, the substantially isolated HC-HA/PTX3 is isolated from fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the substantially isolated HC-HA/PTX3 is isolated from fetal support tissue by ultracentrifugation. In some embodiments, the therapeutically effective amount is effective for preventing or reducing the proliferation, cell migration or EMT of epithelial cells. In some embodiments, the epithelial cells are retinal pigment epithelial cells (RPE). In some embodiments, the epithelial cells are human epithelial cells. In some embodiments, the human epithelial cells are retinal epithelial cells. In some embodiments, the injectable composition is a gel, a solution, or a suspension. In some embodiments, the composition comprises high molecular weight hyaluronan (HA) that is cross-linked by a covalent bond to the heavy chain of inter-α-trypsin inhibitor (IαI), the high molecular weight HA having a molecular weight greater than 1000 kDa. In some embodiments, the composition comprises pentraxin 3 (PTX-3). In some embodiments, the composition comprises tumor necrosis factor-stimulated gene 6 protein (TSG-6). In some embodiments, the ratio of total protein to HA in the injectable composition is between 500 parts protein:1 part HA and 500 parts HA:1 parts protein. In some embodiments, the injectable composition prevents the proliferation and EMT of epithelial cells by inhibiting or suppressing the activity of one or more growth factors or cytokines. In some embodiments, the growth factors and cytokines are selected from the group consisting of: EGF, FGF-2, PDGF-A, PDGF-AB, PDGF-B, PDGF-C, TGFβ1, TGF-β2, TGF-β3, CTGF, HGF, IGF-1, G-CSF, IL-6, MCP-1, TNF-α, VEGF, and IFN-γ. In some embodiments, the injectable composition further comprises an aqueous adjuvant. In some embodiments, the injectable composition is for local administration. In some embodiments, the injectable composition is formulated for intraocular injection, subretinal injection, intravitreal injection, periocular injection, subconjunctival injection, retrobulbar injection, intracameral injection or sub-Tenon's injection. In some embodiments, the composition is formulated for intravitreal injection.

Disclosed herein, in certain embodiments, are methods method for treating or preventing Proliferative Vitreoretinopathy (PVR) in an individual in need thereof, comprising administering to the individual a therapeutically effective amount of an injectable composition, consisting essentially of: (a) substantially isolated HC-HA/PTX3, reconstituted HC-HA/PTX3, or a combination thereof; (b) an additional therapeutic agent; and (c) a pharmaceutically acceptable diluent, excipient, vehicle, or carrier, thereby treating or preventing PVR. In some embodiments, the composition consists of: (a) substantially isolated HC-HA/PTX3, reconstituted HC-HA/PTX3, or a combination thereof; (b) an additional therapeutic agent; and (c) a pharmaceutically acceptable diluent, excipient, vehicle, or carrier. In some embodiments, the additional therapeutic agent is an additional agent for treating PVR. In some embodiments, the additional therapeutic agent is selected from the group consisting of: oral Accutane, intravitreal triamcinolone acetonide, ranibizumab, bevacizumab, dasatinib, pegaptanib sodium, N-acetyl-cysteine (NAC), pioglitazone, glucosamine, genistin, geldanamycin, fausdil, resveratrol, hepatocyte growth factor (HGF), BMP-7, LY-364947, diosgenin, emodin, pentoxyfilline, dipyridamole, a peroxisome proliferative-activated receptor-gamma (PPARγ) agonist, a female sex hormone, and an antioxidant. In some embodiments, the female sex hormone comprises estradiol or progesterone. In some embodiments, the antioxidant comprises beta carotene, vitamin C, vitamin E, lutein, zeaxanthin, and omega-3 fatty acids. In some embodiments the additional therapeutic agent is an additional agent for treating inflammation. In some embodiments, the composition consists of: (a) substantially isolated HC-HA/PTX3, reconstituted HC-HA/PTX3, or a combination thereof; (b) an additional therapeutic agent; and (c) a pharmaceutically acceptable diluent, excipient, vehicle, or carrier. In some embodiments, the composition consists of reconstituted HC-HA/PTX3, an additional therapeutic agent, and a pharmaceutically acceptable diluent, excipient, vehicle, or carrier. In some embodiments, the composition consists of substantially isolated HC-HA/PTX3, an additional therapeutic agent, and a pharmaceutically acceptable diluent, excipient, vehicle, or carrier. In some embodiments, the substantially isolated HC-HA/PTX3 is isolated from fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the substantially isolated HC-HA/PTX3 is isolated from fetal support tissue by ultracentrifugation. In some embodiments, the composition further comprises an additional therapeutic agent. In some embodiments, the therapeutically effective amount is effective for preventing or reducing the proliferation, cell migration or EMT of epithelial cells. In some embodiments, the epithelial cells are retinal pigment epithelial cells (RPE). In some embodiments, the epithelial cells are human epithelial cells. In some embodiments, the human epithelial cells are retinal epithelial cells. In some embodiments, the injectable composition is a gel, a solution, or a suspension. In some embodiments, the composition comprises high molecular weight hyaluronan (HA) that is cross-linked by a covalent bond to the heavy chain of inter-α-trypsin inhibitor (IαI), the high molecular weight HA having a molecular weight greater than 1000 kDa. In some embodiments, the composition comprises pentraxin 3 (PTX-3). In some embodiments, the composition comprises tumor necrosis factor-stimulated gene 6 protein (TSG-6). In some embodiments, the preparation of fetal support tissue comprises thrombospondin-1 (TSP-1). In some embodiments, the ratio of total protein to HA in the injectable composition is between 500 parts protein:1 part HA and 500 parts HA:1 parts protein. In some embodiments, the injectable composition prevents the proliferation and EMT of epithelial cells by inhibiting or suppressing the activity of one or more growth factors or cytokines. In some embodiments, the growth factors and cytokines are selected from the group consisting of: EGF, FGF-2, PDGF-A, PDGF-AB, PDGF-B, PDGF-C, TGFβ1, TGF-β2, TGF-β3, CTGF, HGF, IGF-1, G-CSF, IL-6, MCP-1, TNF-α, VEGF, and IFN-γ. In some embodiments, the injectable composition further comprises an aqueous adjuvant. In some embodiments, the injectable composition is for local administration. In some embodiments, the injectable composition is formulated for intraocular injection, subretinal injection, intravitreal injection, periocular injection, subconjunctival injection, retrobulbar injection, intracameral injection or sub-Tenon's injection. In some embodiments, the composition is formulated for intravitreal injection.

Disclosed herein, in certain embodiments, are methods for treating or preventing Proliferative Vitreoretinopathy (PVR) in an individual in need thereof, comprising administering to the individual a therapeutically effective amount of an injectable composition, comprising: a preparation of fetal support tissue comprising HC-HA/PTX3 and at least one other component of fetal support tissue; and a pharmaceutically acceptable diluent, excipient, vehicle, or carrier, thereby treating or preventing PVR. In some embodiments, the fetal support tissue is placenta, placental amniotic membrane, umbilical cord, umbilical cord amniotic membrane, chorion, amnion-chorion, amniotic stroma, amniotic jelly, amniotic fluid, or a combination thereof. In some embodiments, the fetal support tissue is frozen or previously frozen.

In some embodiments, the fetal support tissue is human, non-human primate, bovine, or porcine. In some embodiments, the fetal support tissue is human. In some embodiments, the therapeutically effective amount is an amount effective for preventing or reducing the proliferation, cell migration or EMT of epithelial cells. In some embodiments, the epithelial cells are retinal pigment epithelial (RPE) cells. In some embodiments, the preparation of fetal support tissue is an extract of fetal support tissue, micronized fetal support tissue, a homogenate, a powder, morselized fetal support tissue, pulverized fetal support tissue, ground fetal support tissue, purified HC-HA/PTX3, or a combination thereof. In some embodiments, the composition is a gel, a solution, or a suspension. In some embodiments, the composition is formulated for intraocular injection, subretinal injection, intravitreal injection, periocular injection, subconjunctival injection, retrobulbar injection, intracameral injection or sub-Tenon's injection.

Disclosed herein, in certain embodiments, are compositions for preventing or reducing proliferation, cell migration, and/or epithelial-mesenchymal transition (EMT) of epithelial cells, comprising: (a) a preparation of fetal support tissue; and (b) a pharmaceutically acceptable diluent, excipient, vehicle, or carrier, wherein the epithelial cells are not retinal pigment epithelial cells. In some embodiments, the EMT is associated with a disease or disorder other than proliferative vitreoretinopathy. In some embodiments, the EMT is associated with a disease or disorder selected from cancer, proliferative diabetic retinopathy, fibrotic lesion, and Retro-corneal membrane. In some embodiments, the fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the composition is in a therapeutically effective amount for preventing or reducing the proliferation, cell migration or EMT of epithelial cells. In some embodiments, the epithelial cells are selected from conjunctival epithelial cells, corneal epithelial cells, limbal epithelial cells, and renal epithelial cells. In some embodiments, the epithelial cells are human epithelial cells. In some embodiments, the human epithelial cells are retinal pigment epithelial cells (RPE). In some embodiments, the human epithelial cells are conjunctival epithelial cells. In some embodiments, the human epithelial cells are corneal epithelial cells. In some embodiments, the human epithelial cells are limbal epithelial cells. In some embodiments, the human epithelial cells are renal epithelial cells. In some embodiments, the preparation of fetal support tissue is an extract of fetal support tissue, micronized fetal support tissue, a homogenate, a powder, morselized fetal support tissue, pulverized fetal support tissue, ground fetal support tissue, or purified HC-HA/PTX3. In some embodiments, the composition is a gel, a solution, or a suspension. In some embodiments, the preparation of fetal support tissue comprises HC-HA/PTX3. In some embodiments, the preparation of fetal support tissue comprises substantially isolated HC-HA/PTX3. In some embodiments, the preparation of fetal support tissue consists of substantially isolated HC-HA/PTX3. In some embodiments, the preparation of fetal support tissue comprises reconstituted HC-HA/PTX3. In some embodiments, the preparation of fetal support tissue comprises high molecular weight hyaluronan (HA) that is cross-linked by a covalent bond to the heavy chain of inter-a-trypsin inhibitor (IαI), the high molecular weight HA having a molecular weight greater than 1000 kDa. In some embodiments, the preparation of fetal support tissue comprises pentraxin 3 (PTX-3). In some embodiments, the preparation of fetal support tissue comprises tumor necrosis factor-stimulated gene 6 protein (TSG-6). In some embodiments, the preparation of fetal support tissue comprises thrombospondin-1 (TSP-1). In some embodiments, the ratio of total protein to HA in the injectable composition is between 500 parts protein:1 part HA and 500 parts HA:1 parts protein. In some embodiments, the injectable composition prevents the proliferation and EMT of epithelial cells by inhibiting the actions of growth factors and cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF and IFN-γ. In some embodiments, the injectable composition further comprises an aqueous adjuvant. In some embodiments, the injectable composition is for local administration. In some embodiments, the composition is formulated for injection. In some embodiments, the injectable composition is formulated for intraocular injection, subretinal injection, intravitreal injection, periocular injection, subconjunctival injection, retrobulbar injection, intracameral injection, or sub-Tenon's injection.

Disclosed herein, in certain embodiments, are injectable compositions for treating or preventing Proliferative Vitreoretinopathy (PVR), comprising: (a) substantially isolated HC-HA/PTX3, reconstituted HC-HA/PTX3, or a combination thereof; and (b) a pharmaceutically acceptable diluent, excipient, vehicle, or carrier. In some embodiments, the composition consists of: (a) substantially isolated HC-HA/PTX3, reconstituted HC-HA/PTX3, or a combination thereof; and (b) a pharmaceutically acceptable diluent, excipient, vehicle, or carrier. In some embodiments, the composition consists of reconstituted HC-HA/PTX3 and a pharmaceutically acceptable diluent, excipient, vehicle, or carrier. In some embodiments, the composition consists of substantially isolated HC-HA/PTX3 and a pharmaceutically acceptable diluent, excipient, vehicle, or carrier. In some embodiments, the substantially isolated HC-HA/PTX3 is isolated from fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the substantially isolated HC-HA/PTX3 is isolated from fetal support tissue by ultracentrifugation. In some embodiments, the injectable composition is in a therapeutically effective amount for preventing or reducing the proliferation, cell migration or EMT of epithelial cells. In some embodiments, the epithelial cells are retinal pigment epithelial cells (RPE). In some embodiments, the epithelial cells are human epithelial cells. In some embodiments, the human epithelial cells are retinal epithelial cells. In some embodiments, the injectable composition is a gel, a solution, or a suspension. In some embodiments, the preparation of fetal support tissue comprises high molecular weight hyaluronan (HA) that is cross-linked by a covalent bond to the heavy chain of inter-a-trypsin inhibitor (IαI), the high molecular weight HA having a molecular weight greater than 1000 kDa. In some embodiments, the preparation of fetal support tissue comprises pentraxin 3 (PTX-3). In some embodiments, the preparation of fetal support tissue comprises tumor necrosis factor-stimulated gene 6 protein (TSG-6). In some embodiments, the ratio of total protein to HA in the injectable composition is between 500 parts protein:1 part HA and 500 parts HA:1 parts protein. In some embodiments, the injectable composition prevents the proliferation and EMT of epithelial cells by inhibiting or suppressing the activity of growth factors and/or cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF and IFN-γ. In some embodiments, the injectable composition further comprises an aqueous adjuvant. In some embodiments, the injectable composition is for local administration. In some embodiments, the injectable composition is formulated for intraocular injection, subretinal injection, intravitreal injection, periocular injection, subconjunctival injection, retrobulbar injection, intracameral injection, or sub-Tenon's injection.

Disclosed herein, in certain embodiments, are injectable compositions for treating or preventing Proliferative Vitreoretinopathy (PVR), consisting essentially of: (a) substantially isolated HC-HA/PTX3, reconstituted HC-HA/PTX3, or a combination thereof; (b) an additional therapeutic agent; and (c) a pharmaceutically acceptable diluent, excipient, vehicle, or carrier. In some embodiments, the composition consists of: (a) substantially isolated HC-HA/PTX3, reconstituted HC-HA/PTX3, or a combination thereof (b) an additional therapeutic agent; and (c) a pharmaceutically acceptable diluent, excipient, vehicle, or carrier. In some embodiments, the composition consists of reconstituted HC-HA/PTX3, an additional therapeutic agent, and a pharmaceutically acceptable diluent, excipient, vehicle, or carrier. In some embodiments, the composition consists of substantially isolated HC-HA/PTX3, an additional therapeutic agent, and a pharmaceutically acceptable diluent, excipient, vehicle, or carrier. In some embodiments, the substantially isolated HC-HA/PTX3 is isolated from fetal support tissue is selected from the group consisting of: placenta, placental amniotic membrane, umbilical cord, umbilical cord amniotic membrane, chorion, amnion-chorion, amniotic stroma, amniotic jelly, amniotic fluid, and a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the substantially isolated HC-HA/PTX3 is isolated from fetal support tissue by ultracentrifugation. In some embodiments, the additional therapeutic agent is selected from the group consisting of: oral Accutane, intravitreal triamcinolone acetonide, ranibizumab, bevacizumab, dasatinib, pegaptanib sodium, N-acetyl-cysteine (NAC), pioglitazone, glucosamine, genistin, geldanamycin, fausdil, resveratrol, hepatocyte growth factor (HGF), BMP-7, LY-364947, diosgenin, emodin, pentoxyfilline, dipyridamole, a peroxisome proliferative-activated receptor-gamma (PPARγ) agonist, a female sex hormone, and an antioxidant. In some embodiments, the female sex hormone comprises estradiol or progesterone. In some embodiments, the antioxidant comprises beta carotene, vitamin C, vitamin E, lutein, zeaxanthin, and omega-3 fatty acids. In some embodiments, the injectable composition is in a therapeutically effective amount for preventing or reducing the proliferation, cell migration or EMT of epithelial cells. In some embodiments, the epithelial cells are retinal pigment epithelial cells (RPE). In some embodiments, the epithelial cells are human epithelial cells. In some embodiments, the human epithelial cells are retinal epithelial cells. In some embodiments, the injectable composition is a gel, a solution, or a suspension. In some embodiments, the preparation of fetal support tissue comprises high molecular weight hyaluronan (HA) that is cross-linked by a covalent bond to the heavy chain of inter-a-trypsin inhibitor (IαI), the high molecular weight HA having a molecular weight greater than 1000 kDa. In some embodiments, the preparation of fetal support tissue comprises pentraxin 3 (PTX-3). In some embodiments, the preparation of fetal support tissue comprises tumor necrosis factor-stimulated gene 6 protein (TSG-6). In some embodiments, the ratio of total protein to HA in the injectable composition is between 500 parts protein:1 part HA and 500 parts HA:1 parts protein. In some embodiments, the injectable composition prevents the proliferation and EMT of epithelial cells by inhibiting or suppressing the activity of growth factors and/or cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF and IFN-γ. In some embodiments, the injectable composition further comprises an aqueous adjuvant. In some embodiments, the injectable composition is for local administration. In some embodiments, the injectable composition is formulated for intraocular injection, subretinal injection, intravitreal injection, periocular injection, subconjunctival injection, retrobulbar injection, intracameral injection, or sub-Tenon's injection.

Disclosed herein, in certain embodiments, are injectable compositions for treating or preventing Proliferative Vitreoretinopathy (PVR) comprising: a preparation of fetal support tissue comprising HC-HA/PTX3 and at least one other component of fetal support tissue; and a pharmaceutically acceptable diluent, excipient, vehicle, or carrier; wherein the composition is suitable for injection. In some embodiments, the fetal support tissue is placenta, placental amniotic membrane, umbilical cord, umbilical cord amniotic membrane, chorion, amnion-chorion, amniotic stroma, amniotic jelly, amniotic fluid, or a combination thereof. In some embodiments, the fetal support tissue is frozen or previously frozen. In some embodiments, the fetal support tissue is human, non-human primate, bovine, or porcine. In some embodiments, the fetal support tissue is human. In some embodiments, the composition is in an amount effective for preventing or reducing the proliferation, cell migration or EMT of epithelial cells. In some embodiments, the epithelial cells are retinal pigment epithelial (RPE) cells. In some embodiments, the preparation of fetal support tissue is an extract of fetal support tissue, micronized fetal support tissue, a homogenate, a powder, morselized fetal support tissue, pulverized fetal support tissue, ground fetal support tissue, purified HC-HA/PTX3, or a combination thereof. In some embodiments, the composition is a gel, a solution, or a suspension. In some embodiments, the composition is formulated for intraocular injection, subretinal injection, intravitreal injection, periocular injection, subconjunctival injection, retrobulbar injection, intracameral injection or sub-Tenon's injection.

BRIEF DESCRIPTION OF THE FIGURES

FIG. 2A provides a schematic illustration of HC-HA/PTX3 formation.

FIG. 2B illustrates HC-HA/PTX3 purified from human AME. FIG. 2C illustrates that the HC-HA/PTX3 purified from AME comprises HC1. FIG. 2D illustrates that HC-HA/PTX3 purified from AME comprises PTX3.

FIG. 3A illustrates that HC-HA/PTX3 downregulates canonical Wnt signaling in human limbal epithelial progenitor cells (LEPCs) and niche cells (LNCs). FIG. 3B illustrates immunostaining of β-catenin and C-JUN seeded either on Matrigel or on immobilized HC-HA/PTX3.

FIG. 4A illustrates TGF-β1 expression in Human Corneal Fibroblasts (HCFs) seeded on plastic, HA, or HC-HA/PTX3, both with and without addition of exogenous TGF-β1.

FIG. 4B illustrates TGF-β2 expression in HCFs seeded on plastic, HA, or HC-HA/PTX3, both with and without addition of exogenous TGF-β1. FIG. 4C illustrates TGF-β3 expression in HCFs seeded on plastic, HA, or HC-HA/PTX3, both with and without addition of exogenous TGF-β1.

FIG. 4D exemplifies a Northern blot showing expression of TGF-βRI, TGF-βRII, and TGF-βIII in HCFs seeded on plastic, HA, or HC-HA/PTX3, both with and without addition of exogenous TGF-β1.

FIG. 5A illustrates HC-HA/PTX3 does not affect the viability of normal ARPE-19 cells. FIG. 5B illustrates proliferation of ARPE-19 cells using immunostaining. 5C illustrates proliferation of ARE-19 cells.

FIG. 6A illustrates nuclear localization of phosphorylated Smad2/3 using immunostaining. FIG. 6B illustrates nuclear localization of phosphorylated Smad2/3.

FIG. 7A exemplifies fundus photographs of a normal rabbit eye without PVR. FIG. 7B exemplifies a rabbit with tractional PVR four weeks after gas vitrectomy and intravitreal injection of RPE cells. FIG. 7C exemplifies a cross-section of the normal rabbit eye without PVR after enucleation. FIG. 7D exemplifies a cross-section of the eye of the rabbit with tractional PVR with retinal detachment after enucleation.

DETAILED DESCRIPTION OF THE INVENTION

Figure 1:
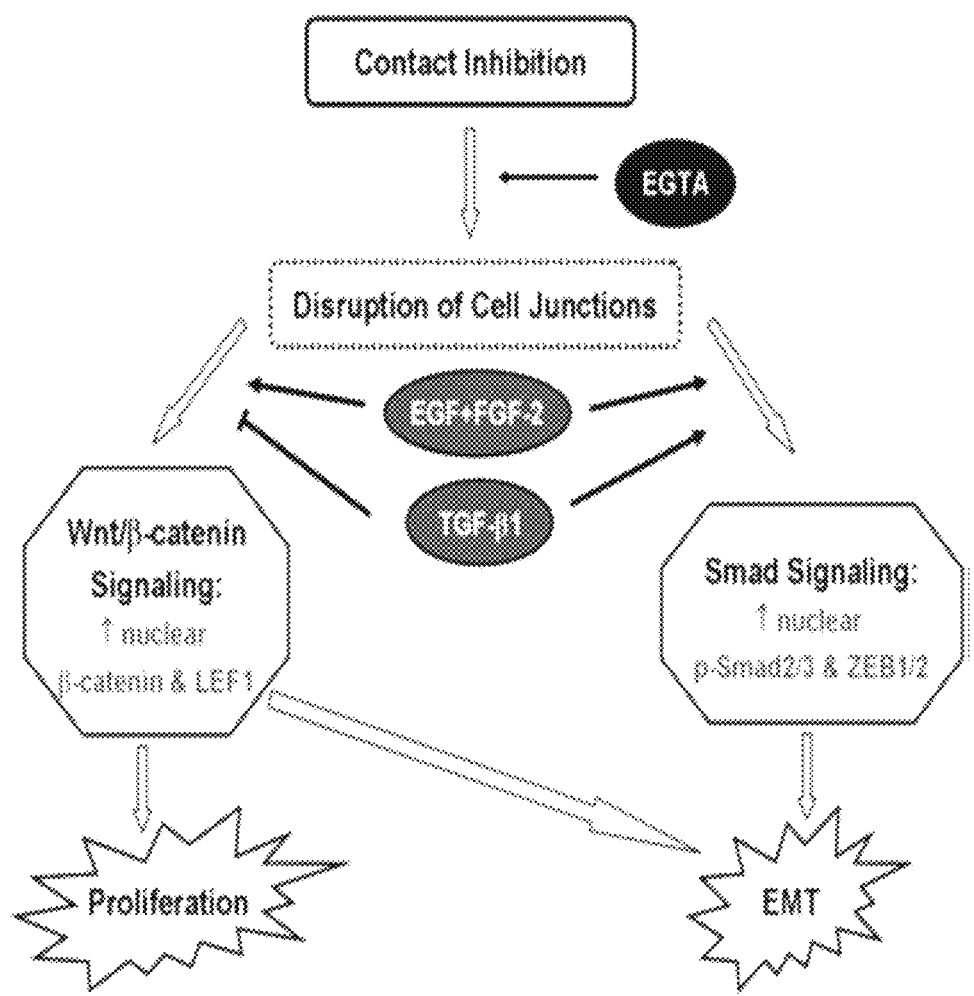
FIG. 1 illustrates the signaling pathways in the regulating of EMT with or without proliferation by growth factors.

The present application describes compositions and methods for preventing or reducing the proliferation, cell migration, and/or epithelial-mesenchymal transition (EMT) of epithelial cells, wherein the epithelial cells are human epithelial cells and the human epithelial cells are selected from: retinal pigment epithelial, conjunctival, retinal, corneal, limbal, or renal epithelial cells. Additionally, the present application describes compositions and methods for the prevention and treatment of proliferative vitreoretinopathy in an individual in need thereof.

It is known that proliferation, cell migration and EMT occur when epithelial cells such as, for example, retinal pigment epithelial, human conjunctival, retinal, corneal, limbal, or renal epithelial cells are exposed to growth factors and cytokines such as, for example, EGF, FGF-2, PDGF-A, PDGF-AB, PDGF-B, PDGF-C, TGF-$\beta$1, TGF-$\beta$2, TGF-$\beta$3, CTGF, HGF, IGF-1, G-CSF, IL-6, MCP-1, TNF-$\alpha$, VEGF or IFN-$\gamma$ and ethylene glycol tetraacetic acid (EGTA) either in vitro or in vivo.

Further, it is known that transplantation of cryopreserved amniotic membrane (AM) tissue onto the ocular surface provides anti-proliferative, anti-inflammatory, anti-scarring and anti-angiogenic actions in both corneal and limbal epithelial cells to promote wound healing.

What is needed is a composition that prevents or reduces proliferation, cell migration and EMT of epithelial cells, can be administered without the need of surgical transplantation and can additionally be administered to non-surface epithelial cells such as, for example, retinal and renal epithelial cells.

A description of certain embodiments follows. It will be understood that the particular embodiments of the application are shown by way of illustration and not as limitations of the application.

Certain Terminology

Unless defined otherwise, all technical and scientific terms used herein have the same meaning as is commonly understood by one of skill in the art to which the claimed subject matter belongs. All patents, patent applications, published, applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, ranges and amounts can be expressed as "about" a particular value or range. About also includes the exact amount. Hence, "about 5 µg" means "about 5 µg" and also "5 µg." Generally, the term "about" includes an amount that would be expected to be within experimental error.

As used herein, the terms "subject", "individual", and "patient" are used interchangeably. None of the terms are to be interpreted as requiring the supervision of a medical professional (e.g., a doctor, nurse, physician's assistant, orderly, hospice worker). As used herein, the subject is any animal, including mammals (e.g., a human or non-human animal) and non-mammals. In one embodiment of the methods and compositions provided herein, the mammal is a human.

As used herein, the terms "treat," "treating" or "treatment," and other grammatical equivalents, include: alleviating, abating or ameliorating one or more symptoms of a disease or condition. In some embodiments, treating is alleviating, abating or ameliorating one or more symptoms of epithelial-mesenchymal transition. In some embodiments, treating is alleviating, abating or ameliorating one or more symptoms of proliferative vitreoretinopathy. In some embodiments, treating is alleviating, abating or ameliorating one or more symptoms of inflammation. In some embodiments, treating is preventing or reducing the appearance, severity or frequency of one or more additional symptoms of a disease or condition. In some embodiments, the methods include preventing or reducing the appearance, severity or frequency of one or more additional symptoms of epithelial-mesenchymal transition. In some embodiments, the methods include preventing or reducing the appearance, severity or frequency of one or more additional symptoms of proliferative vitreoretinopathy. In some embodiments, the methods include preventing or reducing the appearance, severity or frequency of one or more additional symptoms of inflammation. In some embodiments, the methods include ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically.

As used herein, "fetal support tissue" means tissue used to support the development of a fetus. Examples of fetal support tissue include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) amniotic stroma or substantially isolated amniotic stroma, (vi) placenta or substantially isolated placenta, (vii) umbilical cord or substantially isolated umbilical cord, (viii) amniotic fluid, or (ix) any combinations thereof. Fetal support tissue is also used interchangeably with "gestational tissue." In some embodiments the gestational tissue is "mammalian gestational tissue" or "human gestational tissue ("HGT")." In some embodiments, the fetal support tissue is obtained from a mammal. In some embodiments, the fetal support tissue is from human, non-human primate, cow, or pig. In some embodiments, the fetal support tissue is from human. In some embodiments, the fetal support tissue is ground, pulverized, morselized, a graft, a powder, a gel, a homogenate, or an extract. In some embodiments, the fetal support tissue is aseptically processed. In some embodiment, the fetal support tissue is terminally-sterilized.

As used herein, "placenta" means the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" means the membrane formed by extraembryonic mesoderm and the two layers of trophoblasts. The chorionic villi emerge from the chorion, invade the endometrium, and allow transfer of nutrients from the maternal blood to fetal blood. The chorion consists of two layers: an outer layer formed by the trophoblast, and an inner layer formed by the somatic mesoderm; the amnion is contact with the latter. The trophoblast is made up of an internal layer of cubical or prismatic cells, the cytotrophoblast or layer of Langhans, and an external layer of richly nucleated protoplasm devoid of cell boundaries, the syncytiotrophobast. The avascular amnion is adherent to the inner layer of the chorion.

As used herein, "amnion-chorion" means a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

As used herein, "umbilical cord" means the organ that connects a developing fetus to the placenta. The umbilical cord is composed of Wharton's jelly, a gelatinous substance made largely form mucopolysaccharides. It contains one vein, which carries oxygenated, nutrient-rich blood to the fetus, and two arteries that carry deoxygenated, nutrient-depleted blood away. In some embodiments, the blood vessels have been substantially removed from the umbilical cord tissue. In some embodiments, a portion of the Wharton's Jelly has been removed. In some embodiments, the blood vessels and a portion of the Wharton's Jelly have been removed.

As used herein, "placental amniotic membrane" (PAM) means amniotic membrane derived from the placenta. In some embodiments, the PAM is substantially isolated.

As used herein, "umbilical cord amniotic membrane" (UCAM) means amniotic membrane derived from the umbilical cord. UCAM is a translucent membrane. The UCAM has multiple layers: an epithelial layer; a basement membrane; a compact layer; a fibroblast layer; and a spongy layer. It lacks blood vessels or a direct blood supply. In some embodiments, the UCAM is substantially isolated. In some embodiments, the UCAM comprises all of the Wharton's Jelly. In some embodiments, the UCAM comprises a portion of the Wharton's Jelly. In some embodiments, the UCAM comprises blood vessels and/or arteries. In some embodiments, the UCAM comprises all of the Wharton's Jelly and blood vessels and/or arteries. In some embodiments, the UCAM comprises part of the Wharton's Jelly and blood vessels and/or arteries.

As used herein, "substantially isolated" or "isolated" means that the fetal support tissue product has been separate from undesired materials (e.g., red blood cells, blood vessels, and arteries) derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

As used herein, "biological activity" means the activity of polypeptides and polysaccharides. In some embodiments, the activity of polypeptides and polysaccharides found in umbilical cord (and substantially isolated umbilical cord), UCAM (and substantially isolated UCAM), placenta (and substantially isolated placenta), PAM (and substantially isolated PAM), chorion (and substantially isolated chorion), or amnion-chorion (and substantially isolated amnion-chorion). In some embodiments, the biological activity is anti-scarring activity, anti-inflammation activity, anti-angiogenic activity, and wound healing. In some embodiments, the biological activity is anti-inflammation activity. In some embodiments, the biological activity comprises the biological activity of a fetal support tissue preparation or composition. In some embodiments, the biological activity comprises the biological activity of HC-HA/PTX3.

As used herein, the substantial preservation of biological activity or structural integrity means that when compared to the biological activity and structural integrity of non-processed tissue, the biological activity and structural integrity of the fetal support tissue product has only decreased by about 5%, about 10%, about 15%, about 20%, about 25%, about 30%, about 35%, about 40%, about 50%, or about 60%.

As used herein, "freezing" refers to exposing the fetal support tissue product below about or at 0° C., −5° C., −10° C., −20° C., −40° C., −50° C., −60° C., −70° C., −80° C., −90° C., or −100° C. for a period of time of about 1 hour, 2 hours, 3 hours, 4 hours, 5 hours, 6 hours, 7 hours, 8 hours, 9 hours, 10 hours, 11 hours, 12 hours, 18 hours, 24 hours, or longer.

As used herein, "powder" means matter in the form of fine dry particles or matrix. In some embodiments, the particles are not uniform in size. In some embodiments, the particles are substantially uniform in size.

As used herein, "grinding" means any method of reducing fetal support tissue to small particles or a powder. The term grinding includes micronizing, pulverizing, homogenizing, filing, milling, grating, pounding, and crushing.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein, is an amount effective to achieve a desired effect or therapeutic improvement without undue adverse side effects. It is understood that "an effective amount" or "a therapeutically effective amount" can vary from individual to individual, due to variation in metabolism of the injectable composition, age, weight, general condition of the individual, the condition being treated, the severity of the condition being treated, and the judgment of the prescribing physician. In some embodiments, an effective amount is an amount that prevents or reduces the symptoms of PVR. In some embodiments, an effective amount is an amount that reduces, inhibits or prevents cell migration, cell proliferation and/or EMT of epithelial cells.

Epithelial-mesenchymal transition (EMT) is a process by which epithelial cells lose their cell polarity and cell-cell adhesion, and gain migratory and invasive properties. EMT occurs in processes such as mesoderm formation, neural tube formation, wound healing, as well as the initiation of metastasis for cancer progression. EMT can be induced through several signal signaling pathways, including TGF-β, FGF, EGF, HGF, Wnt/beta-catenin, and Notch.

Proliferative vitreoretinopathy (PVR) is a disease that develops as a complication of rhegmatogenous retinal detachment. When fluid from the vitreous humor enters a hole in the retina and accumulates in the subretinal space, the tractional force of the vitreous on the retina is what results in rhegmatogenous retinal detachment. During this process the retinal cell layers come in contact with vitreous cytokines, which can trigger the retinal pigmented epithelium (RPE) to proliferate and migrate. The RPE cells undergo epithelial-mesenchymal transition (EMT) and develop the ability to migrate out into the vitreous. During migration of the RPE, these cells lay down fibrotic membranes which contract and pull at the retina, and can lead to secondary retinal detachment after primary retinal detachment surgery.

Compositions

Disclosed herein, in certain embodiments, are compositions for preventing or reducing proliferation, cell migration, and/or epithelial-mesenchymal transition (EMT) of epithelial cells, comprising: a preparation of fetal support tissue; and a pharmaceutically acceptable diluent, excipient, vehicle, or carrier. Further disclosed herein, in certain embodiments, are injectable compositions for preventing or reducing proliferative venous retinopathy (PVR) in an individual in need thereof, comprising: a preparation of fetal support tissue; and a pharmaceutically acceptable diluent, excipient, vehicle, or carrier. Further disclosed herein, in certain embodiments, are injectable compositions for preventing or reducing proliferative venous retinopathy (PVR) in an individual in need thereof, consisting essentially of: substantially isolated HC-HA/PTX3, reconstituted HC-HA/PTX3 (rcHC-HA/PTX3); and a pharmaceutically acceptable diluent, excipient, vehicle, or carrier. Further disclosed herein, in certain embodiments, are injectable compositions for preventing or reducing proliferative venous retinopathy (PVR) in an individual in need thereof, consisting essentially of: substantially isolated HC-HA/PTX3, reconstituted HC-HA/PTX3 (rcHC-HA/PTX3); an additional therapeutic agent; and a pharmaceutically acceptable diluent, excipient, vehicle, or carrier.

In some embodiments, the preparation of fetal support tissue comprises HC-HA/PTX3. In some embodiments, the preparation of fetal support tissue comprises: high molecular weight hyaluronan (HA) that is cross-linked by a covalent bond to the heavy chain of inter-α-trypsin inhibitor (IαI), the high molecular weight HA having a molecular weight greater than 1000 kDa. In some embodiments, the preparation of fetal support tissue comprises: pentraxin 3 (PTX-3, PTX3). In some embodiments, the preparation of fetal support tissue comprises: tumor necrosis factor-stimulated gene 6 protein (TSG-6). In some embodiments, the preparation of fetal support tissue comprises: thrombospondin-1 (TSP-1). In some embodiments, the ratio of total protein to HA in the composition is less than 500 parts protein:1 part HA. In some embodiments, the ratio of HA to total protein in the composition is less than 500 parts HA:1 part protein. In some embodiments, the preparation of fetal support tissue comprises HC-HA/PTX3 complex. In some embodiments, the preparation of fetal support tissue comprises substantially purified HC-HA/PTX3 complex.

In some embodiments, the epithelial cells are human epithelial cells. In some embodiments, the human epithelial cells are retinal pigment epithelial cells (RPE). In some embodiments, the human epithelial cells are corneal epithelial cells. In some embodiments, the human epithelial cells are limbal epithelial cells. In some embodiments, the human epithelial cells are conjunctival epithelial cells. In some embodiments, the human epithelial cells are renal epithelial cells.

In some embodiments, the composition prevents the proliferation and EMT of epithelial cells by suppressing the activity of growth factors and cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF and IFN-γ. In some embodiments, the composition inhibits signaling pathways in epithelial cells to inhibit proliferation and EMT. In some embodiments, the signaling pathways are canonical Wnt signaling and TGF-β-induced Smad/ZEB signaling.

In some embodiments, the composition comprises the preparation of fetal support tissue and a pharmaceutically acceptable diluent, excipient, or carrier. In some embodiments, the composition further comprises an aqueous adjuvant. In some embodiments, the composition is for local administration. In some embodiments, the composition is formulated for injection. In some embodiments, the composition is formulated for intraocular injection, subretinal injection, intravitreal injection, periocular injection, subconjunctival injection, retrobulbar injection, intracameral injection or sub-Tenon's injection.

Preparations of Fetal Support Tissue

In some embodiments, the preparation of fetal support tissue comprises placental tissue, umbilical cord tissue, placental amniotic membrane tissue, chorion tissue, amniotic stroma, amnion-chorion tissue, UCAM tissue, amniotic fluid, or combinations thereof. In some embodiments, the preparation of fetal support tissue is an extract of fetal support tissue, micronized fetal support tissue, a homogenate of fetal support tissue, a powder of fetal support tissue, morselized fetal support tissue, pulverized fetal support tissue, ground fetal support tissue, purified HC-HA/PTX3, or a combination thereof. In some embodiments, the preparation of fetal support tissue is prepared from fresh, frozen or previously frozen fetal support tissue. In some embodiments, the preparation of fetal support tissue is prepared from frozen or previously frozen of fetal support tissue. In some embodiments, the preparation of fetal support tissue comprises HA, IαI, TSG-6, PTX-3, TSP-1, or a combination thereof. In some embodiments, the preparation of fetal support tissue comprises HC-HA/PTX3 complex. In some embodiments, the preparation of fetal support tissue comprises purified HC-HA/PTX3. In some embodiments, the preparation of fetal support tissue comprises ultracentrifuged HC-HA/PTX3. In some embodiments, the preparation of fetal support tissue consists of purified HC-HA/PTX3. In some embodiments, the preparation of fetal support tissue comprises reconstituted HC-HA/PTX3.

In some embodiments, the preparation of fetal support tissue suppresses TGF-β promoter activity; increases apoptosis in macrophages; decreases proliferation, decreases migration, and increases apoptosis of human vascular endothelial cells; decreases viability of human fibroblasts; decreases inflammation; and prevents apoptosis of epithelial cells exposed to storage and injury. In some embodiments, the preparations of fetal support tissue and injectable compositions described herein are used to treat diseases related to TGF-β upregulation, such as angiogenesis, wound healing, and tissue inflammation.

TGF-β is the prototypic cytokine that is involved in tissue inflammation, in addition to wound healing and scar formation. Mammalian cells express three different TGF-βs: TGF-β1, TGF-β2, and TGFβ3. TGF-β is the most potent cytokine promoting myofibroblast differentiation by up-regulating expression of α-SMA, integrin α5β1, and EDA domain-containing fibronectin (Fn) in a number of cell types, including fibroblasts. TGF-β also up-regulates the expression of such matrix components as collagens and proteoglycans, down-regulates proteinase and matrix metalloproteinases, and up-regulates their inhibitors. Collectively, these actions result in increased cell-matrix interactions and adhesiveness, as well as deposition and formation of scar tissue.

TGF-βs exert their actions via binding with TGF-β receptors (TGF-βRs) on the cell membrane. In human cells, there are three TGF-βRs, namely TGF-βR type I (TGF-βRI), type II (TGF-βRII), and type III (TGF-βRIII). TGF-βs, serving as ligands, bind with a serine, threonine kinase receptor complex made of TGF-βRI and TGF-βRII; such a binding is facilitated by TGF-βRIII, which is not a serine, threonine kinase receptor. Binding with TGF-βRII activates TGF-βRI, which is responsible for direct phosphorylation of a family of effector proteins known as Smads, which modulate transcription of a number of target genes, including those described herein, participating in scar formation.

Suppression of TGF-β can be achieved by neutralizing antibodies to TGF-β and agents that intercede the signaling mediated by TGF-β such as decorin. Most of the literature has shown suppression of TGF-β being achieved at the level of modulating the TGF-β activation, binding with its receptor, or its signal transduction. It has been shown that amniotic membrane can achieve such an inhibition at the level of transcription, i.e., to turn off transcription of TGF-β1 genes. In particular, amniotic membrane has been shown to suppress TGF-P signaling in human corneal and limbal fibroblasts, and human conjunctival and pterygium body fibroblasts.

Hyaluronic acid (HA) is a natural sugar found in the synovial joint fluid, the vitreous humor of the eye, the cartilage, blood vessels, extra-cellular matrix, skin, and umbilical cord. In some embodiments, the cross-linking of HA is through a covalent bond to another molecule, such as a protein. In some embodiments, HA is covalently bound to the heavy chain of inter-α-trypsin inhibitor (IαI). In some embodiments, the ratio of protein to HA in the preparation of fetal support tissue is less than about 500:1, less than about 200:1, less than about 100:1, less than about 50:1, or less than about 10:1 protein:HA. In some embodiments, the ratio of HA to protein in the preparation of fetal support tissue is less than about 500:1, less than about 200:1, less than about 100:1, less than about 50:1, or less than about 10:1 HA:protein.

TSG-6 is a hyaluronan binding protein that plays a role in extracellular matrix remodeling, cell proliferation, and leucocyte migration. TSG-6 can form a complex with the serine protease inhibitor inter-α-inhibitor (IαI) and catalyze the transfer of a heavy chain from IαI to HA. PTX-3 is Ca' dependent ligand binding protein that has a pentameric discoid structure and are present in plasma. TSP-1 (Thrombospondin 1) is a homotrimeric glycoprotein having a potent anti-angiogenic and other biological activities. TSP-1 is secreted into the extracellular matrix by a variety of cell types.

In some embodiments, the preparation of fetal support tissue comprises a purified component selected from HA, IαI, TSG-6, PTX-3, TSP-1, HC-HA/PTX3, or a combination thereof. In some embodiments the preparation of fetal support tissue comprises reconstituted HC-HA/PTX3. In some embodiments, the preparation of fetal support tissue comprises purified HC-HA/PTX3. In some embodiments, the preparation of fetal support tissue consists of HC-HA/PTX3. In some embodiments, the preparation of fetal support tissue comprises purified HC-HA/PTX3 at a high concentration. In some embodiments, the HC-HA/PTX3 is at a concentration of 25 to 750 µg/ml, 50 to 500 µg/ml, 50 to 250 µg/ml, or about 250 ug/ml, about 500 ug/ml, or about 750 ug/ml. In some embodiments, the purified component is obtained from any suitable source. In some embodiments, the purified component is obtained from a fetal support tissue. In some embodiments, the purified component of fetal support tissue is obtained from a commercial source. In some embodiments, the purified component of fetal support tissue is isolated from a transgenic organism. In some embodiments, a protein sequence of the purified component of fetal support tissue has a similarity of at least 90%, 93%, 95%, 97%, 99% or 99.5% to a human protein sequence. In some embodiments, the purified component of fetal support tissue is purified, substantially purified, partially purified, or are present in crude extracts. In some embodiments, the purified component of fetal support tissue is HC-HA/PTX3. In some embodiments, the purified component of fetal support tissue is isolated from the preparation of fetal support tissue at any time during the process.

In some embodiments, the preparation of fetal support tissue comprises Smad7. In some embodiments, Smad7 is obtained from any suitable source, such as from amniotic membrane, from a commercial source or isolated from a transgenic organism. In some embodiments, Smad7 is purified, substantially purified, partially purified, or is present in a crude extract.

In some embodiments, HA, IαI, TSG-6, PTX-3, TSP-1, and optionally Smad7 are obtained from the preparation of fetal support tissue. In some embodiments, the preparation of fetal support tissue containing the combination of HA, IαI, TSG-6, PTX-3, TSP-1 and optionally Smad7 is prepared.

In some embodiments, after homogenization of the fetal support tissue, is centrifuged to remove the insoluble material. In some embodiments, after homogenization of the fetal support tissue, the insoluble material is left in the preparation of fetal support tissue. In some embodiments, the preparation of fetal support tissue is dried. In some embodiments, a preparation of fetal support tissue is prepared according to a method described in Example 1.

In some embodiments, the fetal support tissue is obtained from sources such as Bio-Tissue, Inc. (Miami, Fla.) and Baptist Hospital (Miami, Fla.) (under IRB approval). In some embodiments, the fetal support tissue is obtained in either a fresh, frozen, or previously frozen state. In some embodiments, the fetal support tissue is washed to remove excess storage buffer, blood, or contaminants. In some embodiments, the excess liquid is removed using a brief centrifugation step, or by other means. In some embodiments, the fetal support tissue is frozen using liquid nitrogen or other cooling means to facilitate the subsequent homogenization. In some embodiments, the source of the fetal support tissue is a mammal. In some embodiments, the source of the fetal support tissue is a human. In some embodiments, other sources of fetal support tissue, such as non-human primate, bovine or porcine, are used.

In some embodiments, the preparation of fetal support tissue is obtained from AM jelly. In some embodiments, the AM jelly is obtained from fresh AM tissue. In some embodiments, AM jelly is obtained before freezing the fresh AM tissue. In some embodiments, AM jelly is obtained after freezing the fresh AM tissue. In some embodiments, AM jelly is obtained from frozen or previously frozen AM tissue. In some embodiments, the AM jelly is frozen. In some embodiments, the AM jelly is freeze-ground following the procedure for AM preparations as described herein. In some embodiments, the AM jelly is centrifuged. In some embodiments, the AM jelly is lyophilized.

In some embodiments, the preparation of fetal support tissue is made from a stroma of the AM. In some embodiments, the stroma is separated from a layer of fresh, frozen, thawed, or otherwise treated AM membrane. In some embodiments, the stroma removal occurs by enzymatic methods, mechanical methods, or by any other suitable means. In some embodiments, the stroma is fresh, frozen, or previously frozen. In some embodiments, the stroma is ground or freeze-ground following the procedure for generating the preparation of fetal support tissue from AM as described herein. In some embodiments, the stroma is centrifuged. In some embodiments, the stroma is lyophilized.

In some embodiment, the preparation is ground fetal support tissue. In some embodiments, the fetal support tissue is frozen prior to the grinding process. In some embodiments, the freezing step occurs by any suitable cooling process. In some embodiments, the fetal support tissue is flash-frozen using liquid nitrogen. In some embodiments, the fetal support tissue is placed in an isopropanol/dry ice bath or is flash-frozen in other coolants. In some embodiments, a commercially available quick freezing process is used. In some embodiments, the fetal support tissue is placed in a freezer and allowed to equilibrate to the storage temperature more slowly, rather than being flash-frozen. In some embodiments, the fetal support tissue is stored at any desired temperature. In some embodiments, the fetal support tissue is stored at −20° C. or −80° C.

In some embodiment, the preparation is pulverized fetal support tissue. In some embodiments, the fetal support tissue is pulverized while frozen. In some embodiments, fresh, partially thawed, or thawed fetal support tissue is used in the grinding step. In some embodiments, the fetal support tissue (fresh, frozen, or thawed) is sliced into pieces of a desired size with a suitable device, such as a scalpel, then ground to fine particles using a BioPulverizer (Biospec Products, Inc., Bartlesville, Okla.) or other suitable devices, and homogenized with a homogenization device such as a Tissue Tearor (Biospec Products, Inc., Dremel, Wis.), in a suitable solution, forming a homogenate. Non-limiting examples of solutions include, but are not limited to, phosphate buffered saline (PBS), DMEM, NaCl solution, and water. In some embodiments, the pH of the solution is adjusted as needed. In some embodiments, the pH range is from about 5.5 or 6.0 to about 8.5. In some embodiments, the frozen tissue is ground in a solution having a pH of between about 6.3 and about 7.8.

In some embodiment, the preparation is a homogenate of fetal support tissue. In some embodiments, the homogenate is mixed at any suitable speed, temperature, or other parameters. In some embodiments, the mixing occurs at a temperature range of from about 1° C., or 3° C., to about 6° C., 10° C., 15° C., or 20° C. In some embodiments, the mixing occurs at about 4° C. In some embodiments, the homogenate is mixed, for example, from less than about 1 minute, 10 minutes, or 20 minutes to about 1, 2, 3 or more hours.

In some embodiments, the homogenate is centrifuged to remove any remaining insoluble material and/or cellular debris. In some embodiments, the centrifugation is performed using any suitable range of time, temperature, protein concentration, buffers, and speed. In some embodiments, the centrifugation occurs at a range of about 1,000, 5,000, or 10,000×g to about 20,000×g. In some embodiments, the centrifugation occurs at about 15,000×g. In some embodiments, the centrifugation occurs for a duration of from less than 1 minute, 5 minutes, 10 minutes, 20 minutes, to about 40 minutes, 60 minutes, 1.5 hours, or more. In some embodiments, the supernatant is collected and stored in aliquots at −80° C. In some embodiments, the total protein is quantitated using any suitable commercial protein analysis kit, such as a BCA assay (Pierce, Rockford, Ill.). Example 2, Table 1 and FIG. 13 describe the analysis of AM preparations after low speed or high speed centrifugation.

In some embodiments, for biochemical characterization and purification, the above solutions are supplemented with protease inhibitors. An exemplary mixture of protease inhibitors is the following: 1 μg/ml aprotinin, 1 μg/ml leupeptin, 1 μg/ml pepstatin A, and 1 mM PMSF. In some embodiments, a protease inhibitor is not added to the preparation of fetal support tissue if the preparation of fetal support tissue is to be added to live cells or tissues.

In some embodiment, the preparation is an extract fetal support tissue. In some embodiments, any suitable buffer or liquid is used to prepare an extract of fetal support tissue. Example 2 examines the use of various extraction buffers (high salt, low salt, PBS, etc.) on total protein content and HA in the extract of fetal support tissue (Table 1). Example 2 examined the levels of the specific proteins TSG-6 (FIG. 14), PTX-3 (FIG. 18), TSP-1 (FIG. 19), and Smad7 (FIG. 20) using several extraction methods.

In some embodiments, the preparation of fetal support tissue is tested to confirm the presence of specific components or proteins. In some embodiments, the preparation of fetal support tissue is tested for the presence of molecules including, but not limited to, HA, IαI, TSG-6, PTX-3, TSP-1, and Smad7. In some embodiments, the preparation of fetal support tissue is tested to confirm the absence of pathogens at any point during the preparation process.

In some embodiments, the preparation of fetal support tissue is a dry powder. In some embodiments, the dry powder does not require refrigeration or freezing during storage to keep the dry powder from degrading over time. In some embodiments, the dry powder is stored and reconstituted prior to use. In some embodiments, the dry powder is prepared by preparing the freeze-ground fetal support tissue as described herein, then removing at least a portion of the water in the preparation of fetal support tissue. In some embodiments, the excess water is removed from the preparation of fetal support tissue by any suitable means. In some embodiments, is the excess water is removed by use of lyophilization. In some embodiments, lyophilizing the preparation of fetal support tissue comprises using a commercially available lyophilizer or freeze-dryer. In some embodiments, suitable equipment is found, for example, through Virtis (Gardiner, N.Y.); FTS Systems (Stone Ridge, N.Y.); and SpeedVac (Savant Instruments Inc., Farmingdale, N.Y.). In some embodiments, the amount of water that is removed is from about 5%, 10%, 20%, 30% to about 60, 70, 80, 90, 95 or 99% or more. In some embodiments, substantially all of the excess water is removed from the preparation of fetal support tissue. In some embodiments, the dry powder is stored. In some embodiments, the storage temperature varies from less than about −196° C., −80° C., −50°

C., or −20° C. to more than about 23° C. In some embodiments, the dry powder is characterized (weight, protein content, etc.) prior to storage.

In some embodiments, the dry powder is reconstituted in a suitable solution or buffer prior to use. Non-limiting examples of solutions include, but are not limited to, PBS, DMEM, and BSS. In some embodiments, the pH of the solution is adjusted as needed. In some embodiments, the dry powder is reconstituted with a sufficient volume of solution to produce a high concentration of the fetal support tissue reconstituted composition. In some embodiments, the dry powder is reconstituted with a sufficient volume of solution to produce a low concentration of the fetal support tissue reconstituted composition.

In some embodiments, the dry powder is reconstituted in a cream, ointment, gel, foam or lotion].

In some embodiments, the preparation of fetal support tissue is used to produce a phenotypic reversal of AMSCs from myofibroblasts to fibroblasts. In some embodiments, the preparation of fetal support tissue is used to prevent or slow differentiation of various cell types. In some embodiments, many types of cells are treated with the preparation of fetal support tissue.

Isolated nHC-HA/PTX3 Complexes

In some embodiments, the compositions include isolated native HC-HA/PTX3 complexes (nHC-HA/PTX3).

In some embodiments, the nHC-HA/PTX3 complexes are isolated from an isolated cell. In some embodiments, the nHC-HA/PTX3 complexes are isolated from a cultured cell. In some embodiments, the nHC-HA/PTX3 complexes are isolated from a stem cell. In some embodiments, the nHC-HA/PTX3 complexes are isolated from a water soluble fraction of an extract prepared from a tissue, such as umbilical cord or amniotic membrane. In some embodiments, the water soluble fraction is extracted with an isotonic salt solution. In some embodiments, the nHC-HA/PTX3 complexes are isolated from a water insoluble fraction of an extract prepared from a tissue, such as umbilical cord or amniotic membrane. In some embodiments, the insoluble fraction is extracted with GnHCl.

In some embodiments, the isolated nHC-HA/PTX3 complex is isolated from an amniotic tissue. In some embodiments, the isolated nHC-HA/PTX3 complex is isolated from an amniotic membrane or an umbilical cord. In some embodiments, the isolated nHC-HA/PTX3 complex is isolated from fresh, frozen or previously frozen placental amniotic membrane (PAM), fresh, frozen or previously frozen umbilical cord amniotic membrane (UCAM), fresh, frozen or previously frozen placenta, fresh, frozen or previously frozen umbilical cord, fresh, frozen or previously frozen chorion, fresh, frozen or previously frozen amnion-chorion, or any combinations thereof. Such tissues can be obtained from any mammal, such as, for example, but not limited to a human, non-human primate, cow or pig.

In some embodiments, the nHC-HA/PTX3 is purified by any suitable method. In some embodiments, the nHC-HA/PTX3 complex is purified by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the nHC-HA/PTX3 is isolated from an extract. In some embodiments, the extract is prepared from an amniotic membrane extract. In some embodiments, the extract is prepared from an umbilical cord extract. In some embodiments, the umbilical cord extract comprises umbilical cord stroma and/or Wharton's jelly. In some embodiments, the nHC-HA/PTX3 complex is contained in an extract that is prepared by ultracentrifugation. In some embodiments, the nHC-HA/PTX3 complex is contained in an extract that is prepared by ultracentrifugation using a CsCl/4-6M guanidine HCl gradient. In some embodiments, the extract is prepared by at least 2 rounds of ultracentrifugation. In some embodiments, the extract is prepared by more than 2 rounds of ultracentrifugation (i.e. nHC-HA/PTX3 2nd). In some embodiments, the extract is prepared by at least 4 rounds of ultracentrifugation (i.e. nHC-HA/PTX3 4th). In some embodiments, the nHC-HA/PTX3 complex comprises a small leucine-rich proteoglycan. In some embodiments, the nHC-HA/PTX3 complex comprises HC1, HA, PTX3 and/or a small leucine-rich proteoglycan.

In some embodiments, ultracentrifugation is performed on an extract prepared by extraction in an isotonic solution. In some embodiments, the isotonic solution is PBS. For example, in some embodiments the tissue is homogenized in PBS to produce a homogenized sample. The homogenized sample is then separated into a soluble portion and insoluble portion by centrifugation. In some embodiments, ultracentrifugation is performed on the soluble portion of the PBS-extracted tissue. In such embodiments, the nHC-HA/PTX3 purified by ultracentrifugation of the PBS-extracted tissue called an nHC-HA/PTX3 soluble complex. In some embodiments, the nHC-HA soluble complex comprises a small leucine-rich proteoglycan. In some embodiments, the nHC-HA/PTX3 soluble complex comprises HC1, HA, PTX3 and/or a small leucine-rich proteoglycan.

In some embodiments, ultracentrifugation is performed on an extract prepared by direct guanidine HCl extraction (e.g. 4-6 M GnHCl) of the amniotic membrane and/or umbilical cord tissue. In some embodiments, the GnHCl extract tissue is then centrifuged to produce GnHCl soluble and GnHCl insoluble portions. In some embodiments, ultracentrifugation is performed on the GnHCl soluble portion. In such embodiments, the nHC-HA/PTX3 purified by ultracentrifugation of the guanidine HCl-extracted tissue is called an nHC-HA/PTX3 insoluble complex. In some embodiments, the nHC-HA insoluble complex comprises a small leucine-rich proteoglycan. In some embodiments, the nHC-HA/PTX3 insoluble complex comprises HC1, HA, PTX3 and/or a small leucine-rich proteoglycan.

In some embodiments, ultracentrifugation is performed on an extract prepared by further guanidine HCl extraction of the insoluble portion of the PBS-extracted tissue. For example, in some embodiments the tissue is homogenized in PBS to produce a homogenized sample. The homogenized sample is then separated into a soluble portion and insoluble portion by centrifugation. The insoluble portion is then further extracted in guanidine HCl (e.g. 4-6 M GnHCl) and centrifuged to produce a guanidine HCl soluble and insoluble portions. In some embodiments, ultracentrifugation is performed on the guanidine HCl soluble portion. In such embodiments, the nHC-HA/PTX3 purified by ultracentrifugation of the guanidine HCl-extracted tissue is called an nHC-HA/PTX3 insoluble complex. In some embodiments, the nHC-HA insoluble complex comprises a small leucine-rich proteoglycan. In some embodiments, the nHC-HA/

PTX3 insoluble complex comprises HC1, HA, PTX3 and/or a small leucine-rich proteoglycan.

In some embodiments, the method of purifying the isolated nHC-HA/PTX3 extract comprises: (a) dissolving the isolated extract (e.g. prepared by the soluble or insoluble method described herein) in CsCl/4-6M guanidine HCl at the initial density of 1.35 g/ml, to generate a CsCl mixture, (b) centrifuging the CsCl mixture at 125,000×g for 48 h at 15° C., to generate a first purified extract, (c) extracting the first purified extract and dialyzing it against distilled water to remove CsCl and guanidine HCl, to generate a dialysate. In some embodiments, the method of purifying the isolated extract further comprises (d) mixing the dialysate with 3 volumes of 95% (v/v) ethanol containing 1.3% (w/v) potassium acetate at 0° C. for 1 h, to generate a first dialysate/ethanol mixture, (e) centrifuging the first dialysate/ethanol mixture at 15,000×g, to generate a second purified extract, and (f) extracting the second purified extract. In some embodiments, the method of purifying the isolated extract further comprises: (g) washing the second purified extract with ethanol (e.g., 70% ethanol), to generate a second purified extract/ethanol mixture; (h) centrifuging the second purified extract/ethanol mixture, to generate a third purified extract; and (i) extracting the third purified extract. In some embodiments, the method of purifying the isolated extract further comprises: (j) washing the third purified extract with ethanol (e.g., 70% ethanol), to generate a third purified extract/ethanol mixture; (k) centrifuging the third purified extract/ethanol mixture, to generate a forth purified extract; and (l) extracting the forth purified extract. In some embodiments, the purified extract comprises an nHC-HA/PTX3 complex.

In some embodiments, the nHC-HA/PTX3 complex is purified by immunoaffinity chromatography. In some embodiments, anti HC1 antibodies, anti-HC2 antibodies, or both are generated and affixed to a stationary support. In some embodiments, the unpurified HC-HA complex (i.e., the mobile phase) is passed over the support. In certain instances, the HC-HA complex binds to the antibodies (e.g., via interaction of (a) an anti-HC1 antibody and HC1, (b) an anti-HC2 antibody and HC2, (c) an anti-PTX antibody and PTX3, (d) an anti-SLRP antibody and the SLRP, or (e) any combination thereof). In some embodiments the support is washed (e.g., with PBS) to remove any unbound or loosely bound molecules. In some embodiments, the support is then washed with a solution that enables elution of the nHC-HA/PTX3 complex from the support (e.g., 1% SDS, 6M guanidine-HCl, or 8M urea).

In some embodiments, the nHC-HA/PTX3 complex is purified by affinity chromatography. In some embodiments, HABP is generated and affixed to a stationary support. In some embodiments, the unpurified nHC-HA/PTX3 complex (i.e., the mobile phase) is passed over the support. In certain instances, the nHC-HA/PTX3 complex binds to the HABP. In some embodiments the support is washed (e.g., with PBS) to remove any unbound or loosely bound molecules. In some embodiments, the support is then washed with a solution that enables elution of the HC-HA complex from the support.

In some embodiments, the nHC-HA/PTX3 complex is purified by a combination of HABP affinity chromatography, and immunoaffinity chromatography using anti HC1 antibodies, anti-HC2 antibodies, anti-PTX3 antibodies, antibodies against a SLRP or a combination of SLRPs, or any combination of antibodies thereof.

In some embodiments, the nHC-HA/PTX3 complex is purified from the insoluble fraction as described herein using one or more antibodies. In some embodiments, the nHC-HA/PTX3 complex is purified from the insoluble fraction as described herein using anti-SLRP antibodies.

In some embodiments, the nHC-HA/PTX3 complex is purified from the soluble fraction as described herein. In some embodiments, the nHC-HA/PTX3 complex is purified from the soluble fraction as described herein using anti-PTX3 antibodies.

In some embodiments, the nHC-HA/PTX3 complex comprises a small leucine rich proteoglycan (SLRP). In some embodiments, the nHC-HA/PTX3 complex comprises a class I, class II or class II SLRP. In some embodiments, the small leucine-rich proteoglycan is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the small leucine-rich proteoglycan is selected from among bikunin, decorin, biglycan, and osteoadherin. In some embodiments, the small leucine-rich protein comprises a glycosaminoglycan. In some embodiments, the small leucine-rich proteoglycan comprises keratan sulfate.

rcHC-HA/PTX3 Complexes

In some embodiments, the compositions comprise reconstituted HC-HA/PTX3 complexes (rcHC-HA/PTX3) with or without SLRPs.

In some embodiments, a method for generating reconstituted HC-HA/PTX3 complexes comprises (a) contacting immobilized high molecular weight hyaluronan (HMW HA) with pentraxin 3 (PTX3) under suitable conditions to form a PTX3/HA complex, and (b) contacting the PTX3/HA complex with IαI and Tumor necrosis factor-Stimulated Gene-6 (TSG-6). Provided herein are rcHC-HA/PTX3 complexes produced by such method. In some embodiments, TSG-6 catalyzes the transfer of heavy chain 1 (HC1) of inter-α-inhibitor (IαI) to HA. In some embodiments, HC1 of IαI forms a covalent linkage with HA. In some embodiments, the steps (a) and (b) of the method are performed sequentially in order.

In some embodiments, a method for generating reconstituted HC-HA/PTX3 complexes comprises contacting a PTX3/HA complex with IαI and TSG-6. In some embodiments, TSG-6 catalyzes the transfer of heavy chain 1 (HC1) of inter-α-inhibitor (IαI) to HA. Provided herein are rcHC-HA/PTX3 complexes produced by such method. In some embodiments, HC1 of IαI forms a covalent linkage with HA.

In some embodiments, a method for generating a complex of HA bound to PTX3 comprises contacting immobilized high molecular weight hyaluronan (HMW HA) with pentraxin 3 (PTX3) under suitable conditions to form a PTX3/HA complex. Provided herein are PTX3/HA complexes produced by such method.

In some embodiments, a method for generating reconstituted HC-HA/PTX3 complexes comprises (a) contacting immobilized high molecular weight hyaluronan (HMW HA) with IαI and TSG-6 to HA to form an HC-HA complex pre-bound to TSG-6 and (b) contacting the HC-HA complex with pentraxin 3 (PTX3) under suitable conditions to form an rcHC-HA/PTX3 complex. Provided herein are rcHC-HA/PTX3 complexes produced by such method. In some embodiments, HC1 of IαI forms a covalent linkage with HA. In some embodiments, the steps (a) and (b) of the method are performed sequentially in order. In some embodiments, the method comprises contacting an HC-HA complex pre-bound to TSG-6 with PTX3.

In some embodiments, the method comprises first contacting high molecular weight hyaluronan (HMW HA) with pentraxin 3 (PTX3) under suitable conditions to form a PTX3/HA complex, then contacting the PTX3/HA complex with IαI and TSG-6.

In some embodiments, the IαI protein and TSG-6 protein are contacted to the complex at a molar ratio of about 1:1, 2:1, 3:1, 4:1, 5:1, 6:1, 7:1, 8:1, 9:1, 10:1, 15:1, or 20:1 (IαI:TSG-6). In some embodiments the ratio of IαI:TSG-6 ranges from about 1:1 to about 20:1, such as about 1:1 to about 10:1, such as about 1:1 to 5 about:1, such as about 1:1 to about 3:1. In some embodiments, the ratio of IαI:TSG-6 is 3:1 or higher. In some embodiments, the ratio of IαI:TSG-6 is 3:1.

In some embodiments, the steps (a) and (b) of the method are performed sequentially in order. In some embodiments, the method comprises contacting a PTX3/HA complex with IαI and TSG-6.

In certain instances, TSG-6 interacts with IαI and forms covalent complexes with HC1 and HC2 of IαI (i.e. HC1.TSG-6 and HC2.TSG-6). In certain instances, in the presence of HA, the HCs are transferred to HA to form rcHC-HA. In some embodiments, a TSG-6.HC1 complex is added to pre-bound PTX3/HA complex to catalyze the transfer of HC1 to HA. In some embodiments, the method comprises first contacting immobilized high molecular weight hyaluronan (HMW HA) with pentraxin 3 (PTX3) under suitable conditions to form a PTX3/HA complex, then contacting the PTX3/HA complex with a HC1.TSG-6 complex. In some embodiments, a combination of HC1.TSG-6 complex and HC2.TSG-6 complex is added to a PTX3/HA complex.

In some embodiments, the step of contacting PTX3 to immobilized BMW HA occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments, the step of contacting PTX3 to immobilized BMW HA occurs for at least 2 hours or longer. In some embodiments, the step of contacting PTX3 to immobilized HMW HA occurs for at least 2 hours. In some embodiments, the step of contacting PTX3 to immobilized HMW HA occurs at 37° C. In some embodiments, the step of contacting PTX3 to immobilized HMW HA occurs in 5 mM MgCl$_2$ in PBS.

In some embodiments, the step of contacting the PTX3/HA complex with IαI and TSG-6 to HA occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the PTX3/HA complex with a HC1.TSG-6 complex and/or a HC2.TSG-6 complex occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the PTX3/HA complex with a HC1.TSG-6 complex and/or a HC2.TSG-6 complex occurs for at least 2 hours or longer. In some embodiments the step of contacting the PTX3/HA complex with a HC1.TSG-6 complex and/or a HC2.TSG-6 complex occurs for at least 2 hours. In some embodiments the step of contacting the PTX3/HA complex with a HC1.TSG-6 complex and/or a HC1.TSG-6 complex occurs at 37° C. In some embodiments the step of contacting the PTX3/HA complex with a HC1.TSG-6 complex and/or a HC1.TSG-6 complex occurs in 5 mM MgCl$_2$ in PBS.

In some embodiments, the method comprises contacting high molecular weight hyaluronan (HMW HA) with a pentraxin 3 (PTX3) protein, inter-α-inhibitor (IαI) protein comprising heavy chain 1 (HC1) and Tumor necrosis factor α-stimulated gene 6 (TSG-6) simultaneously under suitable conditions to form a HC-HA/PTX3 complex. In some embodiments, the contacting the BMW HA with PTX3, IαI and TSG-6 occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the HMW HA, PTX3, IαI, and TSG-6 occurs at 37° C. In some embodiments the step of contacting the HMW HA, PTX3, IαI, and TSG-6 occurs in 5 mM MgCl$_2$ in PBS.

In some embodiments, the method comprises contacting high molecular weight hyaluronan (HMW HA) with a pentraxin 3 (PTX3) protein, inter-α-inhibitor (IαI) protein comprising heavy chain 1 (HC1) and Tumor necrosis factor α-stimulated gene 6 (TSG-6) sequentially, in any order, under suitable conditions to form a HC-HA/PTX3 complex. In some embodiments, the contacting the HMW HA with PTX3, IαI and TSG-6 occurs for at least 10 minutes, at least 30 minutes, at least 1 hour, at least 2 hours, at least 3 hours, at least 4 hours, at least 5 hours, at least 6 hours, at least 12 hours, or at least 24 hours or longer. In some embodiments the step of contacting the HMW HA, PTX3, IαI, and TSG-6 occurs at 37° C. In some embodiments the step of contacting the HMW HA, PTX3, IαI, and TSG-6 occurs in 5 mM MgCl$_2$ in PBS.

In some embodiments, the methods for production of an rcHC-HA/PTX3 complex further comprises addition of one or more small leucine rich proteoglycans (SLRPs). In some embodiments, a method for generating reconstituted HC-HA/PTX3 complexes comprises (a) contacting immobilized high molecular weight hyaluronan (HMW HA) with pentraxin 3 (PTX3) under suitable conditions to form a PTX3/HA complex, (b) contacting the PTX3/HA complex with IαI and Tumor necrosis factor-Stimulated Gene-6 (TSG-6) and (c) contacting the PTX3/HA complex with one or more SLRPS. Provided herein are rcHC-HA/PTX3 complexes produced by such method. In some embodiments, TSG-6 catalyzes the transfer of heavy chain 1 (HC1) of inter-α-inhibitor (IαI) to HA. In some embodiments, HC1 of IαI forms a covalent linkage with HA. In some embodiments, the steps (a), (b), and (c) of the method are performed sequentially in order. In some embodiments, the steps (a), (b), and (c) of the method are performed simultaneously. In some embodiments, the step (a) of the method is performed and then steps (b) and (c) of the method are performed sequentially in order. In some embodiments, the step (a) of the method is performed and then steps (b) and (c) of the method are performed simultaneously.

In some embodiments, a method for generating reconstituted HC-HA/PTX3 complexes comprises (a) contacting immobilized high molecular weight hyaluronan (HMW HA) with IαI and TSG-6 to HA to form an HC-HA complex pre-bound to TSG-6, (b) contacting the HC-HA complex with pentraxin 3 (PTX3) and (c) contacting the HC-HA complex with one or more SLRPS under suitable conditions to form an rcHC-HA/PTX3 complex. Provided herein are rcHC-HA/PTX3 complexes produced by such method. In some embodiments, HC1 of IαI forms a covalent linkage with HA. In some embodiments, the method comprises contacting an HC-HA complex pre-bound to TSG-6 with PTX3. In some embodiments, the steps (a), (b), and (c) of the method are performed sequentially in order. In some embodiments, the steps (a), (b), and (c) of the method are performed simultaneously. In some embodiments, the step (a) of the method is performed and then steps (b) and (c) of the method are performed sequentially in order. In some embodiments, the step (a) of the method is performed and then steps (b) and (c) of the method are performed simultaneously.

In some embodiments, the SLRP is selected from among a class I, class II or class II SLRP. In some embodiments, the SLRP is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the small leucine-rich proteoglycan is selected from among bikunin, decorin, biglycan, and osteoadherin. In some embodiments, the small leucine-rich protein comprises a glycosaminoglycan. In some embodiments, the small leucine-rich proteoglycan comprises keratan sulfate.

PTX3

In some embodiments, PTX3 for use in the methods is isolated from a cell or a plurality of cells (e.g., a tissue extract). Exemplary cells suitable for the expression of PTX3 include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, PTX3 for use in the methods is isolated from a human cell. In some embodiments, PTX3 for use in the methods is isolated from a cell that is stimulated with one or more proinflammatory cytokines to upregulate PTX3 expression. In some embodiments, the proinflammatory cytokine is IL-1 or TNF-α.

In some embodiments, PTX3 for use in the methods is isolated from an amniotic membrane cell. In some embodiments, PTX3 for use in the methods is isolated from an amniotic membrane cell from an umbilical cord. In some embodiments, the amniotic membrane cell is stimulated with or more proinflammatory cytokines to upregulate PTX3 expression. In some embodiments, the proinflammatory cytokine is IL-1 or TNF-α.

In some embodiments, PTX3 for use in the methods is isolated from an umbilical cord cell. In some embodiments, the umbilical cord cell is stimulated with or more proinflammatory cytokines to upregulate PTX3 expression. In some embodiments, the proinflammatory cytokine is IL-1 or TNF-α.

In some embodiments, PTX3 for use in the methods is isolated from an amniotic epithelial cell. In some embodiments, PTX3 for use in the methods is isolated from an umbilical cord epithelial cell. In some embodiments, the amniotic epithelial cell or umbilical cord epithelial cell is stimulated with or more proinflammatory cytokines to upregulate PTX3 expression. In some embodiments, the proinflammatory cytokine is IL-1 or TNF-α.

In some embodiments, PTX3 for use in the methods is isolated from an amniotic stromal cell. In some embodiments, PTX3 for use in the methods is isolated from an umbilical cord stromal cell. In some embodiments, the amniotic stromal cell or umbilical cord stromal cell is stimulated with or more proinflammatory cytokines to upregulate PTX3 expression. In some embodiments, the proinflammatory cytokine is IL-1 or TNF-α.

In some embodiments, PTX3 for use in the methods is a native PTX3 protein isolated from a cell. In some embodiments, the cell is stimulated with or more proinflammatory cytokines to upregulate PTX3 expression. In some embodiments, the proinflammatory cytokine is IL-1 or TNF-α.

In some embodiments, PTX3 is prepared by recombinant technology. In some embodiments, PTX3 is expressed from a recombinant expression vector. In some embodiments, nucleic acid encoding PTX3 is operably linked to a constitutive promoter. In some embodiments, nucleic acid encoding PTX3 is operably linked to an inducible promoter. In some embodiments, PTX3 is expressed in a transgenic animal. In some embodiments, PTX3 is a recombinant protein. In some embodiments, PTX3 is a recombinant protein isolated from a cell. In some embodiments, PTX3 is a recombinant protein produced in a cell-free extract.

In some embodiments, PTX3 is purified from amniotic membrane, umbilical cord, umbilical cord amniotic membrane, chorionic membrane, amniotic fluid, or a combination thereof. In some embodiments, PTX3 is purified from amniotic membrane cells. In some embodiments, the amniotic membrane cell is an amniotic epithelial cell. In some embodiments, the amniotic membrane cell is an umbilical cord epithelial cell. In some embodiments, the amniotic membrane cell is an amniotic stromal cell. In some embodiments, the amniotic membrane cell is an umbilical cord stromal cell. In some embodiments, the amniotic membrane cell is stimulated with or more proinflammatory cytokines to upregulate PTX3 expression. In some embodiments, the proinflammatory cytokine is IL-1 or TNF-α.

In some embodiments, PTX3 is not isolated from a cell or a plurality of cells (e.g., a tissue extract).

In some embodiments, PTX3 comprises a polypeptide having the sequence set forth in SEQ ID NO: 33 or a variant thereof having at least 65%, 70%, 75%, 80%, 85%, 90%, 95%, 96%, 97%, 98%, or 99% sequence amino acid identity to the polypeptide having the sequence set forth in SEQ ID NO: 33. Exemplary variants include, for example, species variants, allelic variants and variants that contain conservative and non-conservative amino acid mutations. In some embodiments, PTX3 comprises a fragment of PTX3 sufficient to bind to HA and facilitate the formation of rcHC-HA/PTX3 complex. In some embodiments, PTX3 comprises Glu18 to Ser277 of human PTX3. Variants of PTX3 for use in the provided methods include variants with an amino acid modification that is an amino acid replacement (substitution), deletion or insertion. In some embodiments, such modification improves one or more properties of the PTX3 polypeptides such as improving the one or more therapeutic properties of the rcHC-HA/PTX3 complex (e.g., anti-inflammatory, anti-immune, anti-angiogenic, anti-scarring, anti-adhesion, regeneration or other therapeutic activities as described herein).

In some embodiments PTX3 protein is obtained from a commercial source. An exemplary commercial source for PTX3 is, but is not limited to, PTX3 (Catalog No. 1826-TS; R&D Systems, Minneapolis, Minn.).

In some embodiments, the PTX3 protein used in the methods is a multimeric protein. In some embodiments, the PTX3 protein used in the methods is a homomultimer. In some embodiments, the homomultimer is a dimer, trimer, tetramer, hexamer, pentamer, or octamer. In some embodiments, the PTX3 homomultimer is a trimer, tetramer, or octamer. In particular embodiments, the PTX3 homomultimer is an octamer. In some embodiments, the multimerization domain is modified to improve multimerization of the PTX3 protein. In some embodiments, the multimerization domain is replaced with a heterogeneous multimerization domain (e.g., an Fc multimerization domain or leucine zipper) that when fused to PTX3 improves the multimerization of PTX3.

TSG-6

In some embodiments, TSG-6 for use in the methods is isolated from a cell or a plurality of cells (e.g., a tissue extract). Exemplary cells suitable for the expression of TSG-6 include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, TSG-6 for use in the methods is isolated from a human cell. In some embodiments, TSG-6 for use in the methods is isolated from a cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic membrane cell. In some embodiments, TSG-6 for use in the methods is isolated from an amniotic membrane cell from an umbilical cord. In some embodiments, TSG-6 for use in the methods is isolated from an amniotic membrane cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an umbilical cord cell. In some embodiments, TSG-6 for use in the methods is isolated from an umbilical cord cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic epithelial cell. In some embodiments, TSG-6 for use in the methods is isolated from an umbilical cord epithelial cell. In some embodiments, TSG-6 for use in the methods is isolated from an amniotic epithelial cell or an umbilical cord epithelial cell that is stimulated with one or more proinflammatory cytokines to upregulate TSG-6 expression. In some embodiments, the proinflammatory cytokine is IL-1 or TNF-α.

In some embodiments, TSG-6 for use in the methods is isolated from an amniotic stromal cell. In some embodiments TSG-6 for use in the methods is isolated from an umbilical cord stromal cell. In some embodiments, TSG-6 for use in the methods is isolated from an amniotic stromal cell or an umbilical cord stromal cell that is stimulated with one or more proinflammatory cytokines to upregulate TSG-6 expression. In some embodiments, the proinflammatory cytokine is IL-1 or TNF-α.

In some embodiments, TSG-6 for use in the methods is a native TSG-6 protein isolated from a cell. In some embodiments, the cell is stimulated with or more proinflammatory cytokines to upregulate TSG-6 expression. In some embodiments, the proinflammatory cytokine is IL-1 or TNF-α.

In some embodiments, TSG-6 is prepared by recombinant technology. In some embodiments, TSG-6 is expressed from a recombinant expression vector. In some embodiments, nucleic acid encoding TSG-6 is operably linked to a constitutive promoter. In some embodiments, nucleic acid encoding TSG-6 is operably linked to an inducible promoter. In some embodiments, TSG-6 is expressed in a transgenic animal. In some embodiments, TSG-6 is a recombinant protein. In some embodiments, TSG-6 is a recombinant protein isolated from a cell. In some embodiments, TSG-6 is a recombinant protein produced in a cell-free extract.

In some embodiments, TSG-6 is purified from amniotic membrane, amniotic membrane, chorionic membrane, amniotic fluid, or a combination thereof. In some embodiments, PTX3 is purified from amniotic membrane cells. In some embodiments, the amniotic membrane cell is an amniotic epithelial cell. In some embodiments, the amniotic epithelial cell is an umbilical cord epithelial cell. In some embodiments, the amniotic membrane cell is an amniotic stromal cell. In some embodiments, the amniotic membrane cell is an umbilical cord stromal cell. In some embodiments, the amniotic membrane cell is stimulated with or more proinflammatory cytokines to upregulate TSG-6 expression. In some embodiments, the proinflammatory cytokine is IL-1 or TNF-α.

In some embodiments, TSG-6 is not isolated from a cell or a plurality of cells (e.g., a tissue extract).

In some embodiments, TSG-6 comprises a fragment of TSG-6 that is sufficient to facilitate or catalyze the transfer HC1 of IαI to HA. In some embodiments, TSG-6 comprises the link module of TSG-6. In some embodiments, TSG-6 comprises amino acids Trp18 through Leu277 of TSG-6. In some embodiments, TSG-6 comprises a polypeptide having the sequence set forth in SEQ ID NO: 2 or a variant thereof having at least 65%, 70%, 75%, 80%, 85%, 90%, 95%, 96%, 97%, 98%, or 99% sequence amino acid identity to the polypeptide having the sequence set forth in SEQ ID NO: 2. Exemplary variants include, for example, species variants, allelic variants and variants that contain conservative and non-conservative amino acid mutations. Natural allelic variants of human TSG-6 include, for example, TSG-6 containing the amino acid replacement Q144R. Variants of TSG-6 or HA binding fragments thereof for use in the provided methods include variants with an amino acid modification that is an amino acid replacement (substitution), deletion or insertion. In some embodiments, such modification improve one or more properties of the TSG-6 polypeptides such as improved transfer of HC1 of IαI to HA or improved release of the TSG-6 polypeptide from the rcHC-HA/PTX3 complex following transfer of HC1 of IαI to HA.

In some embodiments, TSG-6 comprises an affinity tag. Exemplary affinity tags include but are not limited to a hemagglutinin tag, a poly-histidine tag, a myc tag, a FLAG tag, a glutathione-S-transferase (GST) tag. Such affinity tags are well known in the art for use in purification. In some embodiments, such an affinity tag incorporated into the TSG-6 polypeptide as a fusion protein or via a chemical linker. In some embodiments, TSG-6 comprises an affinity tag and the unbound TSG-6 is removed from the rcHC-HA/PTX3 complex by affinity purification.

In some embodiments TSG-6 protein is obtained from a commercial source. An exemplary commercial source for TSG-6 is, but is not limited to, TSG-6 (Catalog No. 2104-TS R&D Systems, Minneapolis, Minn.).

IαI

In some embodiments, the IαI comprises an HC1 chain. In some embodiments, the IαI comprises an HC1 and an HC2 chain. In some embodiments, the IαI comprises an HC1 and bikunin. In some embodiments, the IαI comprises an HC1, and HC2 chain and bikunin. In some embodiments, the IαI comprises an HC1, and HC2 chain and bikunin linked by a chondroitin sulfate chain.

In some embodiments, IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the IαI is purified from human blood, plasma or serum. In some embodiments, IαI is isolated from human serum. In some embodiments, IαI is not isolated from serum. In some embodiments, IαI for use in the methods is produced in an amniotic membrane cell. In some embodiments, IαI for use in the methods is produced in an umbilical cord cell. In some embodiments, IαI for use in the methods is produced in an amniotic membrane cell from an umbilical cord. In some embodiments, IαI for use in the methods is produced in an amniotic epithelial cell. In some embodiments, IαI for use in the methods is produced in an umbilical cord epithelial cell. In some embodiments, IαI for use in the methods is produced in an amniotic stromal cell. In some embodiments, IαI for use in the methods is produced in an umbilical cord stromal cell. In some embodiments, IαI for use in the methods is produced in a hepatic cell. In some embodiments, IαI is prepared by recombinant technology.

In some embodiments, HC1 of IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the HC1 of IαI is purified from human blood, plasma or serum. In some embodiments, IαI is isolated from human serum. In some embodiments, HC1 of IαI is not purified from serum. In some embodiments, HC1 of IαI is prepared by recombinant technology. In some embodiments, HC1 of IαI is purified from hepatic cells. In some embodiments, HC1 of IαI is purified from amniotic membrane cells. In some embodiments, HC1 of IαI is purified from amniotic epithelial cells or umbilical cord epithelial cells. In some embodiments, HC1 of IαI is purified from amniotic stromal cells or umbilical cord stromal cells.

In some embodiments, HC1 comprises a polypeptide having the sequence set forth in SEQ ID NO: 47 or a polypeptide having at least 75%, 80%, 85%, 90%, 95%, 96%, 97%, 98%, or 99% sequence amino acid identity to the polypeptide having the sequence set forth in SEQ ID NO: 47.

In some embodiments, HC2 of IαI is isolated from a biological sample. In some embodiments the biological sample is a biological sample from a mammal. In some embodiments, the mammal is a human. In some embodiments, the biological sample is a blood, serum, plasma, liver, amniotic membrane, chorionic membrane or amniotic fluid sample. In some embodiments, the biological sample is a blood, serum, or plasma sample. In some embodiments, the biological sample is a blood sample. In some embodiments, the biological sample is a serum sample. In some embodiments, the biological sample is a plasma sample. In some embodiments, the HC2 of IαI is purified from human blood, plasma or serum. In some embodiments, HC2 of IαI is isolated from human serum. In some embodiments, HC2 of IαI is isolated from human serum. In some embodiments, HC2 of IαI is not isolated from blood serum. In some embodiments, HC2 of IαI is prepared by recombinant technology. In some embodiments, HC2 of IαI is purified from hepatic cells. In some embodiments, HC2 of IαI is purified from amniotic membrane cells. In some embodiments, HC2 of IαI is purified from amniotic epithelial cells or umbilical cord epithelial cells. In some embodiments, HC2 of IαI is purified from amniotic stromal cells or umbilical cord stromal cells.

In some embodiments, HC2 comprises a polypeptide having the sequence set forth in SEQ ID NO: 49 or a polypeptide having at least 75%, 80%, 85%, 90%, 95%, 96%, 97%, 98%, or 99% sequence amino acid identity to the polypeptide having the sequence set forth in SEQ ID NO: 49.

In some embodiments, IαI comprises bikunin. In some embodiments, bikunin comprises a polypeptide having the sequence set forth in SEQ ID NO: 53 or a polypeptide having at least 75%, 80%, 85%, 90%, 95%, 96%, 97%, 98%, or 99% sequence amino acid identity to the polypeptide having the sequence set forth in SEQ ID NO: 53. In some embodiments, IαI comprises a chondroitin sulfate chain.

HA

In some embodiments, HA is purified from a cell, tissue or a fluid sample. In some embodiments, HA is obtained from a commercial supplier (e.g., Sigma Aldrich or Advanced Medical Optics, Irvine, Calif. (e.g., Healon)). In some embodiments, HA is obtained from a commercial supplier as a powder. In some embodiments, HA is expressed in a cell. Exemplary cells suitable for the expression of HA include, but are not limited to, animal cells including, but not limited to, mammalian cells, primate cells, human cells, rodent cells, insect cells, bacteria, and yeast, and plant cells, including, but not limited to, algae, angiosperms, gymnosperms, pteridophytes and bryophytes. In some embodiments, HA is expressed in a human cell. In some embodiments, HA is expressed in a transgenic animal. In some embodiments, HA is obtained from a cell that expresses a hyaluronan synthase (e.g., HAS1, HAS2, and HAS3). In some embodiments, the cell contains a recombinant expression vector that expresses an HA synthase. In certain instances, an HA synthase lengthens hyaluronan by repeatedly adding glucuronic acid and N-acetylglucosamine to the nascent polysaccharide as it is extruded through the cell membrane into the extracellular space.

HA for use in the methods is typically high molecular weight (HMW) HA. In some embodiments, the weight average molecular weight of HMW HA is greater than about 500 kilodaltons (kDa), such as, for example, between about 500 kDa and about 10,000 kDa, between about 800 kDa and about 8,500 kDa, between about 1100 kDa and about 5,000 kDa, or between about 1400 kDa and about 3,500 kDa. In some embodiments, the weight average molecular weight of HMW HA is about 3000 kDa.

Additional Components

In some embodiments, one or more additional components are added to generate an rcHC-HA/PTX3 complex. In some embodiments, a small leucine rich proteoglycan (SLRP) is added to generate an rcHC-HA/PTX3 complex. In some embodiments, the SLRP is a class I, class II or class II SLRP. In some embodiments, the SLRP is selected from among class I SLRPs, such as decorin and biglycan. In some embodiments, the SLRP is selected from among class II SLRPs, such as fibromodulin, lumican, PRELP (proline arginine rich end leucine-rich protein), keratocan, and osteoadherin. In some embodiments, the SLRP is selected from among class III SLRPs, such as epipycan and osteoglycin. In some embodiments, the SLRP is selected from among bikunin, decorin, biglycan, and osteoadherin. In some embodiments, the SLRP comprises a glycosaminoglycan. In some embodiments, the SLRP comprises keratan sulfate.

HA Immobilization

In some embodiments, HMW HA is immobilized by any suitable method. In some embodiments, HMW HA is immobilized to a solid support, such as culture dish, bead, a column or other suitable surfaces, such as, for example, a surface of an implantable medical device or a portion thereof or on a surface that is subsequently connected to or combined with an implantable medical device as described herein. In some embodiments, HMW HA is immobilized directly to the solid support, such a by chemical linkage. In some embodiments, HMW HA is attached indirectly to the solid support via a linker or an intermediary protein. Numerous heterobifunctional cross-linking reagents that are used to form covalent bonds between amino groups and thiol groups and to introduce thiol groups into proteins, are known to those of skill in this art. In some embodiments, HMW HA is immobilized directly to the solid support via crosslinking to the solid support. In some embodiments, HMW HA is immobilized directly to the solid support without crosslinking to the solid support. In some embodiments, BMW HA is immobilized directly to the solid support as a coating. In some embodiments, HMW HA is immobilized to a Covalink™-NH surface. In some embodiments, HMW HA is immobilized directly to the solid support as a coating. In some embodiments, HMW HA is immobilized to a Covalink™-NH surface for about 16 h at 4° C.

In some embodiments, the method comprises immobilizing HMW HA to a solid surface via direct linkage to a solid support (i.e. without an intermediary protein). In some embodiments, the solid support is washed to remove unbound BMW HA prior to contacting the immobilized HA with PTX3. In some embodiments, the solid support is washed with washes of 8M GnHCl and PBS to remove unbound HMW HA prior to contacting the immobilized HA with PTX3.

In some embodiments, the method comprises immobilizing HA to a solid surface via an intermediary protein or a linker. In some embodiments, the linker is a peptide linker. In some embodiments, the intermediary protein is an HA binding protein (HABP). In some embodiments, HABP is first attached to a solid support (e.g., by cross-linking, chemical linkage or via a chemical linker). In some embodiments, the solid support comprising HABP is then contacted with HA (e.g., HMW HA) to immobilize HA to the solid support via binding of the HABP to HA. In some embodiments, the solid support is washed to remove unbound HMW HA prior to contacting the immobilized HMW HA with PTX3. In some embodiments, the solid support is washed with washes of 8M GnHCl and PBS to remove unbound BMW HA prior to contacting the immobilized HA with PTX3.

In some embodiments, the method comprises immobilizing HA to a solid surface via attachment of a peptide linker to the solid support and attachment HA to the peptide linker. In some embodiments, the peptide linker comprises a protease cleavage site.

In some embodiments, the method comprises immobilizing HA to a solid surface via attachment of a cleavable chemical linker, such as, but not limited to a disulfide chemical linker.

In some embodiments, the HABP selected for use in the methods is an HABP that is dissociated from HA following formation of the rcHC-HA/PTX3 complex. In some embodiments, the HABP non-covalently binds to HA. In some embodiments, the method further comprises dissociating the rcHC-HA/PTX3 complex from HABP using one or more dissociating agents. Dissociating agents for the disruption of non-covalent interactions (e.g., guanidine hydrochloride, urea and various detergents, e.g., SDS) are known in the art. In some embodiments the dissociating agent is urea. In some embodiments the dissociating agent is guanidine hydrochloride. In some embodiments, the dissociation agent is about 4M to about 8M guanidine-HC1. In some embodiments, the dissociation agent is about 4M, about 5M, about 6M, about 7M, about 8M guanidine-HC1. In some embodiments, the dissociation agent is about 4M to about 8M guanidine-HC1 in PBS at pH 7.5.

In some embodiments, such dissociating agents are employed to dissociate the rcHC-HA/PTX3 complex from an intermediary HABP. An HABP for use in the methods typically is selected such that the binding affinity for HA is strong enough to permit assembly of the rcHC-HA/PTX3 complex but is dissociated from the rcHC-HA/PTX3 complex with a suitable dissociation agent. In some embodiments the dissociating agent is guanidine hydrochloride.

Exemplary HABPs for use with the methods provided herein include, but are not limited to, HAPLN1, HAPLN2, HAPLN3, HAPLN4, aggrecan, versican, neurocan, brevican, phosphacan, TSG-6, CD44, stabilin-1, stabilin-2, or portions thereof (e.g., link modules thereof) sufficient to bind HA. In some embodiments, the HABP comprises a polypeptide having the sequence set forth in any of SEQ ID NOS: 54-99 or a polypeptide having at least 75%, 80%, 85%, 90%, 95%, 96%, 97%, 98%, or 99% sequence amino acid identity to the polypeptide having the sequence set forth in any of SEQ ID NOS: 54-99. In some embodiments, the HABP is versican. In some embodiments, the HABP is a recombinant protein. In some embodiments, the HABP is a recombinant mammalian protein. In some embodiments, the HABP is a recombinant human protein. In some embodiments, the HABP is a recombinant versican protein or a portion thereof sufficient to bind to HA. In some embodiments, the HABP is a recombinant aggrecan protein or a portion thereof sufficient to bind to HA. In some embodiments, the HABP is a native HABP or a portion thereof sufficient to bind to HA. In some embodiments, the native HABP is isolated from mammalian tissue or cells. In some embodiments, the HABP is isolated from bovine nasal cartilage (e.g. HABP from Seikagaku which contains the HA binding domains of aggrecan and link protein).

In some embodiments, the HABP comprises a link module of HAPLN1, HAPLN2, HAPLN3, HAPLN4, aggrecan, versican, neurocan, brevican, phosphacan, TSG-6, CD44, stabilin-1, or stabilin-2. In some embodiments, the HABP comprising a link module comprises a polypeptide having the sequence set forth in any of link domains of SEQ ID NOS: 54-99 or a polypeptide having at least 75%, 80%, 85%, 90%, 95%, 96%, 97%, 98%, or 99% sequence amino acid identity to the polypeptide having the sequence set forth in any of link domains of SEQ ID NOS: 54-99. In some embodiments, the HABP comprises a link module of versican. In some embodiments, the HABP comprising a link module is a recombinant protein. In some embodiments, the HABP comprising a link module of versican is a recombinant protein.

In some embodiments, the or intermediary protein, such as an HABP, contains a proteolytic cleavage sequence that is recognized by and is hydrolyzed by a site specific protease, such as furin, 3C protease, caspase, matrix metalloproteinase or TEV protease. In such embodiments, assembled rcHC-HA/PTX3 complexes are released from the solid support by contacting the immobilized complexes with a protease that cleaves the specific cleavage sequence.

In some embodiments, the rcHC-HA/PTX3 complex is purified. In some embodiments, the rcHC-HA/PTX3 complex is purified by any suitable method or combination of methods. The embodiments described below are not intended to be exclusive, only exemplary.

In some embodiments, the rcHC-HA/PTX3 complex is purified by chromatography (e.g., ion exchange, affinity, size exclusion, and hydroxyapatite chromatography), gel filtration, centrifugation (e.g., gradient centrifugation), or differential solubility, ethanol precipitation or by any other available technique for the purification of proteins.

In some embodiments, the rcHC-HA/PTX3 complex is purified by immunoaffinity chromatography. In some embodiments antibodies are generated against a component of the rcHC-HA/PTX3 complex (e.g., anti-HC1, anti-PTX, an antibody against one or more SLRPs of the rcHC-HA/PTX3 complex, e.g., anti-bikunin, anti-decorin, anti-biglycan, or anti-osteoadherin) and affixed to a solid support. In some embodiments, the unpurified rcHC-HA/PTX3 complex (i.e., the mobile phase) is passed over the support. In certain instances, the rcHC-HA/PTX3 complex binds to the antibodies. In some embodiments, the support is washed (e.g., with PBS) to remove any unbound or loosely bound molecules. In some embodiments, the support is then washed with a solution that enables elution of the rcHC-HA/PTX3 complex from the support (e.g., 1% SDS, 6M guanidine-HC1, or 8M urea). In some embodiments, the dissociating agent is removed from the dissociated rcHC-HA/PTX3 complex. In some embodiments, the dissociating agent is removed from the dissociated rcHC-HA/PTX3 complex by a method including, but not limited to, ion-exchange chromatography, dialysis, gel filtration chromatography, ultrafiltration, or diafiltration.

In some embodiments, the rcHC-HA/PTX3 complex is purified by affinity chromatography. In some embodiments, an HABP is employed to bind to the rcHC-HA/PTX3 complex for purification of the complex and affixed to a stationary support. In some embodiments, the unpurified rcHC-HA/PTX3 complex (i.e., the mobile phase) is passed over the support. In certain instances, the rcHC-HA/PTX3 complex binds to the HABP. In some embodiments the support is washed (e.g., with PBS) to remove any unbound or loosely bound molecules. In some embodiments, the support is then washed with a solution (e.g., a dissociating agent) that enables elution of the rcHC-HA/PTX3 complex from the support. In some embodiments, the dissociating agent is removed from the dissociated rcHC-HA/PTX3 complex by a method including, but not limited to, ion-exchange chromatography, dialysis, gel filtration chromatography, ultrafiltration, or diafiltration.

In some embodiments, the rcHC-HA/PTX3 complex is purified by a combination of HABP affinity chromatography, and immunoaffinity chromatography using antibodies against one or more components of the rcHC-HA/PTX3 complex.

In some embodiments, one or more components of the rcHC-HA/PTX3 complex disclosed herein comprise an affinity tag (e.g., a fusion protein of PTX3 or HC1 with an affinity tag). Exemplary affinity tags that are incorporated into one or more components of the rcHC-HA/PTX3 complex in some embodiments include, but are not limited to, a hemagglutinin tag, poly-histidine, a myc tag, a FLAG tag, or glutathione-S-transferase sequence. In some embodiments, the ligand for the affinity tag is affixed to the solid support. In some embodiments, the unpurified rcHC-HA/PTX3 complex is passed over the support. In certain instances, the rcHC-HA/PTX3 complex binds to the ligand. In some embodiments the support is washed (e.g., with PBS) to remove any unbound or loosely bound molecules. In some embodiments, the support is then washed with a solution that enables elution of an rcHC-HA/PTX3 complex disclosed herein from the support. In some embodiments, the elution agent is removed from the dissociated rcHC-HA/PTX3 complex by a method including, but not limited to, ion-exchange chromatography, dialysis, gel filtration chromatography, ultrafiltration, or diafiltration.

In some embodiments, the PTX3, TSG-6, and/or HC1 are conjugated to a label. A "label" refers to a detectable compound or composition which is conjugated directly or indirectly to a polypeptide so as to generate a labeled polypeptide. In some embodiments, the label is detectable by itself (e.g., radioisotope labels or fluorescent labels) or, in the case of an enzymatic label, catalyzes chemical alteration of a substrate compound composition which is detectable. Non-limiting examples of labels include fluorogenic moieties, dyes, fluorescent tags, green fluorescent protein, or luciferase.

Excipients

In some embodiments, the compositions comprise excipients. In some embodiments, the excipient is chosen from the group comprising pH modifiers, buffers, collagen, HA, antibiotics, surfactants, stabilizers, proteins, and combinations thereof. In some embodiments, excipient comprises an extracellular matrix (ECM) component. In some embodiments, the ECM component comprises collagen, fibrin, HA, or a combination thereof.

Collagen is a major structural protein found in the body. It provides support for tissues, connects tissue to bone, and provides the structure of the body. When the body is in the healing process, collagen plays a role in helping to build a cellular structure. Hyaluronic acid is a natural sugar found in the synovial joint fluid, the vitreous humor of the eye, the cartilage, blood vessels, extra-cellular matrix, skin, and umbilical cord. Fibrin is a protein involved in the clotting of blood.

In some embodiments, the preparation of fetal support tissue is mixed with collagen, fibrin or HA. Collagen, fibrin and HA can be suitable delivery vehicles, as AM preparations mixed with collagen or HA were shown to exert a suppressive effect upon TGF 13 promoter activity. Although the preparations of fetal support tissue were mixed with collagen gel and HA gel in the experiments described herein, in some embodiments, any soluble form (e.g., liquid) of collagen and HA or other ECM components (e.g., fibrin) is used. In some embodiments, the collagen, fibrin or HA is derived from any suitable source. In some embodiments, the ratio of AM to collagen, fibrin or HA is varied. In some embodiments, the ratio of AM to collagen, fibrin, or HA is less than about 0.001:1, 0.01:1, 0.05:1, or 0.1:1, to about 1:1, 1.5:1, 2:1, 5:1, 10:1, 100:1 or 1000:1 or more is used.

In some embodiments, collagen gel is prepared by diluting the stock solution (4 mg/ml) with 0.1 N acetic acid and by mixing it with appropriate volume ratios of 20× of DMEM or suitable buffer, and 1 N NaOH, as described in Example 1. In some embodiments, the collagen in the composition is present at a range of from less than about 2 mg/ml to more than about 4 mg/ml.

In some embodiments, the HA is a high molecular weight (MW) HA. In some embodiments, various dilutions of high MW HA are prepared by diluting commercially prepared HA (Healon™ (10 mg HA/nil) (Pharmacia, La Jolla, Calif.) in DMEM or suitable buffer. In some embodiments, dry powder and water-soluble forms of the preparation of fetal support tissue are diluted in a solution such as PBS, DMEM, or other solutions into the desired collagen concentration. In some embodiments, the HA in the preparation of fetal support tissue is present at a range of from less than about 2 µg/ml to more than about 129 µg/ml.

Illustrative Preparations

Examples 8 through 15 represent illustrative methods for preparing the preparations of fetal support tissue described and used herein.

Compositions

In some embodiments, the composition comprising the preparation of fetal support tissue is formulated for administration purposes as a non-solid dosage form. In some embodiments, the non-solid dosage form comprises combining the preparation with a delivery vehicle to create a composition such as a solution, drop, suspension, paste, spray, ointment, oil, emulsion, aerosol, coated bandage, patch, cream, lotion, gel, and the like. The formulation used will depend upon the particular application. Gels are useful for administering the composition because they allow better retention of the active ingredient at the site of introduction, allowing the active ingredient to exert its effect for a longer period of time before clearance of the active ingredient. In some embodiments, the composition is formulated as extended-release solid dosage forms (including oral dosage forms).

In some embodiments, the composition is formulated in a conventional manner using one or more physiologically acceptable carriers including excipients and auxiliaries which facilitate processing of preparation of fetal support tissue into compositions which are used pharmaceutically. Proper formulation is dependent upon the route of administration chosen. Any of the well-known techniques, carriers, and excipients may be used as suitable and as understood in the art.

In some embodiments, the composition of fetal support tissue is in a liquid, suspension, a gel, or lyophilized powder, or other forms. In some embodiments, the composition is injectable. In some embodiments, the composition of fetal support tissue comprises an antimicrobial agent. In some embodiments, the antimicrobial agent is an antibiotic or anti-fungal agent. In some embodiments, the composition of fetal support tissue comprises an additional substance to stabilize and/or preserve the composition of fetal support tissue. In some embodiments, the composition of fetal support tissue is packaged and stored at room temperature, −20° C. or −80° C. prior to use.

In certain embodiments, the composition comprises a pharmaceutically acceptable diluent, excipient, or carrier. In some embodiments, the composition further comprises other active ingredients, as in combination therapy. In some embodiments, the composition comprises other medicinal or pharmaceutical agents, carriers, adjuvants, such as preserving, stabilizing, wetting or emulsifying agents, solution promoters, and salts for regulating the osmotic pressure, buffers, or a combination thereof. In some embodiments, the composition comprises an additional therapeutic agent.

In some embodiments, the composition further comprises a chemical component, such as a carrier, stabilizer, diluent, dispersing agent, suspending agent, thickening agent, excipient, or a combination thereof. In some embodiments, the composition facilitates administration of the preparation to the individual. In some embodiments, a therapeutically effective amount of the composition of fetal support tissue is administered as an injectable composition to an individual having a disease, disorder, or condition to be treated. In some embodiments, the individual is a mammal. In some embodiments, the mammal is a human. In some embodiments, the therapeutically effective amount varies depending on the severity of the disease, the age and relative health of the individual, the potency of the composition used and other factors. In some embodiments, the composition is used singly or in combination with one or more therapeutic agents as components of mixtures.

Ophthalmic Compositions:

In some embodiments, the ophthalmic compositions comprise a preparation of a fetal support tissue; and a pharmaceutically acceptable diluent, excipient, vehicle, or carrier. In some embodiments, the ophthalmic compositions consist essentially of substantially isolated HC-HA/PTX3, reconstituted HC-HA/PTX3, or a combination thereof and a pharmaceutically acceptable diluent, excipient, vehicle, or carrier. In some embodiments, the composition is prepared for local delivery to the eye. In some embodiments, the composition is administered systemically, such as intravenously. In some embodiments, the composition is administered topically to the eye. In some embodiments, the composition is formulated into a variety of topically administrable ophthalmic compositions. In some embodiments, the topically administrable ophthalmic composition comprises a solution, suspension, gel or ointment. In some embodiments, the composition is formulated for injection into the eye. In some embodiments, the composition is administered by intravitreal injection into the eye. In some embodiments, the composition is administered by intraocular injection, subretinal injection, intravitreal injection, periocular administration, subconjunctival injections, retrobulbar injections, intracameral injections (including into the anterior or vitreous chamber), or sub-Tenon's injections. In some embodiments, the composition is administered by implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the fornix).

In some embodiments, the composition is a liquid composition where the preparation of fetal support tissue is present in solution, in suspension or both. In some embodiments, the composition includes a gel formulation. In other embodiments, the liquid composition is aqueous. In some embodiments, the composition is an ointment.

In some embodiments, the composition is an aqueous composition. In some embodiments, the aqueous composition is an aqueous solution, suspension or solution/suspension. In some embodiments, the aqueous composition is presented in the form of eye drops. In some embodiments, a desired dosage is administered via a known number of drops into the eye. For example, for a drop volume of 25 administration of 1-6 drops will deliver 25-150 µl of the composition. In some embodiments, the aqueous composition comprises from about 0.01% to about 50% weight/volume of the preparation of fetal support tissue or purified component. In some embodiments, the aqueous composition comprises from about 0.1% to about 20% weight/volume of the preparation of fetal support tissue or purified component. In some embodiments, the aqueous composition comprises from about 0.2% to about 10% weight/volume of the preparation of fetal support tissue or purified component. In some embodiments, the aqueous composition comprises from about 0.5% to about 5%, weight/volume of the preparation of fetal support tissue or purified component. In some embodiments, the aqueous composition has an ophthalmically acceptable pH and osmolality. "Ophthalmically acceptable" with respect to a formulation, composition or ingredient typically means having no persistent detrimental effect on the treated eye or the functioning thereof, or on the general health of the subject being treated. Transient effects such as minor irritation or a "stinging" sensation are common with topical ophthalmic administration of agents and consistent with the formulation, composition or ingredient in question being "ophthalmically acceptable."

In some embodiments, the composition is an aqueous composition and comprises a polymer as a suspending agent. In some embodiments, the aqueous composition comprises more than one polymer as the suspending agent. In some embodiments, the polymer comprises a water-soluble polymer, a water-insoluble polymer, or a combination thereof. In some embodiments, the water-soluble polymer comprises a cellulosic polymer. In some embodiments, the cellulosic polymer comprises hydroxypropyl methylcellulose. In some embodiments, the water-insoluble polymer comprises a cross-linked carboxyl-containing polymer. In some embodiments, the aqueous composition comprises an ophthalmically acceptable mucoadhesive polymer. In some embodiments, the mucoadhesive polymer comprises carboxymethylcellulose, carbomer (acrylic acid polymer), poly (methylmethacrylate), polyacrylamide, polycarbophil, acrylic acid/butyl acrylate copolymer, sodium alginate, dextran, or a combination thereof.

In some embodiments, the composition comprises an ophthalmically acceptable solubilizing agent to aid in the solubility of the preparation of fetal support tissue in the composition. In some embodiments, the composition comprises an ophthalmically acceptable solubilizing agent to aid in the solubility of purified HC-HA/PTX3 in the composition. The term "solubilizing agent" generally includes agents that result in formation of a micellar solution or a true solution of the agent. In some embodiments, the ophthalmically acceptable solubilizing agent is a nonionic surfactants. In some embodiments, the nonionic surfactant comprises polysorbate 80, glycol, polyglycol, polyethylene glycol 400, glycol ethers, derivatives thereof, or any combination thereof.

In some embodiments, the composition comprises one or more ophthalmically acceptable pH adjusting agents or buffering agents. In some embodiments, the pH adjusting agent comprises an acid. In some embodiments, the acid is chosen from a list comprising: acetic, boric, citric, lactic, phosphoric acid, and hydrochloric acid. In some embodiments, the pH adjusting agent comprises a base. In some embodiments, the base is chosen from a list comprising: sodium hydroxide, sodium phosphate, sodium borate, sodium citrate, sodium acetate, sodium lactate and tris-hydroxymethylaminomethane. In some embodiments, the buffering agent is chosen from a list comprising: citrate/dextrose, sodium bicarbonate, and ammonium chloride. In some embodiments, the acid, the base or the buffers are included in an amount required to maintain pH of the composition in an ophthalmically acceptable range.

In some embodiments, the composition comprises an ophthalmically acceptable salt in an amount required to bring osmolality of the composition into an ophthalmically acceptable range. In some embodiments, the salt comprises sodium, potassium or ammonium cations and chloride, citrate, ascorbate, borate, phosphate, bicarbonate, sulfate, thiosulfate or bisulfite anions. In some embodiments, the salt is chosen from a list comprising: sodium chloride, potassium chloride, sodium thiosulfate, sodium bisulfite, ammonium sulfate, or a combination thereof.

In some embodiments, the composition comprises an ophthalmically acceptable preservative to inhibit microbial activity. In some embodiments, the preservative comprises a mercury-containing substance, stabilized chlorine dioxide, a quaternary ammonium compound, or a combination thereof. In some embodiments, the mercury-containing substance comprises merfen, thiomersal, or a combination thereof. In some embodiments, the quaternary ammonium compound comprises benzalkonium chloride, cetyltrimethylammonium bromide, cetylpyridinium chloride, or a combination thereof.

In some embodiments, the composition comprises one or more ophthalmically acceptable surfactants to enhance physical stability or for other purposes. In some embodiments, the surfactant comprises a nonionic surfactant. In some embodiments, the nonionic surfactant is chosen from a list comprising: polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the composition comprises one or more antioxidants to enhance chemical stability where required. In some embodiments, the antioxidant comprises ascorbic acid, sodium metabisulfite, or a combination thereof.

In some embodiments, the composition is packaged in single-dose non-reclosable containers. In some embodiments, the composition is packaged in a multiple-dose reclosable container. In some embodiments, the composition further comprises a preservative when packaged in the multiple-dose reclosable container.

In some embodiments, the composition is in the form of a solid article that is inserted between the eye and eyelid or in the conjunctival sac, where it releases the preparation. In some embodiments, the preparation is released to the lacrimal fluid that bathes the surface of the cornea, or directly to the cornea itself, with which the solid article is generally in intimate contact. In some embodiments, the solid article suitable for implantation in the eye comprises polymers. In some embodiments, the solid article suitable for implantation in the eye is biodegradable or non-biodegradable.

Injectable Compositions:

In some embodiments, the composition is an injectable composition. In some embodiments, the injectable compositions comprise a preparation of a fetal support tissue; and a pharmaceutically acceptable diluent, excipient, vehicle, or carrier. In some embodiments, the injectable compositions consist essentially of substantially isolated HC-HA/PTX3, reconstituted HC-HA/PTX3, or a combination thereof; and a pharmaceutically acceptable diluent, excipient, vehicle, or carrier. In some embodiments, the injectable composition is suitable for intraocular, intramuscular, subcutaneous, or intravenous injection. In some embodiments, the injectable composition comprises physiologically acceptable sterile aqueous or non-aqueous solutions, dispersions, suspensions or emulsions, and sterile powders for reconstitution into sterile injectable solutions or dispersions. Non-limiting examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. In some embodiments, proper fluidity is maintained by the use of a coating, a surfactant, or a combination thereof. In some embodiments, the coating is lecithin. In some embodiments, the injectable composition comprises an additive. In some embodiments, the additive is chosen from the list comprising: a preserving agent, a wetting agent, an emulsifying agent, a dispensing agent, or a combination thereof. In some embodiments, the injectable composition comprises an antibacterial or antifungal agent. In some embodiments, the antibacterial or antifungal agent is comprises a paraben, chlorobutanol, phenol, sorbic acid, or a combination thereof. In some embodiments, the injectable composition comprises an isotonic agent. In some embodiments, the isotonic agent comprises sugar, sodium chloride, or a combination thereof. In some embodiments, the injectable composition comprises an absorption delaying agent. In some embodiments, the absorption delaying agent comprises aluminum monostearate gelatin, or a combination thereof.

In some embodiments, the injectable composition is administered intravenously. In some embodiments, the injectable composition is formulated in an aqueous solution, in a physiologically compatible buffer such as Hank's solution, Ringer's solution, a physiological saline buffer, or another suitable solution. In some embodiments, for transmucosal administration, a penetrant appropriate to the barrier to be permeated is used in the formulation. Such penetrants are generally known in the art. In some embodiments, for a parenteral injection, an appropriate formulation includes aqueous or nonaqueous solutions, preferably with physiologically compatible buffers or excipients. Such excipients are generally known in the art.

In some embodiments, parenteral injections involve bolus injection or continuous infusion. In some embodiments, the composition is presented in unit dosage form, e.g., in ampoules or in multi dose containers, with an added preservative. In some embodiments, the injectable composition is in a formulation suitable for parenteral injection as a sterile suspensions, solutions or emulsions in oily or aqueous vehicles. In some embodiments, the injectable composition comprises a formulary agent. In some embodiments, the formulary agent is a suspending agent, stabilizing agent, dispersing agent, or a combination thereof. In some embodiments, the injectable composition for parenteral administration comprises the aqueous solution of preparation of fetal support tissue in water soluble form. In some embodiments, the suspension of the active compounds is prepared as an oily injection suspension. In some embodiments, the injectable composition comprises a lipophilic solvent or vehicle. Non-limiting examples of lipophilic solvents or vehicles include, but are not limited to, fatty oils such as sesame oil, or synthetic fatty acid esters, such as ethyl oleate or triglycerides, or liposomes. In some embodiments, the injectable injection composition contains a substance which increases the viscosity of the suspension, such as sodium carboxymethyl cellulose, sorbitol, or dextran. In some embodiments, the injectable composition contains suitable stabilizers or agents which increase the solubility of the compounds to allow for the preparation of highly concentrated solutions. In some embodiments, the preparation of fetal support tissue is in powder form for constitution with a suitable vehicle, e.g., sterile pyrogen-free water, before use.

Methods of Dosing and Treatments Regimens:

In some embodiments, the composition is administered by any suitable technique. In some embodiments, composition is administered directly to a target site (e.g., ocular surface, vitreous, etc.). In some embodiments, the composition is administered topically. In some embodiments, the composition is administered parentally (e.g., subcutaneous). In some embodiments, composition is administered intraocularly.

In some embodiments, the composition is administered for prophylactic and/or therapeutic applications. In some embodiments, the composition is administered to an individual already suffering from a disease or condition, in an amount sufficient to cure or at least partially arrest the symptoms of the disease or condition. In some embodiments, amounts effective for this use depend on the severity and course of the disease or condition, previous therapy, the individual's health status, weight, and response to the drugs, and the judgment of the treating physician.

In some embodiments, the composition is administered to an individual susceptible to or otherwise at risk of a particular disease, disorder or condition. Such an amount is defined to be a "prophylactically effective amount or dose." In this use, the precise amounts also depend on the individual's state of health, weight, and the like. In some embodiments, a dose escalation trial is used to determine a prophylactically effective amount. In some embodiments, any suitable method is used to determine the prophylactically effective amount. In some embodiments, the prophylactically effective amount depends on the severity and course of the disease, disorder or condition, previous therapy, the individual's health status and response to the drugs, and the judgment of the treating physician.

In the case wherein the individual's condition does not improve, upon the doctor's discretion the composition is administered chronically, that is, for an extended period of time, including throughout the duration of the individual's life in order to ameliorate or otherwise control or limit the symptoms of the individual's disease or condition.

In the case wherein the individual's status does improve, upon the doctor's discretion the composition is given continuously or the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some embodiments, the dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the individual's conditions has occurred, a maintenance dose is administered if necessary. Subsequently, the dosage or the frequency of administration, or both, is reduced, as a function of the symptoms, to a level at which the improved disease, disorder or condition is retained. In some embodiments, the individual requires intermittent treatment on a long-term basis upon any recurrence of symptoms.

In some embodiments, the amount of the composition administered to the individual varies depending upon factors such as the disease or condition and its severity, the identity (e.g., weight, gender, age, overall health) of the individual in need of treatment. In some embodiments, the amount of composition administered is determined in a manner known in the art according to the particular circumstances surrounding the case, including, e.g., the specific preparation, composition, or formulation being administered, the route of administration, the condition being treated, and the individual being treated. In some embodiments, the amounts or doses employed for adult human treatment are in the range of 0.02-5000 mg per day, preferably 1-1500 mg per day. In some embodiments, a desired dose is presented in a single dose or as divided doses administered simultaneously (or over a short period of time) or at appropriate intervals, for example as two, three, four or more sub-doses per day.

In some embodiments, the composition is in unit dosage forms suitable for single administration of precise amounts or dosages. In unit dosage form, the composition is divided into unit doses containing appropriate amounts or doses of the composition. In some embodiments, the unit dosage is in the form of a package containing discrete quantities of the composition. Non-limiting examples are powders packaged in vials or ampoules. In some embodiments, compositions are packaged in single-dose non-reclosable containers. In some embodiments, multiple-dose reclosable containers are used, in which case it is typical to include a preservative in the composition. In some embodiments, the composition for parenteral injection are presented in unit dosage form, which include, but are not limited to ampoules, or in multi-dose containers, with an added preservative.

In some embodiments, the daily dosage appropriate for the composition is from about 0.01 to 2.5 mg/kg per body weight. An indicated daily dosage is in the range from about 0.5 mg to about 100 mg, conveniently administered in divided doses, including, but not limited to, up to four times a day or in extended release form. The foregoing ranges are merely suggestive, as the number of variables in regard to an individual treatment regime is large, and considerable excursions from these recommended values are not uncommon. In some embodiments, the dosage is altered depending on a number of variables, not limited to the activity of the composition, the disease or condition to be treated, the mode of administration, the requirements of the individual, the severity of the disease or condition being treated, and the judgment of the practitioner.

In some embodiments, the toxicity and therapeutic efficacy of such therapeutic regimens is determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). In some embodiments, the dose ratio between the toxic and therapeutic effects is the therapeutic index and is expressed as the ratio between $LD_{50}$ and $ED_{50}$. Compositions exhibiting high therapeutic indices are preferred. In some embodiments, data obtained from a cell culture assay or animal study is used in formulating a range of dosage for use in the individual. In some embodiments, the dosage of the composition is within a range of circulating concentrations that include the $ED_{50}$ with minimal toxicity. In some embodiments, the dosage varies within this range depending upon the dosage form employed and the route of administration utilized.

Combination Treatments:

In some embodiments, the composition is co-administered with an additional therapeutic compound. In some embodiments, the additional therapeutic agent is not administered in the same composition. In some embodiments, the additional therapeutic agent is administered by a different route than the composition. The determination of the mode of administration and the advisability of administration, where possible, in the same composition, is well within the knowledge of the skilled clinician. In some embodiments, the initial administration is made according to established protocols known in the art, and then modified by the skilled clinician based upon the observed effects, the dosage, modes of administration and times of administration.

In some embodiments, the particular choice of the additional therapeutic compound used depends upon the diagnosis of the attending physicians and their judgment of the condition of the individual and the appropriate treatment protocol. In some embodiments, the additional therapeutic compound is administered concurrently (e.g., simultaneously, essentially simultaneously or within the same treatment protocol) or sequentially, depending upon the nature of the disease, disorder, or condition, the condition of the individual, and the actual choice of compounds used. The determination of the order of administration, and the number of repetitions of administration of each therapeutic agent during a treatment protocol, is well within the knowledge of the skilled physician after evaluation of the disease being treated and the condition of the individual.

In some embodiments, a therapeutically-effective dosage varies when the composition is used in a combination treatment. In some embodiments, any suitable method is used to determine a therapeutically effective dosage of a drug and other agents for use in the combination treatment regimens. In some embodiments, metronomic dosing (i.e., providing more frequent, lower doses in order to minimize toxic side effects) is used to determine a therapeutically effective dosage of a drug and other agents for use in the combination treatment. In some embodiments, the combination treatment comprises periodic treatments that start and stop at various times to assist with the clinical management of the individual.

In some embodiments, dosage of the additional therapeutic agent varies depending on the type of co-drug employed, on the specific drug employed, on the disease or condition being treated and so forth. In some embodiments, when co-administered with one or more additional therapeutic agents, the composition is administered either simultaneously with the additional therapeutic agent, or sequentially. If administered sequentially, the attending physician will decide on the appropriate sequence of administering the composition in combination with the additional therapeutic agent.

In some embodiments, multiple additional therapeutic agents are administered in combination with the composition. In some embodiments, the multiple additional therapeutic agents are administered in any order or even simultaneously. If simultaneously, the multiple additional therapeutic agents are provided in a single, unified form, or in multiple forms (by way of example only, either as a single pill or as two separate pills). In some embodiments, one of the additional therapeutic agents is given in multiple doses, or both may be given as multiple doses. In some embodiments, if administration is not simultaneous, the timing between the multiple doses varies from more than zero weeks to less than four weeks.

In some embodiments, the dosage regimen to treat, prevent, or ameliorate the condition(s) for which relief is sought, is modified in accordance with a variety of factors. In some embodiments, the factors comprise: a disorder from which the individual suffers, as well as the age, weight, sex, diet, and medical condition of the individual, or a combination thereof. In some embodiments, the dosage regimen varies widely and deviates from the dosage regimens set forth herein.

In some embodiments, the composition and additional therapeutic agent which make up the combination therapy are a combined dosage form or in separate dosage forms intended for substantially simultaneous administration. In some embodiments, the composition and additional therapeutic agent that make up the combination therapy are administered sequentially, with either the composition or the additional therapeutic agent being administered by a regimen calling for two-step administration. In some embodiments, the two-step administration regimen calls for sequential administration of the composition and additional therapeutic agent or spaced-apart administration of the composition and additional therapeutic agent. In some embodiments, the time period between the multiple administration steps ranges from, a few minutes to several hours, depending upon the properties of each pharmaceutical agent, such as potency, solubility, bioavailability, plasma half-life and kinetic profile of the composition or additional therapeutic agent. In some embodiments, circadian variation of the composition or therapeutic agent concentration determines the optimal dose interval.

In some embodiments, the composition is used in combination with procedures that may provide additional or synergistic benefit to the individual. By way of example only, individuals are expected to find therapeutic and/or prophylactic benefit in the methods described herein, wherein the composition or the composition in combination with the additional therapeutic agent is combined with genetic testing to determine whether that individual is a carrier of a mutant gene that is known to be correlated with certain diseases or conditions.

In some embodiments, the composition and combination therapies are administered before, during or after the occurrence of a disease or condition, and the timing of administering the composition containing a compound varies. In some embodiments, the composition is used as a prophylactic and administered continuously to individuals with a propensity to develop conditions or diseases in order to prevent the occurrence of the disease or condition. In some embodiments, the composition is administered to the individual during or as soon as possible after the onset of the symptoms. In some embodiments, the administration of the composition is initiated within the first 48 hours of the onset of the symptoms, preferably within the first 48 hours of the onset of the symptoms, more preferably within the first 6 hours of the onset of the symptoms, and most preferably within 3 hours of the onset of the symptoms. In some embodiments, the initial administration is via any route practical, such as, for example, an intravenous injection, a bolus injection, infusion over 5 minutes to about 5 hours, and the like, or combination thereof. In some embodiments, the composition is administered as soon as is practicable after the onset of a disease or condition is detected or suspected, and for a length of time necessary for the treatment of the disease, such as, for example, from about 1 month to about 3 months. In some embodiments, the length of treatment varies for each individual, and the length is determined using the known criteria. In some embodiments, the composition is administered for at least 2 weeks, preferably about 1 month to about 5 years, and more preferably from about 1 month to about 3 years.

Methods of Treatment:

Disclosed herein, in certain embodiments, are methods for preventing or reducing proliferation, cell migration, and/or EMT of epithelial cells in an individual in need thereof, comprising administering to the individual a therapeutically effective amount of an injectable composition, comprising: (a) a preparation of a fetal support tissue; and (b) a pharmaceutically acceptable diluent, excipient, vehicle, or carrier, thereby preventing or reducing the proliferation, cell migration, and/or EMT of epithelial cells. In some embodiments, the EMT is associated with a disease other than PVR.

Disclosed herein, in certain embodiments, are methods for treating or preventing of Proliferative Vitreoretinopathy (PVR) in an individual in need thereof, comprising administering to the individual a therapeutically effective amount of an injectable composition, comprising: (a) a preparation of fetal support tissue; and (b) a pharmaceutically acceptable diluent, excipient, vehicle, or carrier, thereby treating or preventing PVR.

In some embodiments, the preparation of fetal support tissue comprises HC-HA/PTX3. In some embodiments, the preparation of fetal support tissue comprises purified HC-HA/PTX3. In some embodiments, the preparation of fetal support tissue comprises ultracentrifuged HC-HA/PTX3. In some embodiments, the preparation of fetal support tissue consists of purified HC-HA/PTX3. In some embodiments, the preparation of fetal support tissue comprises reconstituted HC-HA/PTX3. In some embodiments, the preparation of fetal support tissue comprises: high molecular weight hyaluronan (HA) that is cross-linked by a covalent bond to the heavy chain of inter-α-trypsin inhibitor (IαI), the high molecular weight HA having a molecular weight greater than 1000 kDa. In some embodiments, the preparation comprises: pentraxin 3 (PTX-3). In some embodiments, the preparation of fetal support tissue comprises: tumor necrosis factor-stimulated gene 6 protein (TSG-6). In some embodiments, the preparation of fetal support tissue comprises: thrombospondin-1 (TSP-1). In some embodiments, the ratio of total protein to HA in the composition is less than 500 parts protein:1 part HA. In some embodiments, the ratio of HA to total protein in the compositions is less than 500 parts HA:1 part protein.

In some embodiments, the epithelial cells are human epithelial cells. In some embodiments, the human epithelial cells are retinal pigment epithelial cells (RPE). In some embodiments, the human epithelial cells are renal epithelial cells. In some embodiments, the human epithelial cells are corneal epithelial cells. In some embodiments, the human epithelial cells are limbal epithelial cells. In some embodiments, the human epithelial cells are conjunctival epithelial cells.

In some embodiments, the composition prevents the proliferation and EMT of epithelial cells by inhibiting or suppressing the activity of growth factors or cytokines. In some embodiments, the growth factors and cytokines are selected from the group consisting of: EGF, FGF-2, PDGF-A, PDGF-AB, PDGF-B, PDGF-C, TGF-β1, TGF-β2, TGF-β3, CTGF, HGF, IGF-1, G-CSF, IL-6, MCP-1, TNF-α, VEGF and IFN-γ. In some embodiments, the composition inhibits signaling pathways in epithelial cells to inhibit proliferation and EMT. In some embodiments, the signaling pathways are canonical Wnt signaling and TGF-β-induced Smad/ZEB signaling.

In some embodiments, the compositions comprise a preparation of fetal support tissue prepared from placental tissue, umbilical cord tissue, umbilical cord amniotic membrane tissue, placental amniotic membrane tissue, amniotic stromal tissue, amnion-chorion tissue, chorion tissue, amniotic fluid, or combinations thereof. In some embodiments, the placental tissue, umbilical cord tissue, amniotic membrane tissue, chorion tissue or combinations thereof is homogenized, pulverized or ground. In some embodiments, the placental tissue, umbilical cord tissue, amniotic membrane tissue, chorion tissue or combinations thereof is fresh, frozen or has been previously frozen. In some embodiments, a composition comprises the preparation of fetal support tissue and a pharmaceutically acceptable diluent, excipient, or carrier. In some embodiments, the composition further comprises an aqueous adjuvant. In some embodiments, the composition is for local administration. In some embodiments, the composition is for injection. In some embodiments, the composition is formulated for intraocular injection, subretinal injection, intravitreal injection, periocular injection, subconjunctival injection, retrobulbar injection, intracameral injection or sub-Tenon's injection.

The methods disclosed herein have many uses including research and clinical applications. In some embodiments, the methods are applied to tissues or cells to achieve a desired modulation of physiology. In some embodiments, the methods are used on cell cultures or tissue cultures to achieve a desired effect.

In some embodiments, the methods are used to prevent, lessen, or treat apoptosis in tissues. In some embodiments, the methods are used to decrease or prevent apoptosis in a tissue that has been injured. In some embodiments, the methods are used to prolong the life of organs being stored prior to transplant. In some embodiments, the methods are used to treat or prevent damage during and after surgical procedures.

In some embodiments, methods are useful for preserving tissues (e.g., cornea) before transplantation. In some embodiments, the methods lessen cellular damage due to the storage process. In some embodiments, the methods are used to decrease the amount of degradation that occurs in a tissue that is being stored prior to transplantation or surgical procedures. In some embodiments, the preparation or composition is added to the storage medium, with or without collagen and/or HA. Stored tissues such as eyes, organs, skin, and the like can benefit from the decreased cellular apoptosis that occurs when the composition is added.

In some embodiments, the methods further comprise storing a donor tissue in a storage medium until transplantation after the donor tissue is harvested. In some embodiments, the composition is added to the storage medium to prevent cellular apoptosis. In some embodiments, the composition is added to storage media for preserving limbal epithelial stem cells. In some embodiments, the composition is added to cell culture medium or digestion medium to prevent cellular (e.g., keratocyte) apoptosis. Because studies described herein show that incubation of composition during dispase digestion (a treatment which mimics surgical and pathological insults such as excimer ablation in PRK and recurrent corneal erosion, respectively) significantly reduced apoptosis of both epithelial cells and keratocytes. In some embodiments, the composition is administered to an eye receiving mechanical scraping or excimer laser photoablation to attempt to reduce keratocyte apoptosis, and hence reduce corneal haze. In some embodiments, the methods are used in a surgical condition or disease such as recurrent corneal erosion or keratoconus where the basement membrane is dissolved to reduce the keratocyte apoptosis.

In some embodiments, the method is used to produce a phenotypic reversal of AMSCs from myofibroblasts to fibroblasts. In some embodiments, the method is used to prevent or slow differentiation of various cell types. In some embodiments, many types of cells are treated with the method. This method is particularly useful for expanding cell cultures without causing differentiation of the culture to unwanted cell types.

Kits/Articles of Manufacture:

For use in the methods described herein, kits and articles of manufacture are also described herein. In some embodiments, the kits comprise a carrier, package, or container that is compartmentalized to receive one or more containers such as vials, tubes, and the like, each of the container(s) including one of the separate elements to be used in a method described herein. In some embodiments, the container is a bottle, vial, syringe, or test tube. In some embodiments, the container is formed from a variety of materials such as glass or plastic. In some embodiments, the kit comprising one or more prefilled syringes comprising a composition disclosed herein.

In some embodiments, the article of manufacture contains packaging materials. Packaging materials for use in packaging pharmaceutical products are well known to those of skill in the art. Non-limiting examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the preparations and compositions provided herein are contemplated as are a variety of treatments for any disease, disorder, or condition.

In some embodiments, the container includes one or more preparations of fetal support tissue, optionally in a composition or in combination with another agent as disclosed herein. In some embodiments, the container comprises a sterile access port. In some embodiments, the container is an intravenous solution bag or a vial. In some embodiments, the sterile access port is a stopper pierceable by a hypodermic injection needle. In some embodiments, the kit comprises a composition with an identifying description or label or instructions relating to its use in the methods described herein.

In some embodiments, the kit comprises one or more additional containers, each with one or more of various materials (such as reagents, optionally in concentrated form, and/or devices) desirable from a commercial and user standpoint for use of the composition comprising fetal support tissue. Non-limiting examples of such materials include, but not limited to, buffers, diluents, filters, needles, syringes; carrier, package, container, vial and/or tube labels listing contents and/or instructions for use, and package inserts with instructions for use. In some embodiments, a set of instructions is included.

In some embodiments, a label is on or associated with the container. In some embodiments, the label is on a container when letters, numbers or other characters forming the label are attached, molded or etched into the container itself. In some embodiments, the label is associated with a container when it is present within a receptacle or carrier that also holds the container, e.g., as a package insert. In some embodiments, the label is used to indicate that the contents are to be used for a specific therapeutic application. In some embodiments, the label indicates directions for use of the contents, such as in the methods described herein.

In certain embodiments, the injectable composition is presented in a pack or dispenser device which contains one or more unit dosage forms containing the injectable composition provided herein. In some embodiments, the pack contains metal or plastic foil, such as a blister pack. In some embodiments, the pack or dispenser device is accompanied by instructions for administration. In some embodiments, the pack or dispenser device is accompanied with a notice associated with the container in form prescribed by a governmental agency regulating the manufacture, use, or sale of pharmaceuticals, which notice is reflective of approval by the agency of the form of the drug for human or veterinary administration. In some embodiments, the notice is the labeling approved by the U.S. Food and Drug Administration for prescription drugs, or the approved product insert. In some embodiments, the injectable composition is prepared, placed in an appropriate container, and labeled for treatment of an indicated condition.

The compositions and methods described herein are provided in further detail in the following examples. These examples are provided by way of illustration and are not intended to limit the invention in any way.

EXAMPLES

Example 1: Example Preparation

An injectable composition is prepared by mixing 10 mg each of: HA, TSG-6, PTX-3, and TSP-1, each of which is obtained from a commercial source, with 100 mg of a preparation comprising: placental tissue, umbilical cord tissue, amniotic membrane tissue, chorion tissue or combinations thereof; and then mixed with 10 mL of 0.9% sterile saline. The mixture is incorporated into a dosage unit form suitable for administration by injection.

Example 2: Characterization of Amniotic Membrane Components

Material and Methods

The concentration of proteins in each extract was quantitated by the BCA Protein Assay Kit (Pierce, Rockford, Ill.). The concentration of hyaluronic acid (HA) in each extracts was assayed with Hyaluronic Acid (HA) Quantitative Test Kit (Corgenix, Westminster, Colo.) based on ELISA using a standard curve provided by the manufacturer prepared by serial dilution of HA.

HA Molecular Weight Range Analysis by Hyaluronidase Digestion

The HA molecular weight ranges of the extracts were analyzed by agarose gel electrophoresis according to the method described by Lee and Cowman (Lee H. G. and Cowman, M. K. An Agarose Gel Electrophoretic Method for Analysis of Hyaluronan Molecular Weight Distribution. Analytical Biochemistry, 1994, 219, 278-287). The samples were subjected to 0.5% agarose gel electrophoresis followed by staining using 0.005% Stains-All (Sigma, cat #23096-0) in 50% ethanol. The gel was stained overnight under a light-protective cover at room temperature (Shorter staining periods of 3-4 hr can also give acceptable results). HA was visualized as blue bands after destaining by transferring the gel to H$_2$O and exposed to the room light for approximately 6 hr. The molecular weight standards included λ DNA-BstE II digested restriction fragments (cat #D9793, Sigma) ranging in MW from 0.9 to 5.7×10$^6$. The authenticity of HA was further verified by incubation of the extract with or without 10 units/ml hyaluronidase (Sigma #H1136) in the reaction buffer (50 mM Tris-HCl, pH7.5, 0.1 M NaCl, 1% Triton X-100, 0.1% BSA supplemented with the above protease and phosphatase inhibitors) for 2 h at 37° C. using a positive control of high MW HA (cat #H1876, Sigma) purified from human umbilical cords.

Western Blot Analyses

The above extracts were electrophoresed on 4-15% denatured acrylamide gels and transferred to the nitrocellulose membrane, and then immunoblotted with a rabbit antihuman inter-α-trypsin inhibitor (rabbit polyclonal antibody (cat #A0301, DAKO at 1:1000), a rabbit anti-human TSG-6 polyclonal antibody (provided by Dr. Tony Day at 1:1000 dilution), a rat monoclonal anti-PTX3 antibody (Alexis Biochemicals, ALX-804-464, 1 µg/ml), an anti-thrombospondin-1 antibody obtained from Calbiochem (Cat #BA24), and a goat anti-human Smad 7 antibody (AF2029, 1:1000, R & D Systems). Immunoreactive protein bands were detected by Western Lighting™ Chemiluminescence Reagent (PerkinElmer).

Results

Experiments showed that the observed suppressive effect on the TGF (31 promoter activity was abolished when water-soluble AM extracts were pre-heated at 90° C. for 10 minutes, suggesting that the responsible component(s) most likely contained protein(s), of which the conformation is important.

Quantitation of HA and Proteins in AM Extracts

The results, summarized Table 1, showed that all AM and jelly extracts contained both HA and proteins. In general, the weight ratio between proteins and HA was high in the Total Extract than the supernatant (e.g., L and H for PBS, and A for Buffer A) after centrifugation for AM, suggesting that most protein-containing materials were eliminated by centrifugation. However, this trend was not noted in AM Jelly, suggesting that AM extracts contained more proteins than Jelly (see T under PBS and T under A/B/C). The ratio between proteins and HA was also increased from Extract A to Extracts B and C for both AM and AM jelly, further supporting that HA was mostly present in the soluble form, and vice versa proteins were found more in the water-insoluble components. Furthermore, HA was largely removed from AM Jelly after centrifugation in A/B/C.

TABLE 1

| | Tissue | | | | | | | | | | | | | |
| --- | --- | --- | --- | --- | --- | --- | --- | --- | --- | --- | --- | --- | --- | --- |
| | AM | | | | | | | Jelly | | | | | | |
| | Buffer | | | | | | | | | | | | | |
| | PBS | | | A/B/C | | | | PBS | | | A/B/C | | | |
| Fraction | T | L | H | T | A | B | C | T | L | H | T | A | B | C |
| Protein (µg/ml) | 8645 | 1370 | 1467 | 8645 | 2731 | 930 | 2698 | 3836 | 3645 | 3589 | 3836 | 3893 | 527 | 1364 |
| HA (µg/ml) | 75 | 62 | 44 | 60 | 74 | 7 | 35 | 80 | 90 | 96 | 129 | 94 | 2 | 7 |
| Protein/HA | 115 | 22 | 33 | 144 | 37 | 133 | 77 | 48 | 41 | 37 | 30 | 41 | 264 | 195 |

[Note]:
T: Total; L: the supernatant following the low speed centrifugation of the total extract; H: the supernatant following the low speed centrifugation of the total extract; A, B, C: Extracts, see text.

Figure 10:
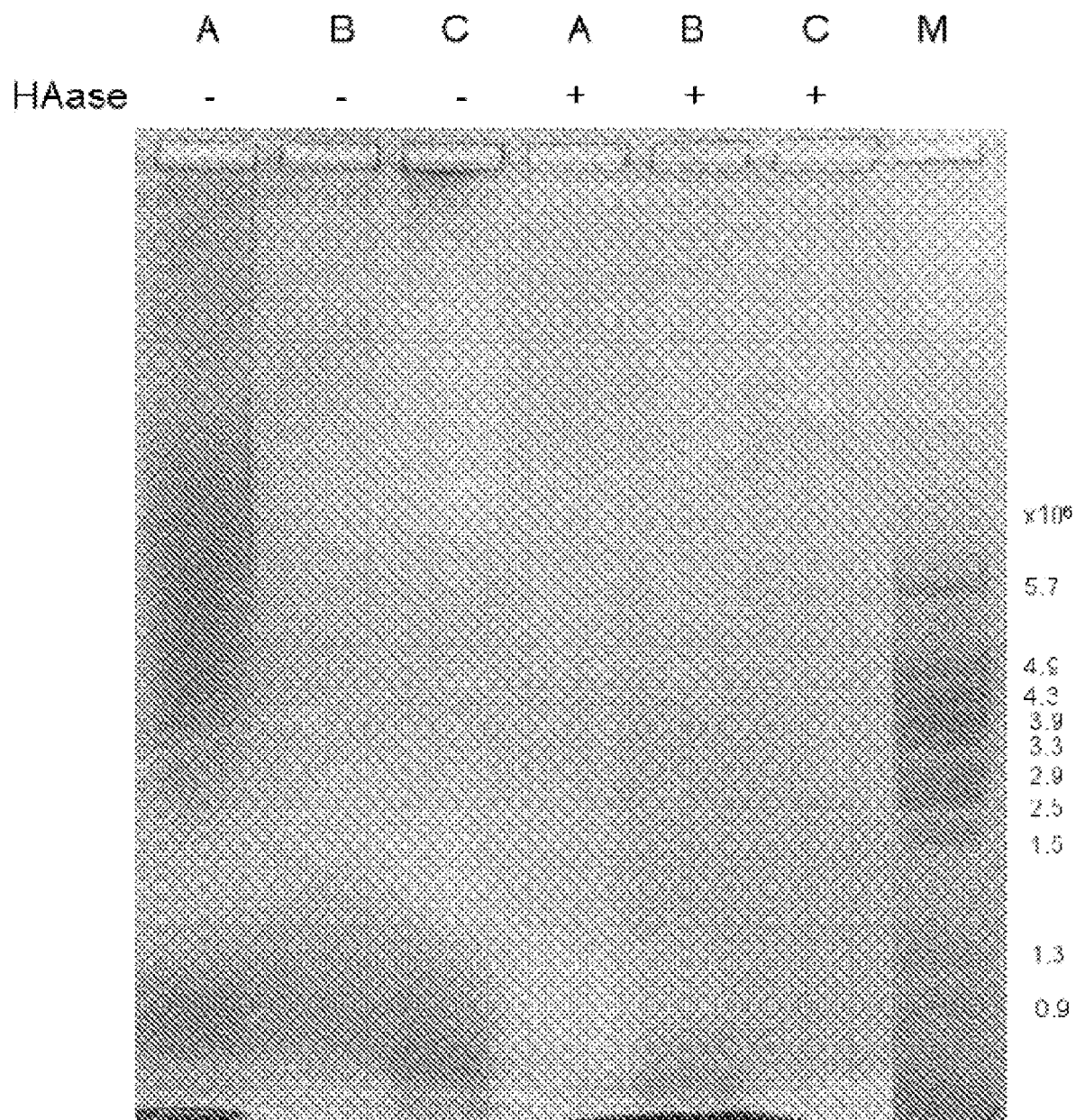
FIG. 10 illustrates the molecular weight ranges of hyaluronan in AM extracts separated by agarose gel electrophoresis. Amniotic membrane extracted by buffer A, B, C were treated with or without hyaluronidase and electrophoretically separated by a 0.5% agarose gel.
Figure 11:
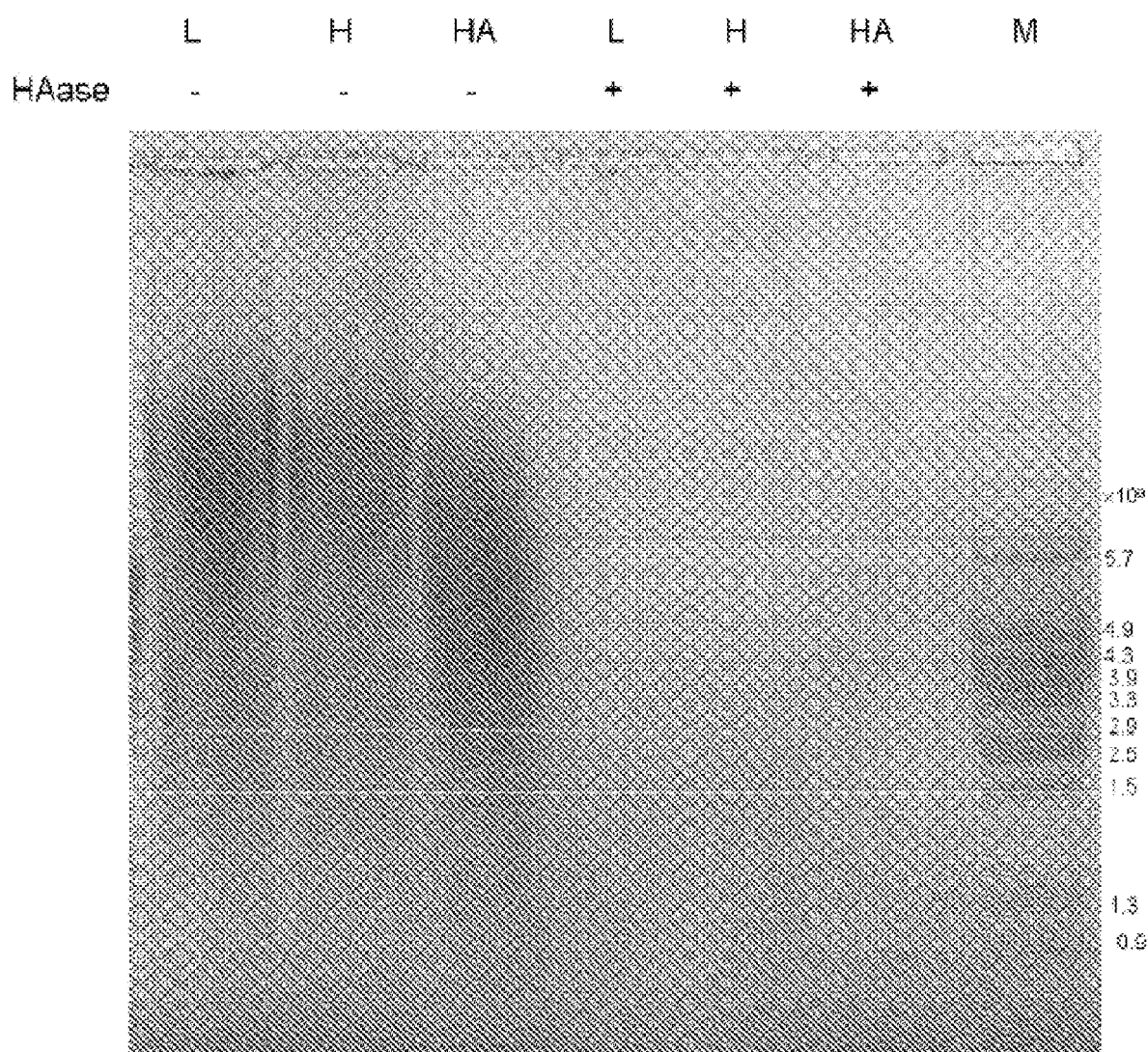
FIG. 11 illustrates the molecular weight ranges of hyaluronan in AM extracts separated by agarose gel electrophoresis. Amniotic membrane extracted by buffer PBS were treated with or without hyaluronidase (10 units/ml in Tris-HCl, pH 7.5, 150 mM NaCl) for 2 hr at 37° C. and run through 0.5% agarose gels. HA: positive hyaluronic acid control; L: AM extract after low speed centrifugation; H: AM extract after high speed centrifugation.

HA in Different AM Extracts had Molecular Weights Greater than One Million Daltons High molecular weight (>$10^6$ daltons) of HA was present in the total extracts and Extract A (FIG. 10). However, even higher MW of HA was present in Extract B, while HA was found in a narrow band with even higher MW in Extract C (FIG. 10). All of the HA-containing components disappeared after hyaluronidase digestion, confirming that they indeed contained HA. Compared to the positive control of HA obtained from Sigma (cat #H1136), a similar high molecular weight (>$10^6$ daltons) of HA was also found in both supernatants obtained after low and high speeds of centrifugation (FIG. 11). Again these HA-containing bands disappeared after hyaluronidase digestion. A similar result was obtained for AM jelly.

Figure 12:
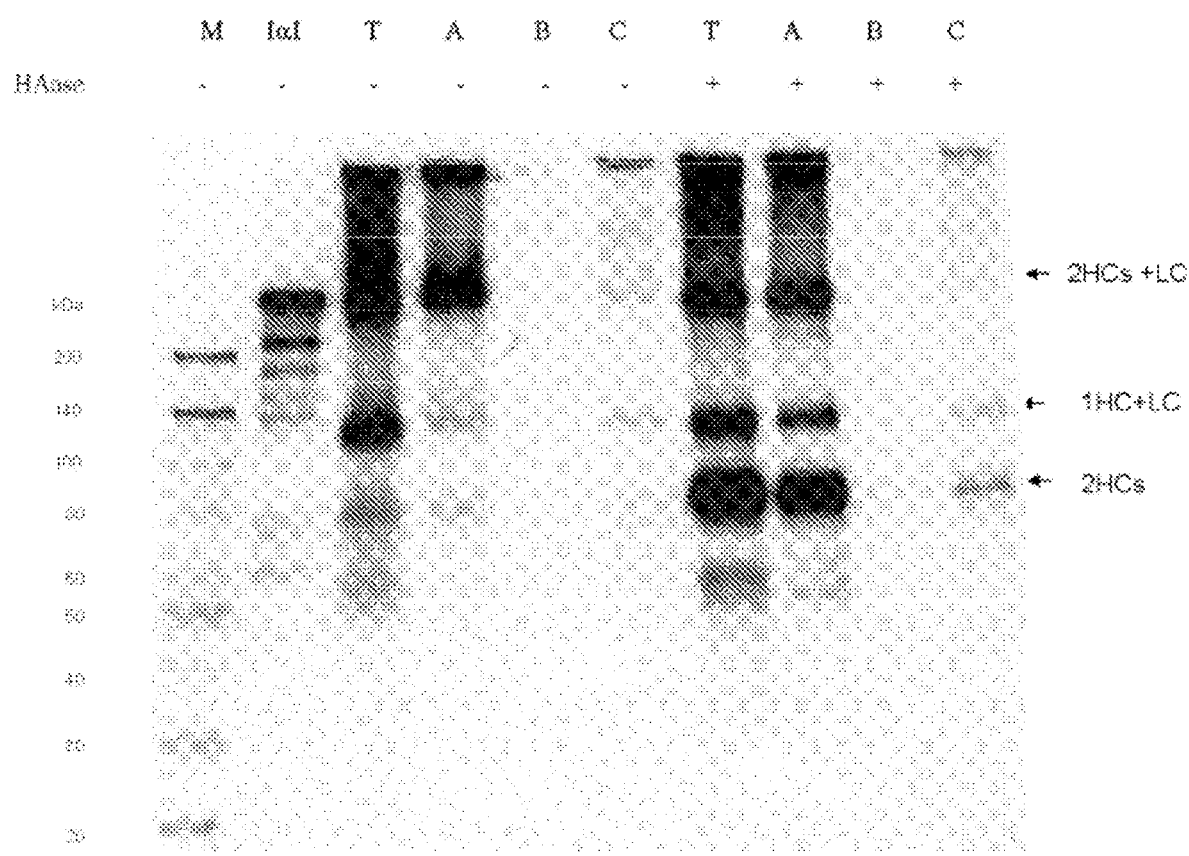
FIG. 12 illustrates a western blot demonstrating that the inter-α-trypsin inhibitor (IαI) is present in AM extracts. IαI was present in AM extract A and C although the signal of bikunin was very weak (.about.39 kDa). Prior to transfer to the western blot, the extract was separated on a 4-15% denatured acrylamide gel.
Figure 13:
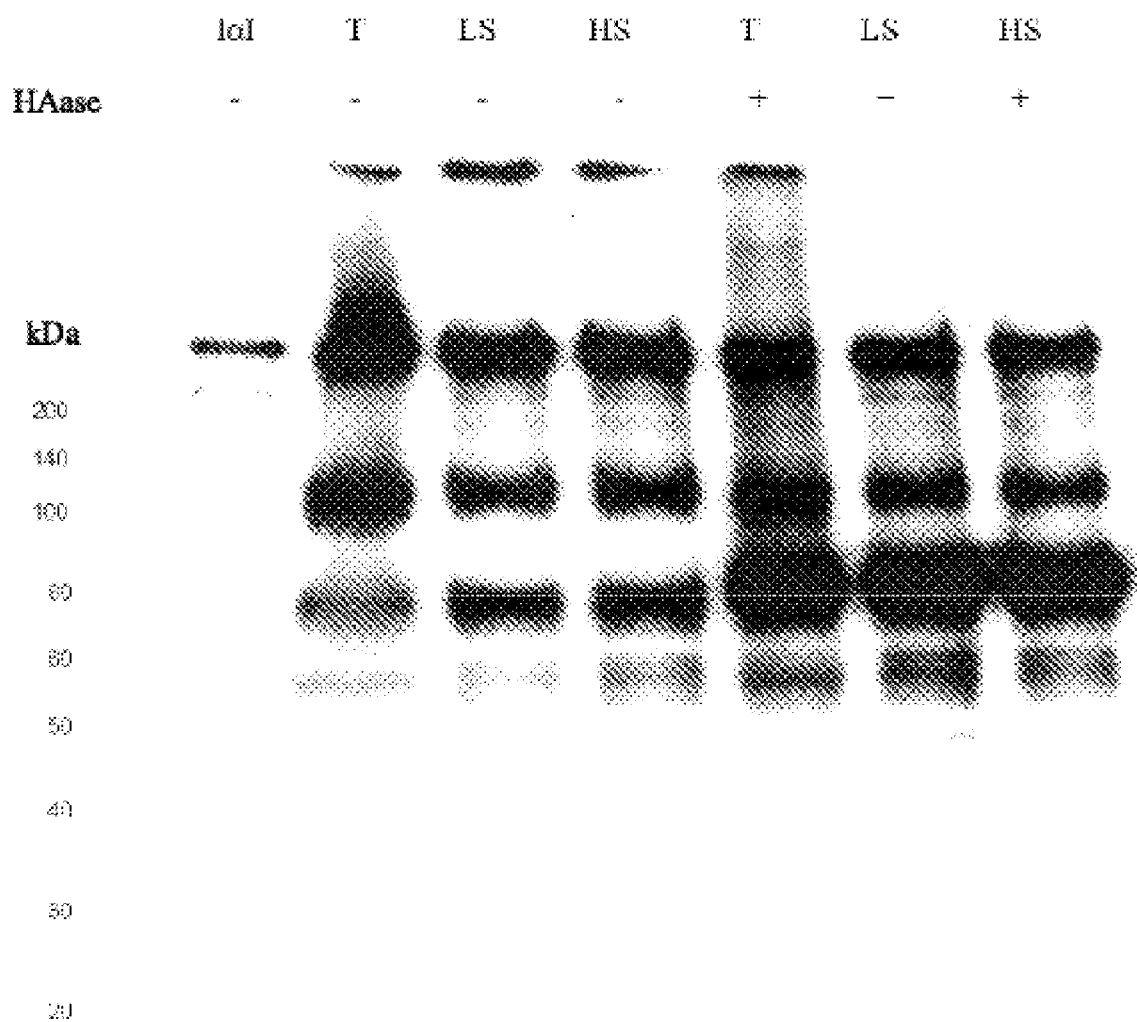
FIG. 13 illustrates an immunoblot demonstrating that the inter-α-trypsin inhibitor (IαI) is present in the AM extracts even after low (LS) or high speed (HS) centrifugation.

Inter-α-Trypsin Inhibitor (kJ) was Present in Different AM Extracts and its Heavy Chains (HCs) were Covalently Linked with HA FIG. 12 showed that before digestion with hyaluronidase, free heavy chains were present in different complexes, and a small amount of light chain was also present (UTI or bikunin). However, in all extracts, i.e., total and Extracts A, B, and C, there was also a covalently linked complex between HA and heavy chains of IαI as the latter was released only after hyaluronidase digestion. The same result was obtained in Extracts H and L obtained by two different speeds of centrifugation (FIG. 13).

Tumor Necrosis Factor-Stimulated Gene 6 (TSG-6) was also Present in AM Extracts

Figure 14:
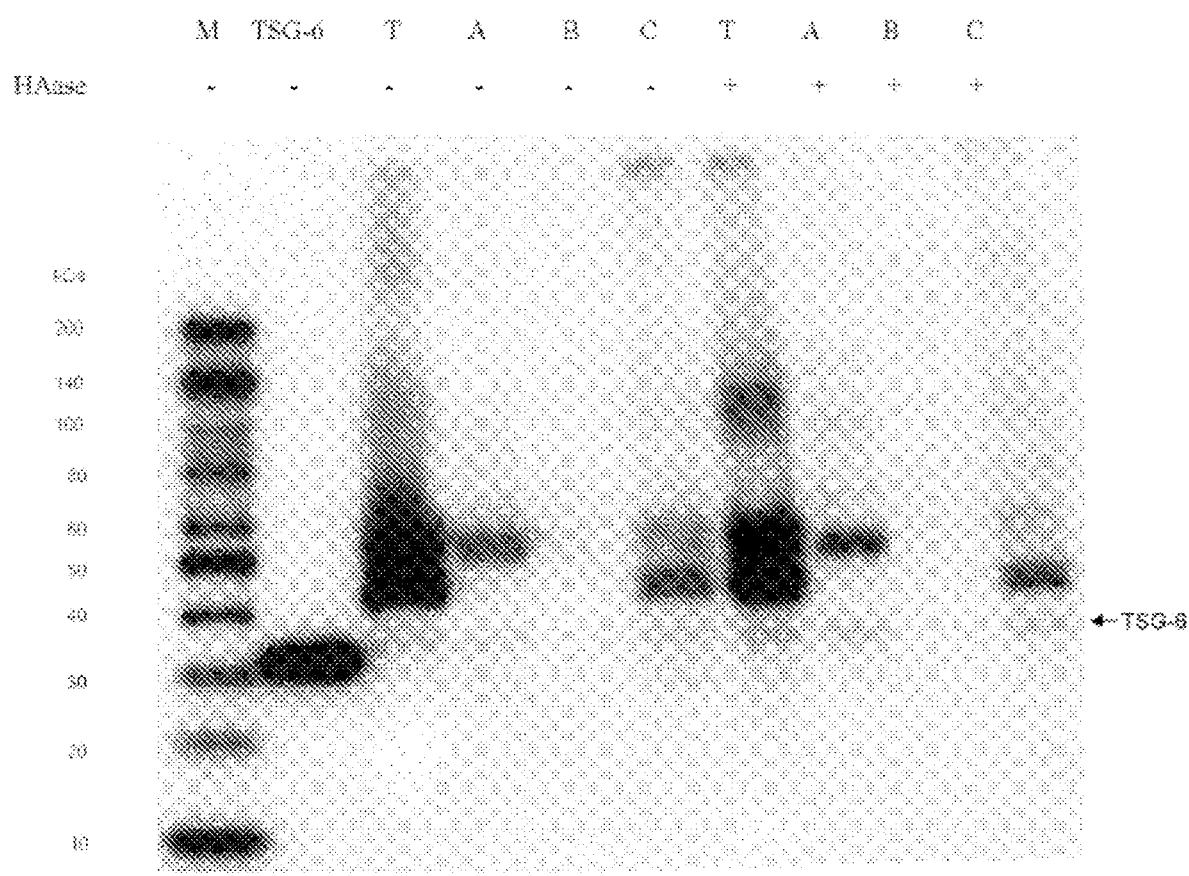
FIG. 14 illustrates an immunoblot of TSG-6 (Tumor Necrosis Factor-Stimulated Gene 6), either with (+) or without (−) hyaluronidase treatment. The samples included total AM extract without centrifugation (T), AM Extract after extraction in isotonic low salt buffer (buffer A); high salt buffer (B); or 4 M guanidine HCl (C); as detailed in Example 2. TSG-6 was present in the total extract, buffer A extract, and buffer C extract. The addition of hyaluronidase did not appear to alter the TSG-6 level in the extracts.
Figure 15:
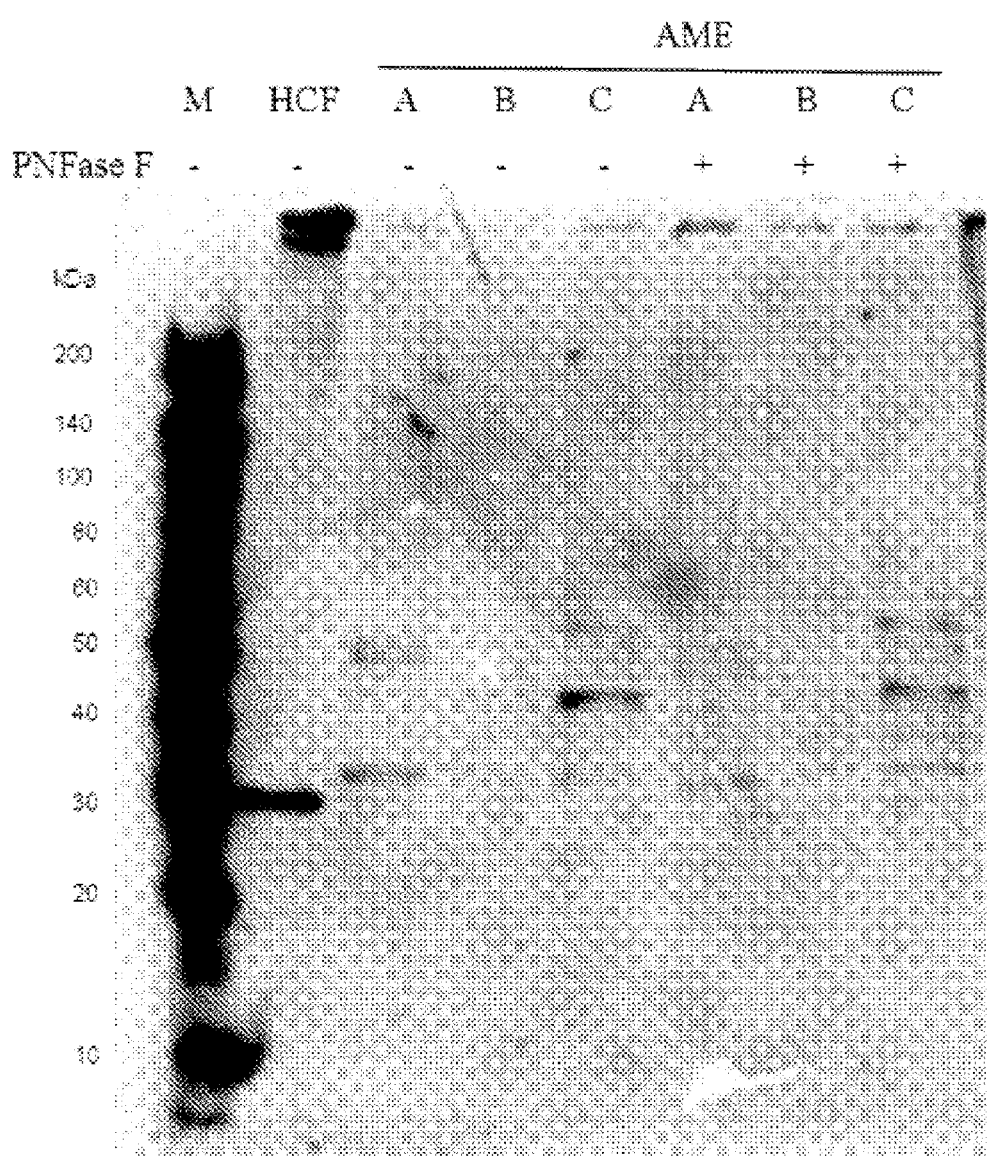
FIG. 15 illustrates an immunoblot analysis of the deglycosylation of TSG-6 in AM. AM extract A, B, and C were treated with (+) or without 20 units/ml PNGase F at 37° C. for 3 hours. Glycosylation of TSG-6 in AM was then analyzed by western blot. The cell lysate of human corneal fibroblast (HCF) was used as a positive control.
Figure 16:
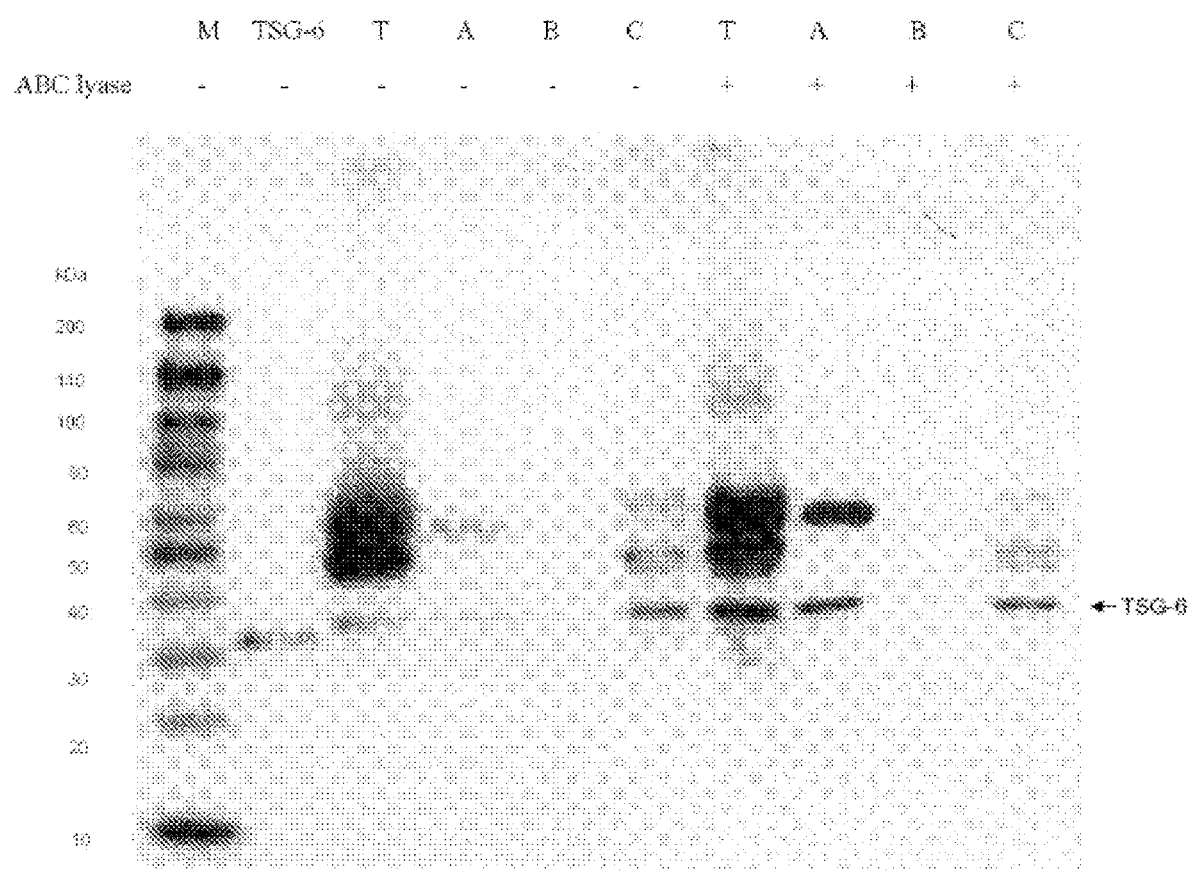
FIG. 16 illustrates an immunoblot analysis of potential TSG-6 complexes in AM by digestion with Chondroitin Sulfate ABC lyase. AM extract A, B, and C were treated without (−) or with (+) 1 unit/ml ABC lyase at 37° C. for 2 hours. The possible disruption of TSG-6 complexes was then analyzed by western blot using an anti-TSG-6 antibody RAH-1:1:1000.
Figure 17:
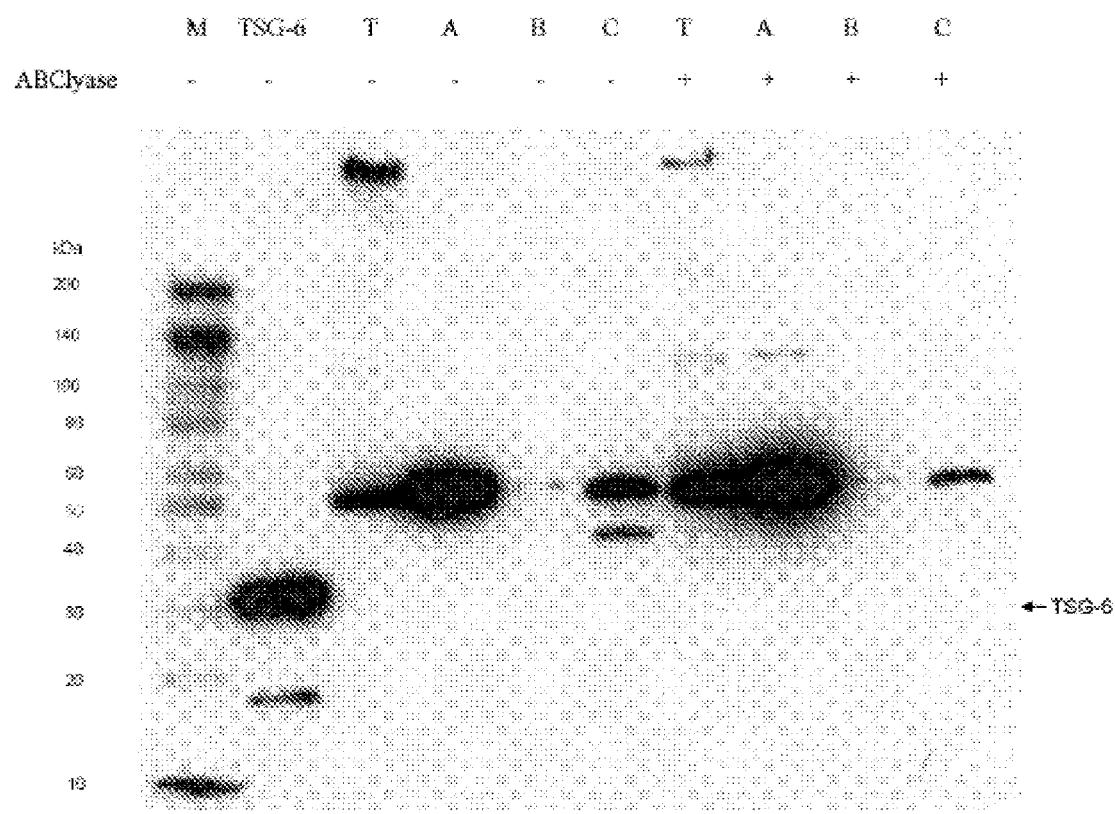
FIG. 17 illustrates an immunoblot of potential TSG-6 complexes in AM by digestion with Chondroitin Sulfate ABC lyase. This is the same experiment as shown in FIG. 16 except that a different TSG-6 antibody was used. Here, the anti-TSG-6 antibody was obtained from R & D Systems (cat #MAB2104).

FIG. 14 showed that TSG-6 (about 38 kDa) was present in Total, Extract A and Extract C. In Extract A, there was a band of about 38 kDa migrated close to that of the purified TSG-6 (35 kD). The identity of other bands of about 45 and 55 kDa was unknown. Total AM extract (without centrifugation) "T" showed two bands (both above 35 kD), and the higher one (55 kD) that were found in Extract A (after centrifugation), while the lower one (45 kD) was found in Extract C. All of these bands were not significantly altered when samples were treated with hyaluronidase (FIG. 14) or with F-glycosidase (FIG. 15). However, digestion with chondroitin sulfate ABC lyase resulted in more noticeable 38 kD band using antibody RAH-1 (FIG. 16) but not using antibody MAB2104 (FIG. 17).

Figure 18:
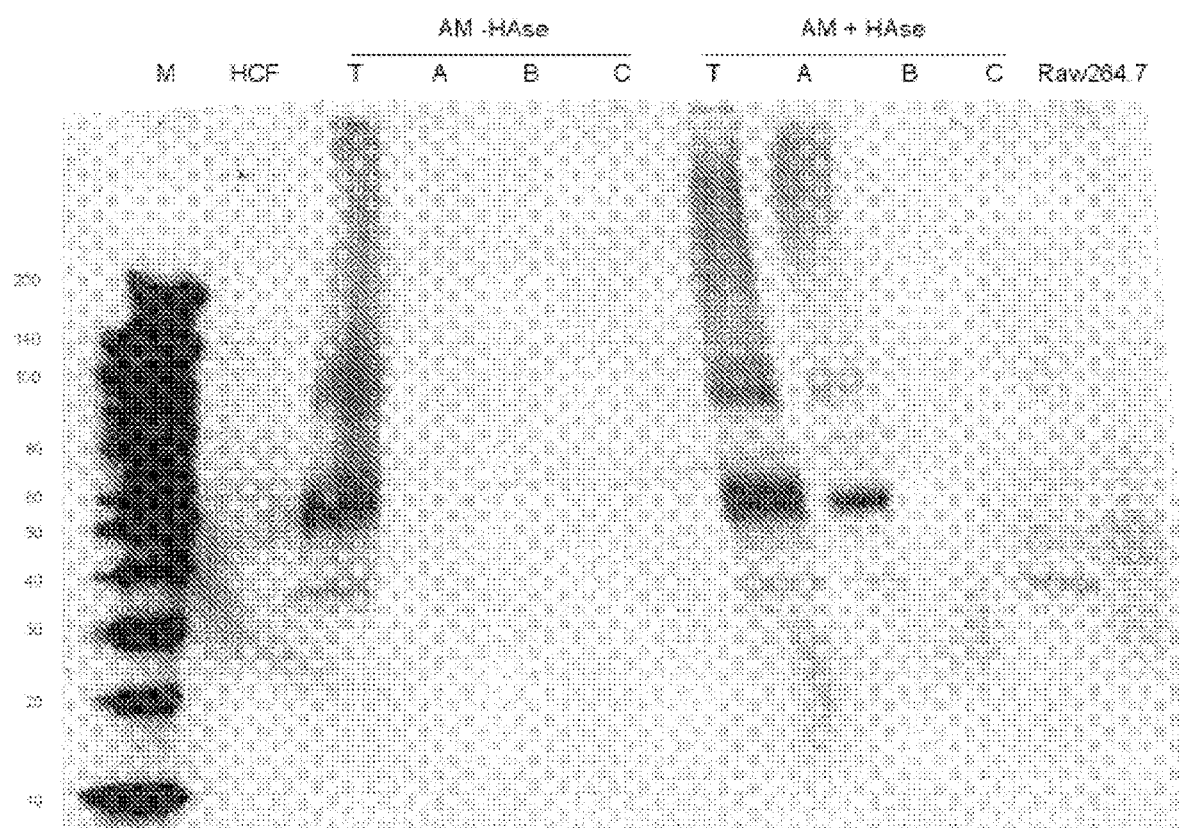
FIG. 18 illustrates an immunoblot demonstrating the presence of Pentraxin (PTX3) in AM, using a rat monoclonal anti-PTX3 antibody obtained from Alexis Biochemicals. HCF: human corneal fibroblast, T, A, B, C: AM extract Total, A, B, C, respectively; HAse: Hyaluronidase.

Pentraxin-3 (PTX-3) was Exclusively Present in Water-Soluble AM Extracts and Formed a Complex with HA FIG. 18 showed that PTX3 was also present in AM extracts and was complexed with HA in the water soluble extract A only.

Thrombospondin-1 (TSP-1) was Present in Different AM Extracts

Figure 19:
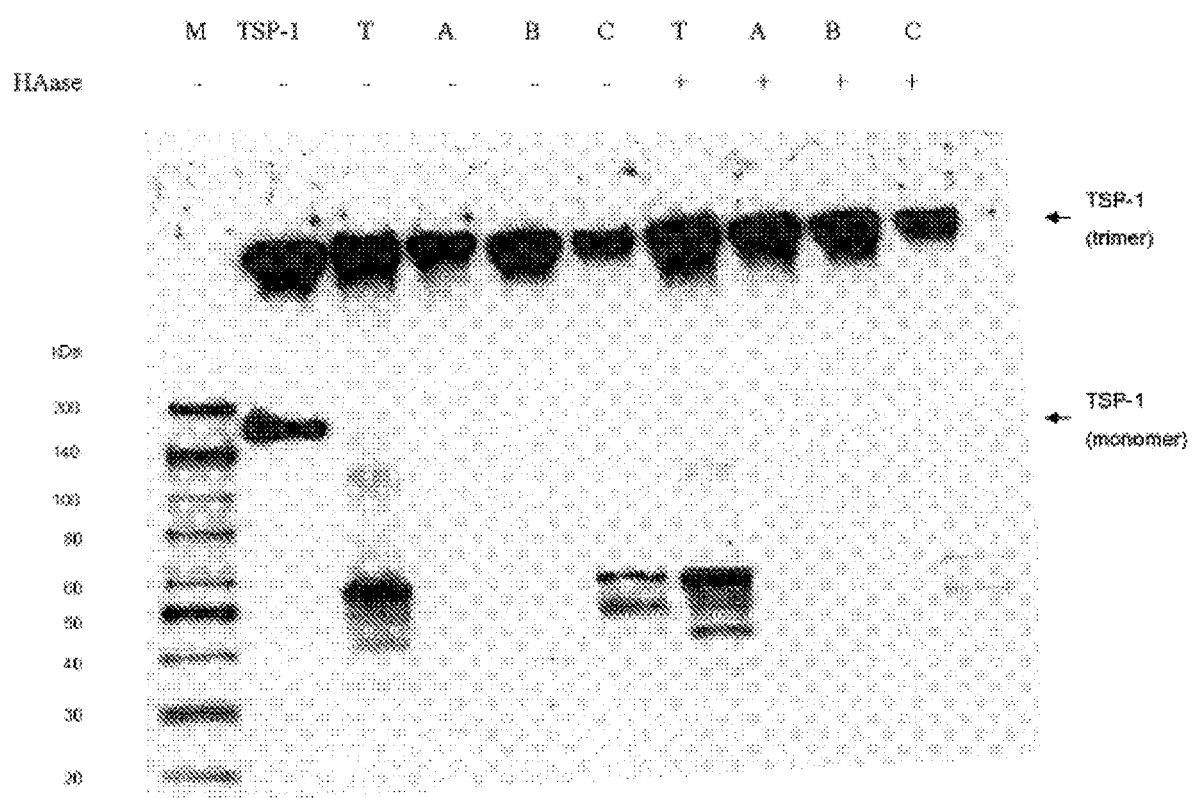
FIG. 19 illustrates an immunoblot demonstrating the presence of TSP-1 in AM. The monomeric TSP-1 (180 kDa) and the putative trimeric TSP-1 (540 kDa) are indicated. The positive control, TSP-1, was purified from human platelets (Calbiochem, Cat #605225) and loaded as 100 ng/lane.

FIG. 19 showed that all AM extracts had a high molecular weight band of TSP-1 while the total extract (T) and Extract C also had some bands between 35-120 kDa. Hyaluronidase digestion did not change the reactive pattern except some bands became a little stronger or weaker.

Smad7 was Present in Mostly in Water-Insoluble AM Extracts

Figure 20:
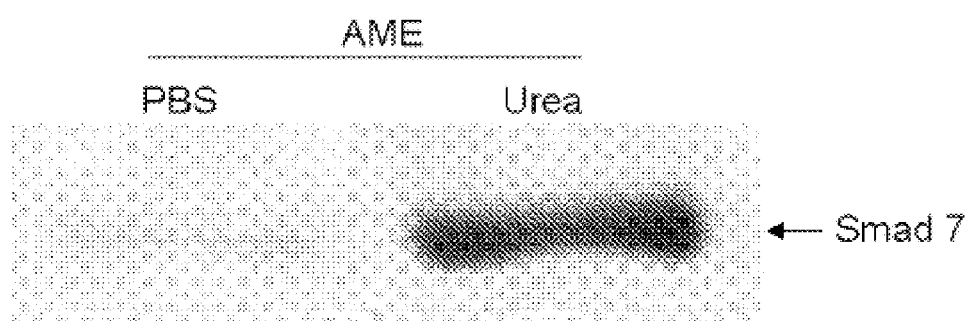
FIG. 20 illustrates an immunoblot demonstrating the presence of Smad 7 in AM. AM was extracted with PBS or urea (2M urea in 50 mM Tris-HCl, pH 7.5). 20 µg of total protein was loaded for each extract. Smad 7 was detected with goat anti-human Smad 7 (AF2029, 1:1000, R & D Systems). Smad 7 migrated as a band of ~51 kDa.

Smad 7 was found in both PBS extracts and urea extracts of AM (FIG. 20).

Example 3: Signaling Pathways Control Proliferation and EMT of Epithelial Cells Proliferation and EMT by dysfunctional epithelial cells are two major pathological processes. During rhegmatogenous retinal detachments (RRDs), retinal pigment epithelium (RPE) cells are dispersed into the vitreous, which contains many growth factors and cytokines (e.g., EGF, FGF, PDGF, TGF-β, VEGF and IFN-γ) necessary for the bioactivity of proliferative vitreoretinopathy (PVR) as identified recently. To understand how growth factors might contribute to proliferation and EMT of dispersed RPE cells, an in vitro culturing model of ARPE-19 cells, which these cells exhibit contact inhibition after seven days of post-confluence was used.

Figure 5A:
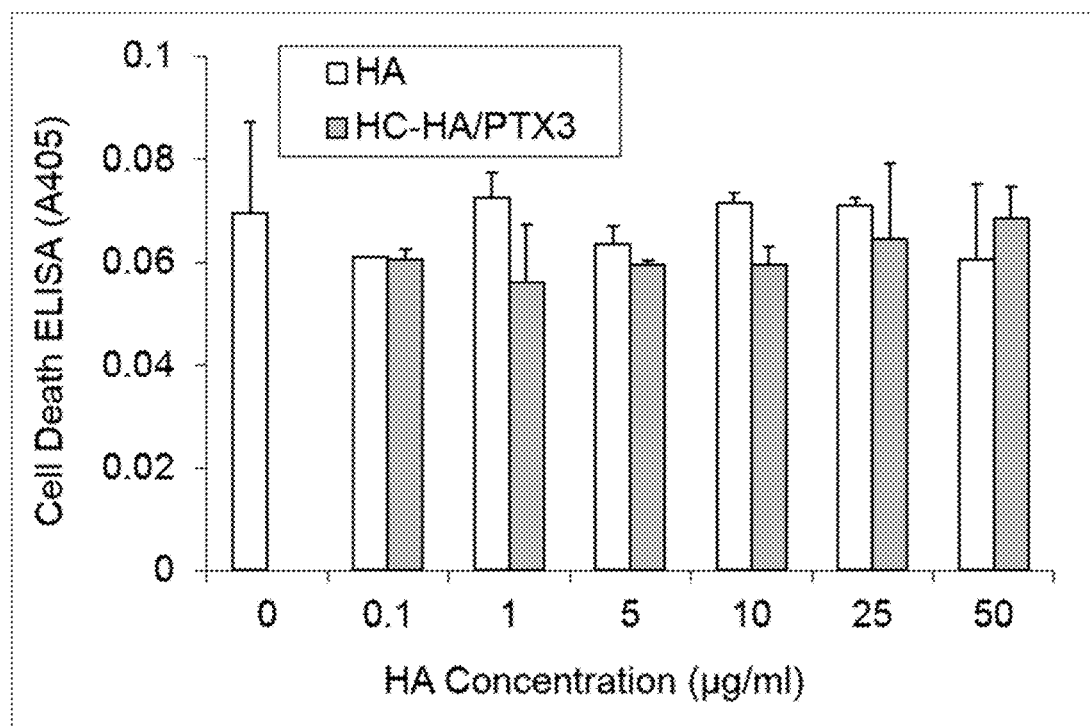
FIGS. 5A-5C illustrate HC-HA/PTX3 inhibits proliferation in ARPE-19 cells when stimulated with EGF+FGF-2.
Figure 5B:
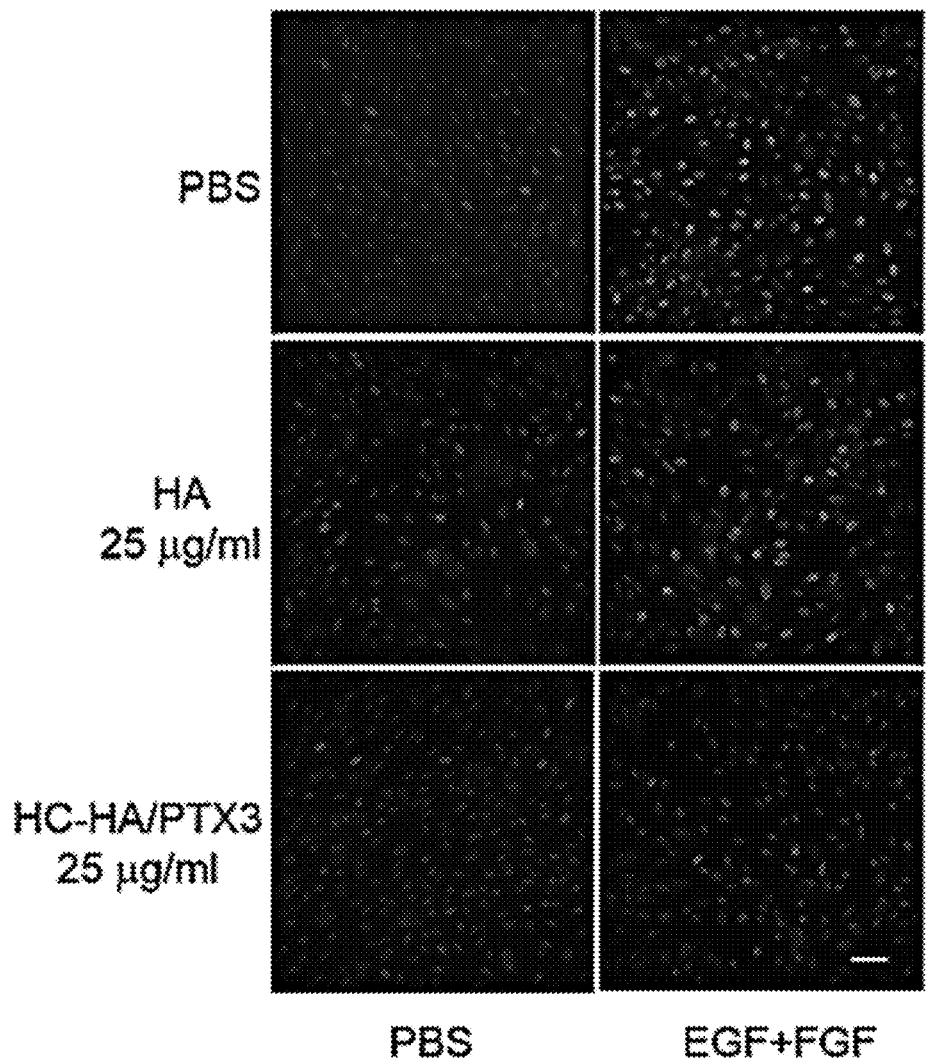
Figure 5C:
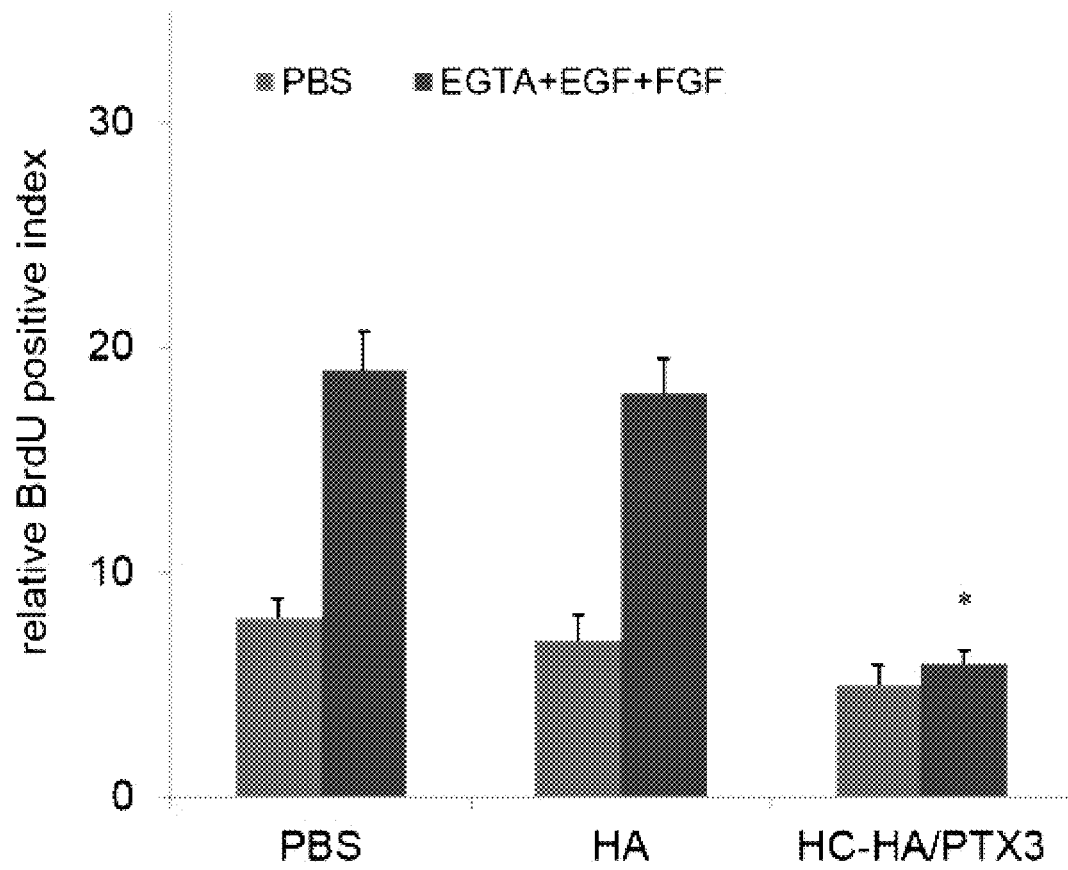
Figure 6A:
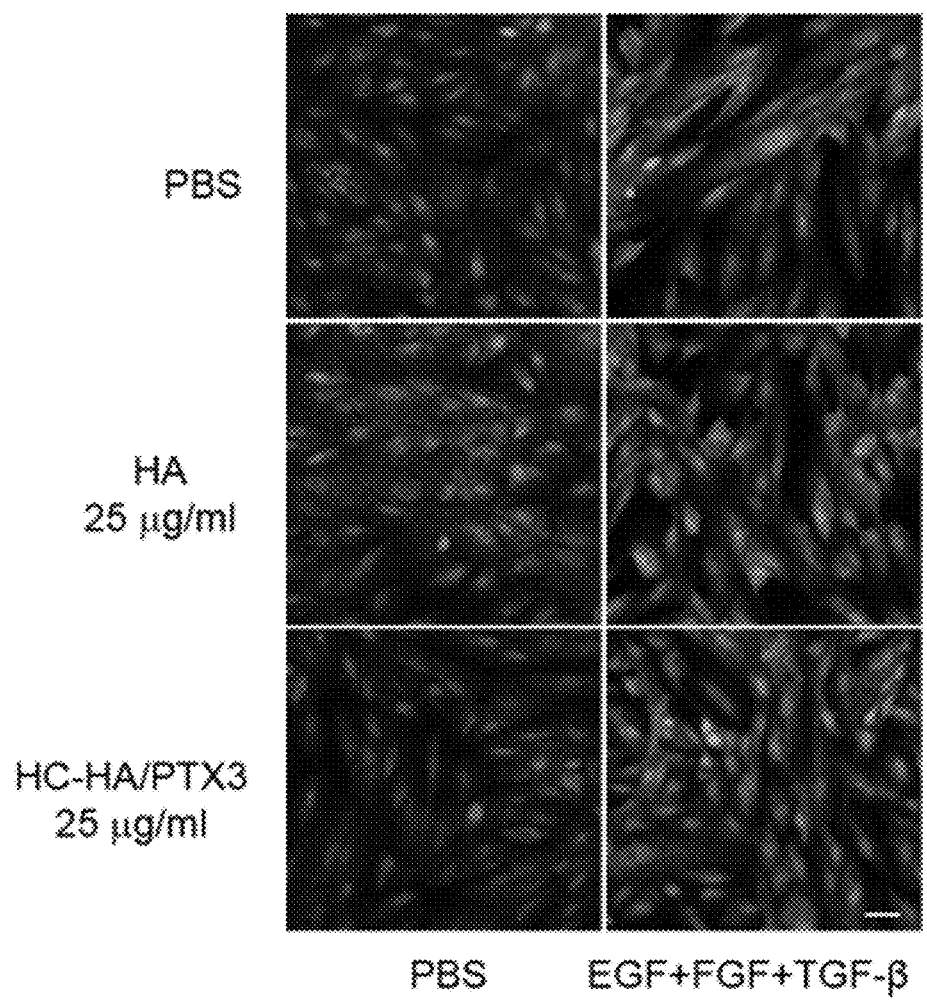
FIGS. 6A-6B illustrate HC-HA/PTX3 inhibits nuclear translocation of pSmad2/3 in APRE-19 cells.
Figure 6B:
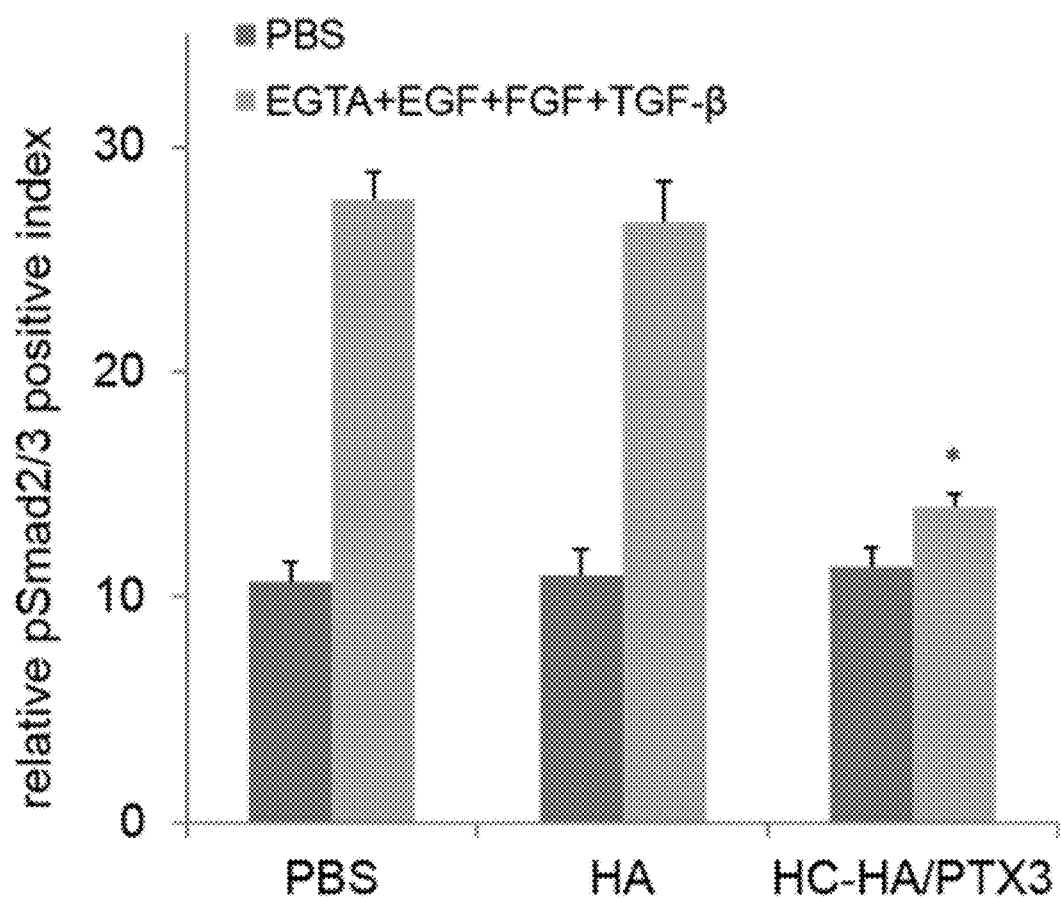

Following perturbation of contact inhibition by EGTA, cell proliferation (BrdU labeling) and EMT (loss of normal RPE phenotype markers of N-cadherin, ZO-1, Na,K-ATPase, and RPE65, and express of mesenchymal phenotype markers of vimentin, S100A4, and α-SMA) were only induced in the presence of EGF and/or FGF-2. This pathological process required the activation of canonical Wnt signaling, as evidenced by the increased nuclear level and interaction of β-catenin and LEF, as well as upregulation of TCF/LEF transcriptional activation. The activation of canonical Wnt signaling was confirmed by using a Wnt inhibitor XAV939 and overexpression of constitutive active β-catenin (S33Y) in blocking or rescuing experiments. Addition of TGF-β1 also lead to EMT by activating Smad/ZEB1/2 signaling, which suppressed proliferation and activation of canonical Wnt signaling. Furthermore, canonical Wnt signaling triggered by EGF+FGF-2 was sufficient and synergized with TGF-β1 to lead to EMT (FIG. 1). These findings provided the mechanistic insight for us to target these two signaling pathways so as to prevent PVR. The in vitro model using ARPE-19 cell line was further optimized based on a low cell density instead of by adding EGTA to confluent cells to initiate proliferation to better mimic PVR. The results showed HC-HA/PTX3 did not harm the non-stimulated ARPE-19 cells (FIG. 5A), but significantly suppressed the proliferation (FIGS. 5B and 5C) and the nuclear localization of phosphorylated Smad2/3 (FIGS. 6A and 6B) after stimulation with EGF+FGF-2 and EGF+FGF-2+TGF-β1, respectively. The establishment of such an in vitro model allowed for the determination of optimal dosing of HC-HA/PTX3 to be used for in vivo testing, in the rabbit PVR animal model provided herein (FIGS. 7A-D).

Example 4: Development of an Animal Model of PVR

PVR was successfully reproduced in rabbits (see FIGS. 7A-7D) by vitreous detachment by gas compression vitrectomy followed by intravitreal injection of rabbit RPE cells to mimic human PVR. Rabbits were chosen because they can develop medullary wing detachments that simulate retinal detachments in humans and show PVR-like features.

NZW rabbits (Female, aged 3-7 months, weighing between 1.5 and 5.0 kg) were subjected to vitrectomy by intravitreal gas injection by injecting 0.3 ml of 100% C3F8 gas into the vitreous cavity using a 32 gauge ½" needle 3 mm posterior to the corneoscleral limbus under direct visualization using indirect ophthalmoscopy following anterior chamber paracentesis performed to lower the intraocular pressure and reduce the possibility of ocular damage caused by an acute increase in pressure. Indirect ophthalmoscopy was performed to ensure there is normal vascular flow in the retina. The intraocular pressure was checked using a Perkins tonometer until the intraocular pressure is below 20 mmHg. PVR was created by intravitreal injection of $2.0 \times 10^5$ rabbit RPE cells that had been prepared from tissue cultured homologous primary rabbit RPE cells in a total of 0.1 ml volume via a 32 gauge ½" needle, with the bevel facing upward, and injected into the vitreous cavity, just in front of the optic nerve head (slowly, to prevent retinal damage). If the treatment of HC-HA/PTX3 was simultaneous with RPE cells, then PBS or two different doses of HC-HA/PTX3 were injected similarly into the vitreous cavity of the control rabbits or treated rabbits, respectively. If the treatment of HC-HA/PTX3 was subsequent with RPE cells, PBS and HC-HA/PTX3 was injected into the vitreous cavity one week later. In each condition, the rabbits were immediately placed on their backs for 1 h to allow the cells and reagents to settle over the vascular wings of the retina.

Figure 7A:
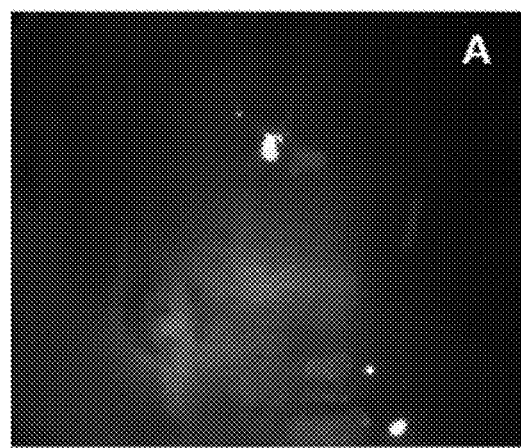
FIGS. 7A-7D illustrate development of PVR in rabbits.
Figure 7B:
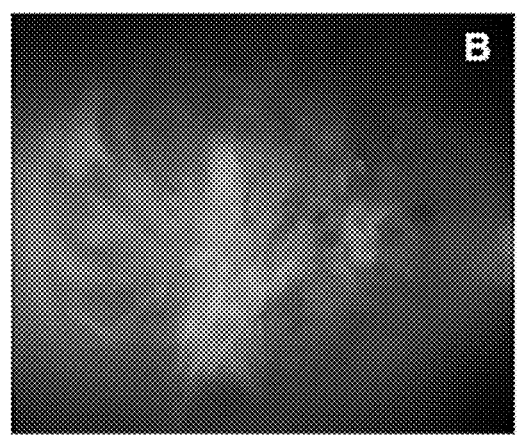
Figure 7C:
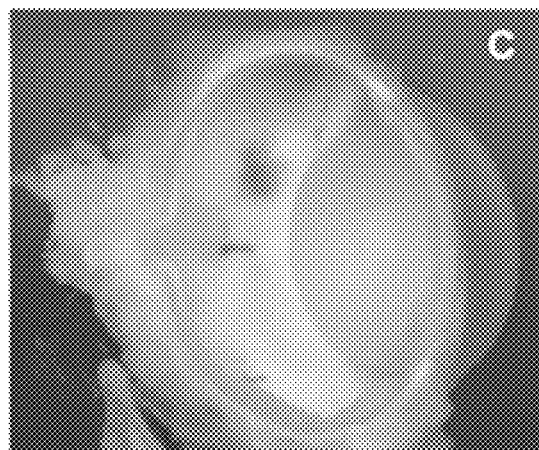
Figure 7D:
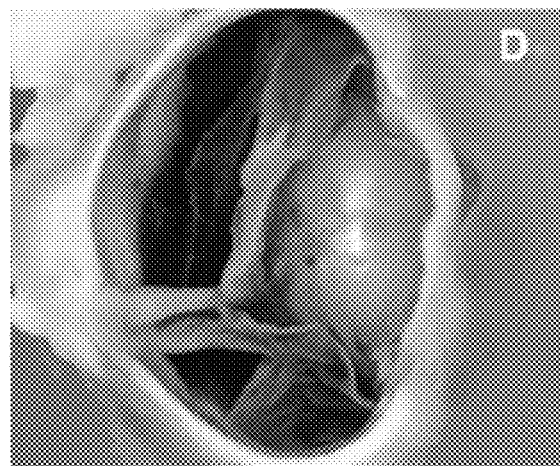

Four weeks after injection of the intravitreal HC-HA/PTX3 or saline the rabbits were sacrificed by euthanasia by anesthetic overdose with Euthasol (390 mg/mL/kg, intravenous). The eyeball was enucleated with all conjunctival tissues, and fixed in 10% formalin. The eyes underwent external examination and then the superior cap is removed to allow internal examination. The gross anatomical examination of the enucleated eyes was photographed using a Nikon D600 camera (FIG. 7C and FIG. 7D).

Figure 2A:
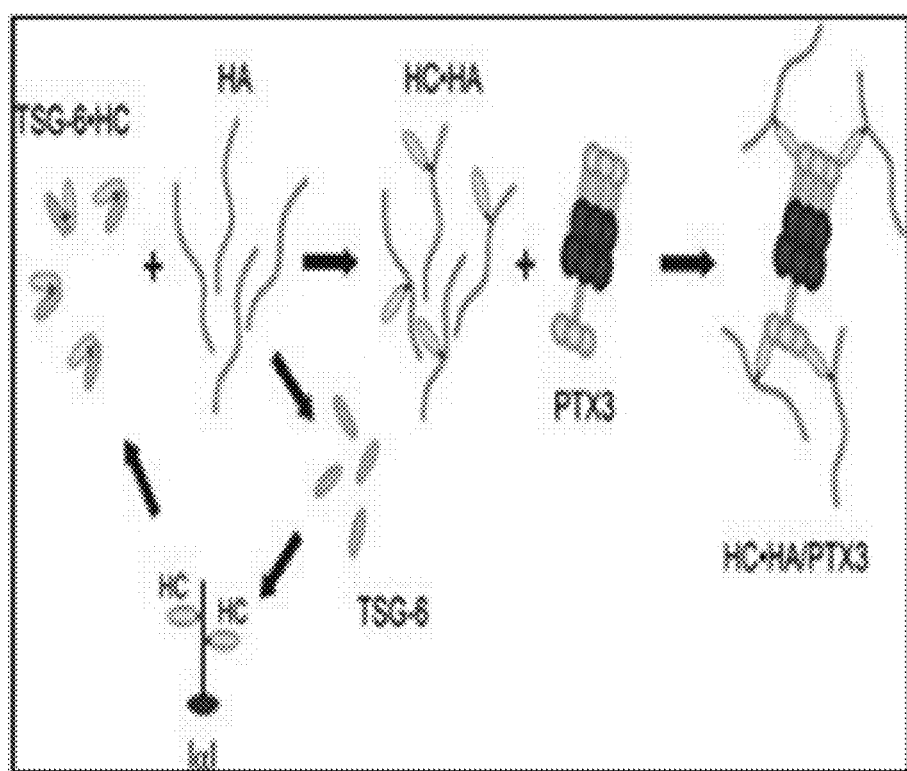
FIGS. 2A-2D illustrate HC-HA/PTX3 formation and characterization of HC-HA/PTX3 purified from human AME.
Figure 2B:
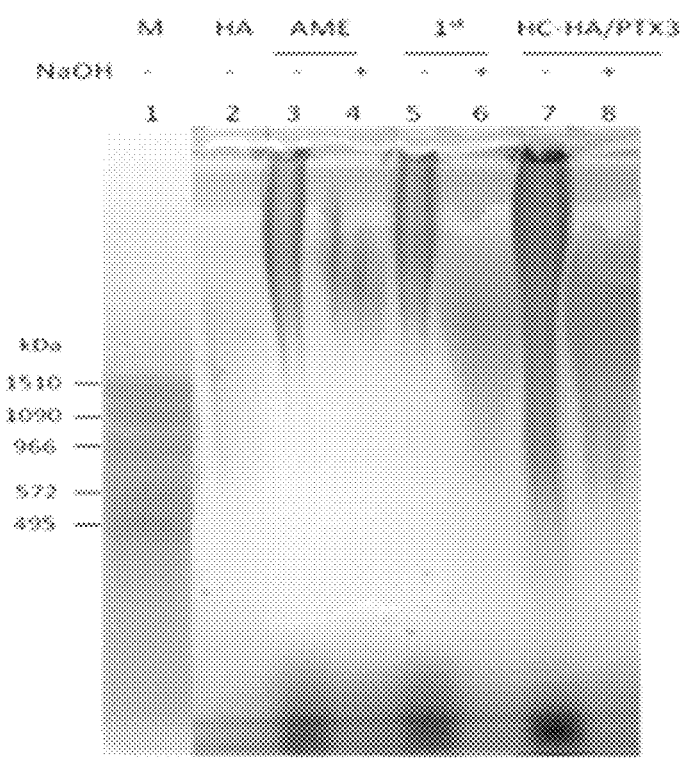
Figure 2C:
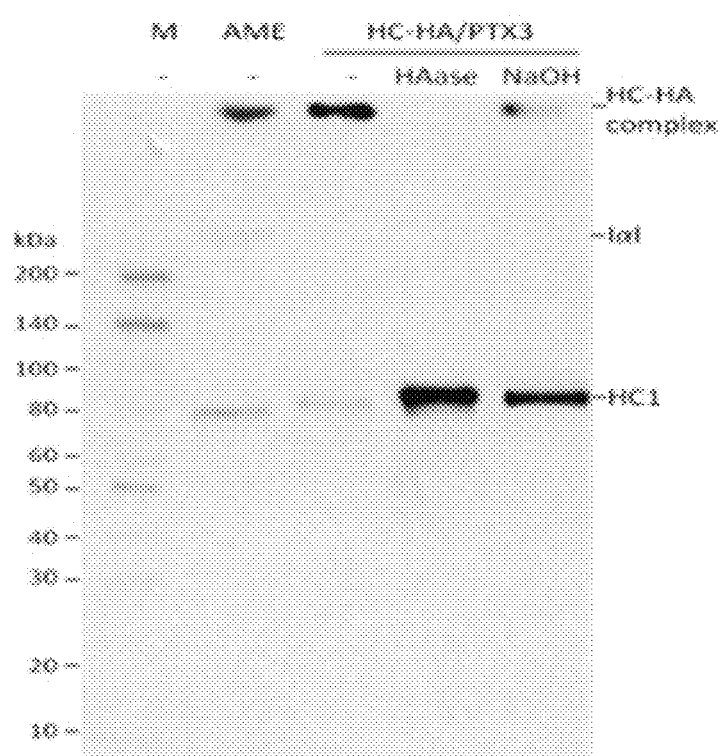
Figure 2D:
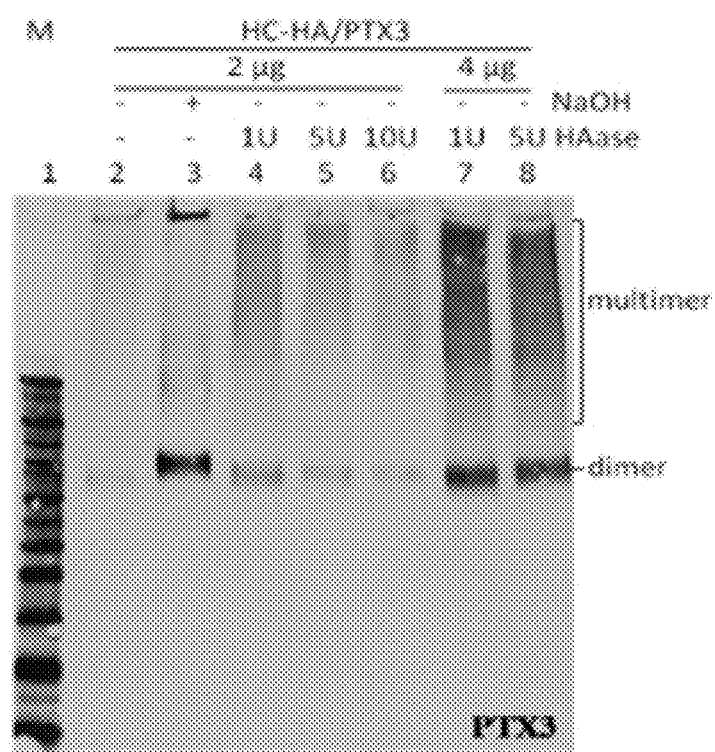

Example 5: HC-HA/PTX3 is a Unique Matrix Component Responsible for AM's Therapeutic Actions HC-HA/PTX3 complex, first found in the cumulus-oocyte complex surrounding the ovulated oocyte, plays a critical role in fertilization. HC-HA/PTX3 is abundantly present in human AM and this discovery has led to several exciting findings: (1) AM epithelial and stromal cells express all components (HA, HC1, HC2, bikunin, TSG-6, and PTX3) necessary for HC-HA/PTX3 biosynthesis (FIG. 2A); (2) HC-HA/PTX3 purified from AM extract (AME) consists of HMW HA (>3000 kDa) with covalently linked HC1 of IαI and tightly bound PTX3 (FIG. 2B-2D), but not HC2, bikunin, or TSG-6 and (3) HC-HA/PTX3 is responsible for AM's therapeutic actions which is briefly summarized below.

To make sure HC-HA/PTX3 prepared from each lot of AM donors was consistent biochemically and functionally, a manufacturing process using optimized SOPs under GMP facility was established. Although the yield of HC-HA/PTX3 from different AM donors varied, no significant differences in the potency assays were observed, which were developed based on inhibition of tartrate resistant acid phosphatase activity in osteoclasts and on promotion of macrophage M2 polarization in IFN-γ/LPS-stimulated macrophages. Consequently, the reference material to validate the release of each lot of HC-HA/PTX3 to be used in in vitro and in vivo studies was established.

Inflammation involving neutrophils and macrophages plays an important role in PVR development. Injection of macrophages into the rabbit vitreous induced epiretinal membranes, posterior vitreous separation, and retinal detachment. Macrophages can transdifferentiate into fibroblast-like cells and secrete growth factors (e.g., PDGF), which contribute to proliferation and EMT of RPE cells, the two key events in PVR pathogenesis. Soluble HC-HA/PTX3, but not HA, significantly promoted apoptosis of activated (by fMLP or LPS) but not resting neutrophils. Similarly, soluble HC-HA/PTX3, but not HA, dose-dependently promoted apoptosis of activated (by IFN-γ, LPS or IFN-γ/LPS) but not resting macrophages. In addition, soluble and immobilized HC-HA/PTX3, but not HA, promoted phagocytosis of apoptotic neutrophils by macrophages. Immobilized HC-HA/PTX3 promoted anti-inflammatory M2 polarization of LPS- or IFN-γ/LPS-activated macrophages. In addition, such M2 polarization was coupled with notable downregulation of IL-23, which was produced by activated macrophages and dendritic cells to activate Th17 cells. Consequently, subconjunctival injection of HC-HA/PTX3 prolonged survival of allogeneic corneal transplants in mice. These data support the notion that HC-HA/PTX3 is a novel complex which can suppress inflammation mediated by both neutrophils and macrophages.

Figure 3A:
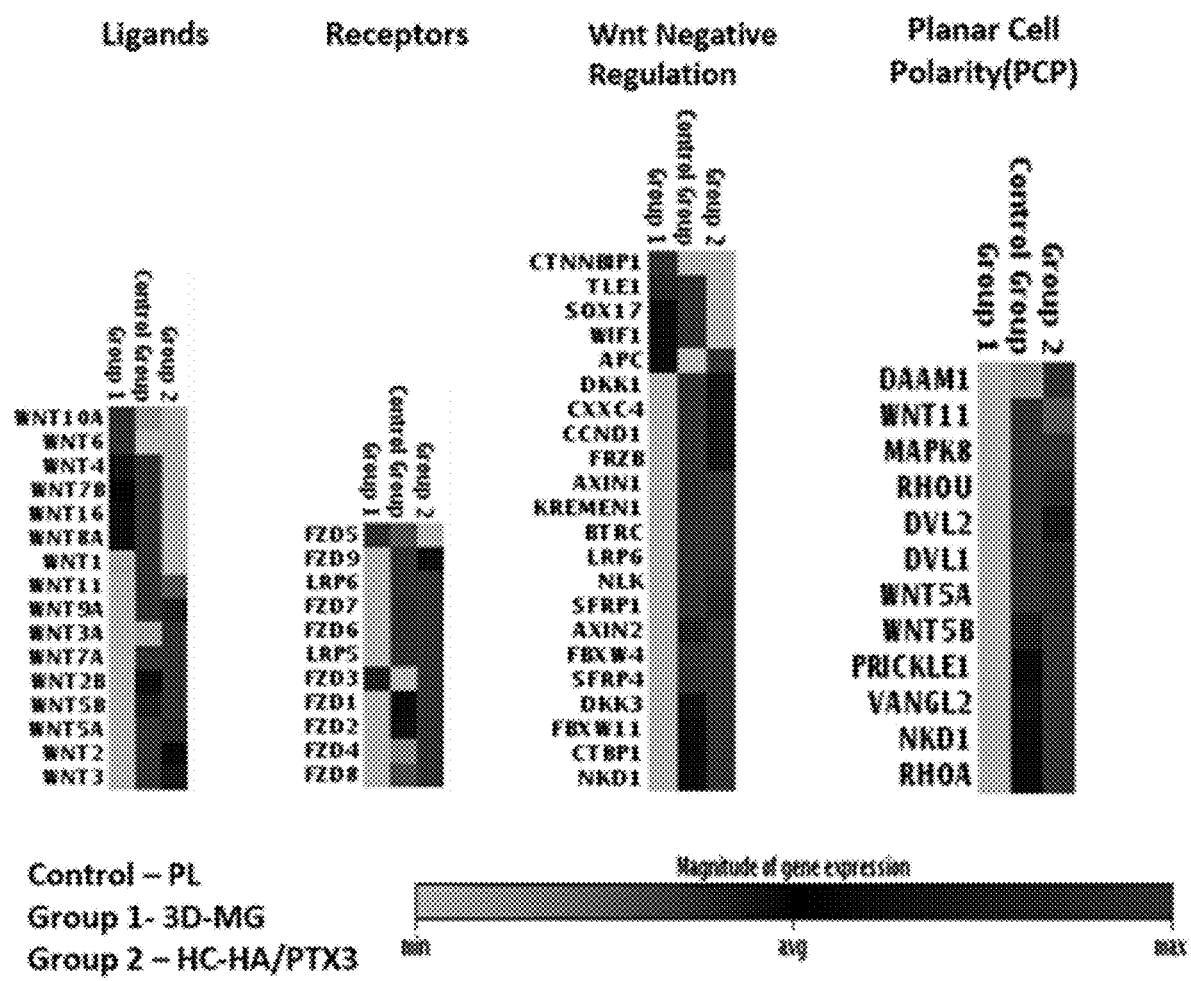
FIGS. 3A-3B illustrate canonical but not non-canonical Wnt signaling is suppressed by immobilized HC-HA/PTX3 in LEPCs/LNCs.
Figure 3B:
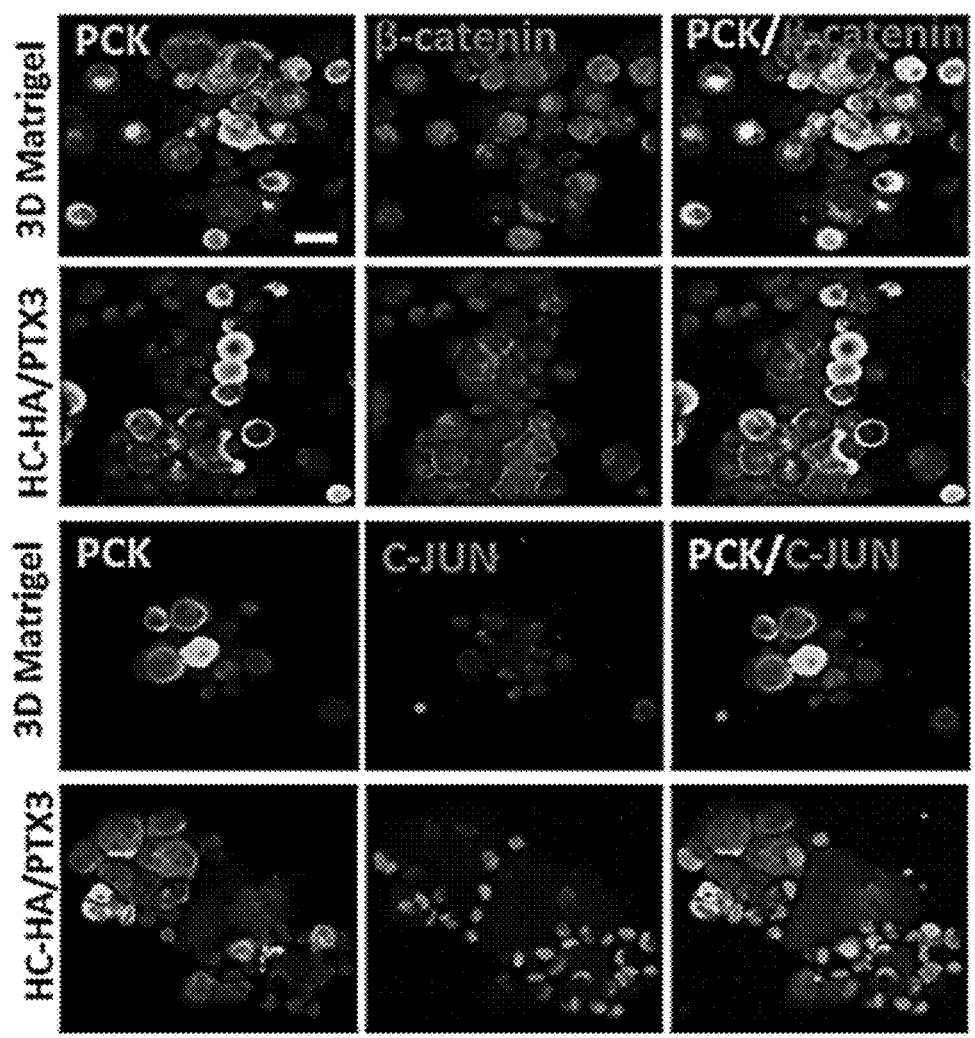

Example 6: HC-HA/PTX3 Downregulated Canonical Wnt Signaling in Human Limbal Epithelial Progenitor and Niche Cells AM inhibited squamous metaplasia of human conjunctival epithelium by downregulating the expression, phosphorylation, and nuclear translocation of β-catenin. Furthermore, HC-HA/PTX3 downregulated canonical Wnt signaling in human limbal epithelial progenitor cells (LEPCs) and niche cells (LNCs). Specifically, immobilized HC-HA/PTX3 upregulated transcript expression of non-canonical but not canonical Wnt ligands (e.g., Wnt 2B, Wnt 3A, Wnt 5A, Wnt 5B, Wnt7A), Wnt negative regulators, and planer cell polarity (PCP) factors in LEPCs/LNCs as measured by Wnt Signaling Pathway $RT^2$ Profiler PCR Array Plate (FIG. 3A). The immunostaining data further confirmed that immobilized HC-HA/PTX3 prevented the nuclear translocation of β-catenin as shown in the positive control cells seeded in 3D Matrigel. In contrast, transcript expression (FIG. 3A) and nuclear translocation (FIG. 3B) of C-JUN, a key player of non-canonical Wnt (PCP) signaling, was noted in LNCs when seeded on immobilized HC-HA/PTX3 but not 3D Matrigel (FIG. 3A). Note that activation of non-canonical Wnt (PCP) signaling is known to suppress that of canonical Wnt signaling.

Example 7: HC-HA/PTX3 Downregulates Canonical TGF-β1/Smad Signaling in Human Corneal Fibroblasts (HCF)

Figure 4A:
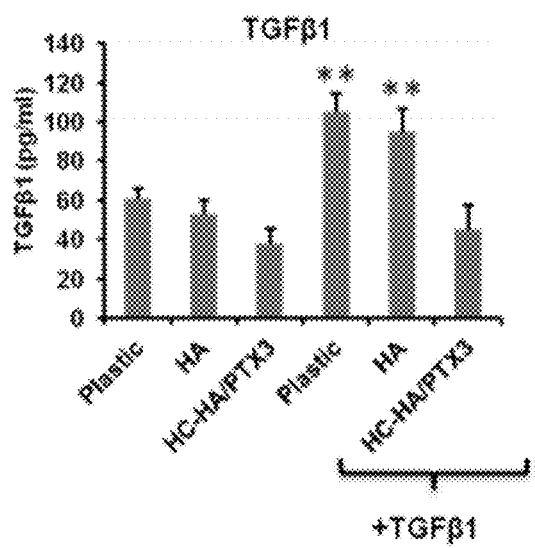
FIGS. 4A-4D illustrate expression of TGF-β and TGF-β receptors in human corneal fibroblasts (HCF).
Figure 4B:
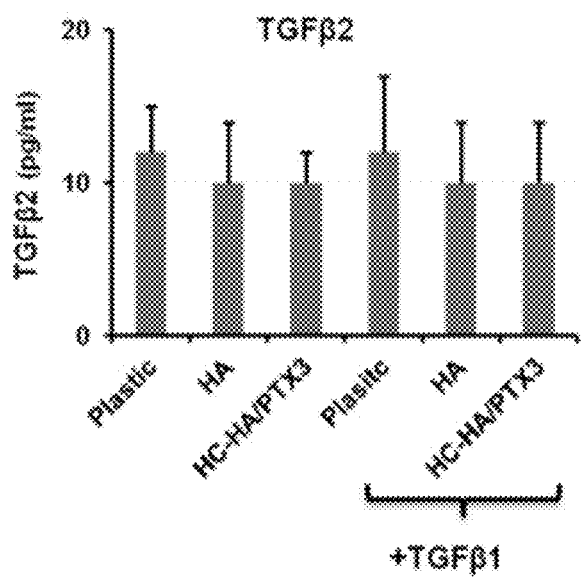
Figure 4C:
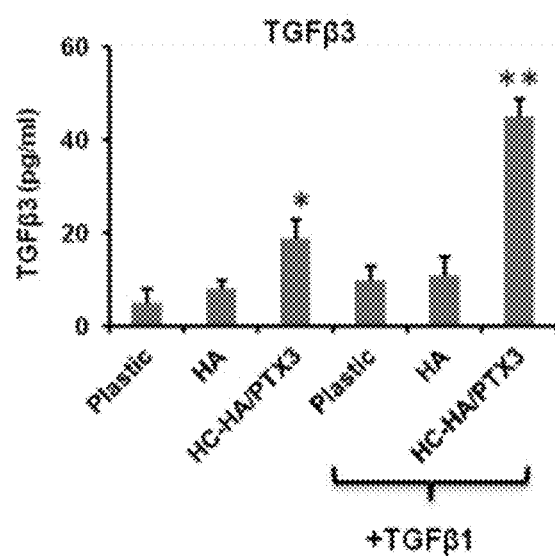
Figure 4D:
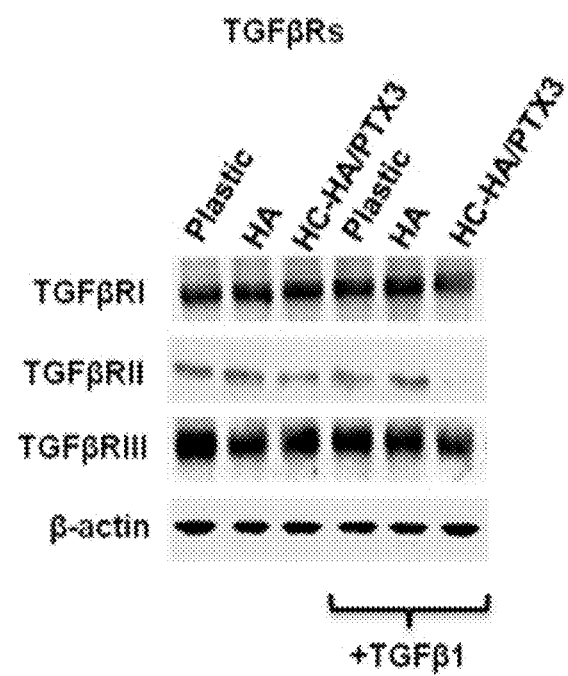
Figure 4E:
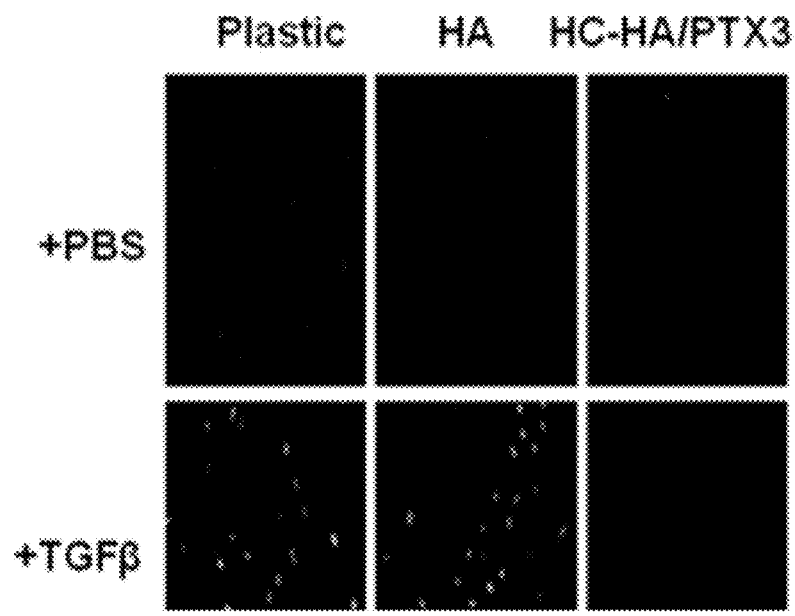
FIG. 4E exemplifies nuclear translocation of pSmad2/3 cause by addition of exogenous TGF-β1.
Figure 4F:
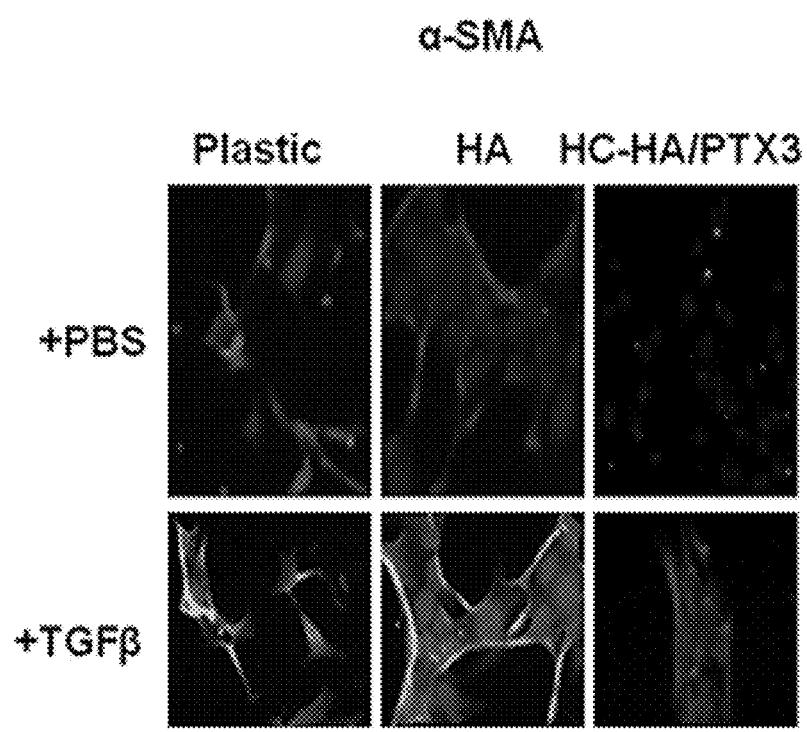
FIG. 4F exemplifies positive cytoplasmic expression of α-SMA caused by addition of exogenous TGF-1.

It has been reported that expression of TGF-β1,2,3 and TGF-βRII transcripts (using Northern blot) is downregulated in HCF and human limbal and conjunctival fibroblasts cultured on the AM stroma. AME induced cell aggregation and prevents expression of α-SMA by myofibroblasts. Human and mouse keratocytes seeded on AM stroma maintained their normal phenotype without eliciting nuclear translocation of pSmad2/3 even if they were exposed to serum or TGF-β1. Soluble HC-HA/PTX3 suppressed the TGF-β1 promoter activity of HCF (FIG. 4A). It is known that exogenous TGF-β1 expectedly upregulates TGF-β1, but not TGF-β2 (FIG. 4B), in HCF seeded on both plastic and immobilized HA. However, TGF-β1 upregulation was not observed on immobilized HC-HA/PTX3. Surprisingly, TGF-β3, an anti-scarring isoform, was upregulated only by HC-HA/PTX3, with or without TGF-β1 (FIG. 4C). Expression of TGF-βRII was reduced to nearly nil on HC-HA/PTX3 after TGF-β1 challenge (FIG. 4D). As expected, exogenous TGF-β1 caused the nuclear translocation of pSmad2/3 (FIG. 4E) and positive cytoplasmic expression of α-SMA (FIG. 4F) in HCF on plastic and HA. However, HC-HA/PTX3 effectively blocked these TGF-β1-induced changes in HCF. Collectively, HC-HA/PTX3 downregulated canonical TGF-β1 signaling and prevented myofibroblast differentiation triggered by exogenous TGF-β1 in HCF.

Example 8: Preparation of Preserved Human Fetal Support Tissue

Human placenta was collected at elective cesarean delivery. The placenta was flattened onto nitrocellulose paper (Hybond N+, Amersham, England), with the epithelium surface up. The fetal support tissue samples were stored at −80° C. in DMEM/glycerol 1:2 (v/v) until use.

Example 9: Amniotic Membrane Extract Preparations

Fresh and frozen human placentas were obtained from Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1×PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

Total AM extracts were divided into two 50 ml conical centrifuge tubes. One was centrifuged at high speed (HS, 48,000×g) and the other one was centrifuged at a low speed (LS, 15,000×g) at 4° C. Aliquots of the HS and LS supernatant were transferred to sterile 1.5 ml Eppendorf tubes and were designated as AM/HS and AM/LS, respectively. Desired AM/HS samples were frozen at −20° C. for 1 h before lyophilization. The samples were then placed in the chamber of FreeZone (Labconco, Kansas City, Mo.) with holes on the cap. Samples were lyophilized at −50° C. at a vacuum of 0.85 mBar for 5 hours. Before use, the samples were reconstituted with the sterile distilled $H_2O$ to the same volume. The same method was also used to prepare extracts from AM jelly, which was easily scraped from the adherent material on the AM stroma.

Example 10: Total Soluble Human Amniotic Membrane and Amniotic Membrane Jelly Extract Preparations Frozen human placenta material was obtained from Bio-Tissue, Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1×PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

The total water-soluble extract was mixed for 1 hr at 4° C., subsequently fractionated by two different speeds of centrifugation at 4° C. for 30 min, i.e., 15000×g and 48000×g, and the resultant supernatant was designated as L and H, respectively. Each supernatant was divided into aliquots and stored at −80° C. This method was also used to prepare extracts from AM jelly, which was easily scraped from the adherent material on the AM stroma.

Example 11: Total Soluble Human Amniotic Membrane and Amniotic Membrane Jelly Extracts by Different Buffers and Fractionation Methods In examining preparations in different extraction buffers, the powder as prepared from above was weighed and mixed with Buffer A (Isotonic Low salt): 100 mM Tris-HCl, pH 7.6, 150 mM NaCl, 4 mM EDTA, 1% Triton X-100 at the wet weight (g) of AM to the buffer (ml) at 1:1 ratio by stirring at 4° C. for 1 hr. After centrifugation at 48000×g, the resultant pellet was subsequently extracted by Buffer B (high salt): 100 mM Tris-HCl, pH 7.6, 1 M NaCl, 4 mM EDTA, 1% Triton X-100 by stirring at 4 C for 1 hr. Again after centrifugation at 48000×g, the pellet was finally extracted by Buffer C (4 M guanidine hydrochloride): 100 mM sodium acetate, pH 5.8, 4 M guanidine hydrochloride, 4 mM EDTA, 1% Triton X-100 by stirring at 4° C. for 24 hr. All the above three buffers were supplemented with the following protease and phosphatase inhibitors: 1 µg/ml aprotinin, 1 µg/ml leupeptins, 1 µg/ml pepstatin A, 0.5 mM PMSF, 50 µM sodium fluoride and 0.2 µM sodium vanadate. The resultant supernatants, designated as Extract A, B, and C, respectively, were dialyzed against the dialysis buffer (50 mM Tris-HCl, pH 7.5, 0.15 M NaCl) supplemented with 0.5 mM PMSF at 4° C. for 6 hr and dialysis buffer was changed twice, each with 500× (the volume ratio of dialysis buffer: samples). After dialysis, the volume of each sample was measured and adjusted to the same volume with the dialysis buffer. The same method was also used to prepare extracts from AM jelly, which was the adherent material on the AM stroma that could be easily scraped off.

Example 12: Preparation of Total Soluble Human Amniotic Membrane Extracts in PBS The entire procedure for preparation of total soluble human AM extracts (T) was carried out aseptically so as to be used for subsequent cell culture-based experiments. Frozen human placenta was obtained from Bio-Tissue, Inc. (Miami, Fla.), from which AM was retrieved. AM was sliced into small pieces to fit into the barrel of a BioPulverizer (Biospec Products, Inc., Bartlesville, Okla.), frozen in the liquid nitrogen, and then pulverized into a fine powder. The powder was weighed and mixed with cold PBS buffer (prepared by adding distilled $H_2O$ to 1×PBS, pH7.4, from 10×PBS, cat #70011-044, Invitrogen, Carlsbad, Calif.) with protease inhibitors (protease inhibitor cocktail, P8340, Sigma, and supplemented with 1 mM PMSF) and phosphatase inhibitors (50 mM sodium fluoride and 0.2 mM sodium vanadate) at 1:1 (ml/g). The mixture was kept on ice and homogenized with a Tissue Tearor (Biospec Products, Inc., Dremel, Wis.) for 5 times, 1 min each with a 2 min interval cooling. This water-soluble extract was designated as "Total" (T). The total water-soluble extract was mixed for 1 hr at 4° C., centrifuged at 4° C. for 30 min at 48000×g. The supernatant was divided into aliquots and stored at −80° C.

Example 13: Preparation of Water-Soluble AM Stromal Extracts

Using aseptic techniques, frozen human AM obtained from Bio-Tissue, Inc. (Miami, Fla.) was briefly washed 2-3 times with HBSS to remove the original storage medium. The AM stroma was scraped by spatula, frozen in the air phase of liquid nitrogen and grounded to fine particles by BioPulverizer (Biospec Products, Inc., Bartlesville, Okla.) followed by homogenization on ice with Tissue Tearor (Biospec Products, Inc., Dremel, Wis.) in PBS, pH 7.4, for 1 min. The homogenate was mixed by rotation for 1 h and centrifuged at 14,000×g for 30 min at 4° C. The supernatant in PBS was then collected, and stored in aliquots at −80° C. The protein concentration was determined by BCA assay. This water-soluble protein extract, designated as amniotic stromal extract (ASE), was used for experiments described herein.

Example 14: AM Stromal Extract Preparation

The complete procedure for preparation of protein extracts was carried out aseptically. Frozen human AM obtained from Bio-Tissue (Miami, Fla.) was briefly washed 2-3 times with HBSS (Invitrogen, Carlsbad, Calif.) to remove the storage medium. AM stroma was scraped from the stromal side of the AM by spatula for AM stroma extract preparation. Human placenta as well as chorion obtained from Baptist Hospital (Miami, Fla.) was rinsed 3 times with HBSS to remove blood. To prepare the water-soluble protein extract, total AM, scraped AM stroma, stroma-removed AM, placenta, and chorion were each frozen in the air phase of liquid nitrogen and each ground to fine particles using a BioPulverizer (Biospec Products, Inc., Bartlesville, Okla.) followed by homogenization on ice with Tissue Tearor (Biospec Products, Inc., Dremel, Wis.) in PBS (pH 7.4) for 1 min. Each homogenate was mixed for 1 h and centrifuged at 14,000 g for 30 min at 4° C. Each supernatant (in PBS) was then collected and stored in aliquots (0.5 ml) at −80° C. The BCA assay (Pierce, Rockford, Ill.) was used to quantitate the total protein in different extracts.

Example 15: Preparing Water-Soluble and Lyophilized Powder Forms of Human AM Extracts To prepare human AM extracts, the entire procedure was carried out aseptically. Unless otherwise noted, the AM extracts were handled at room temperature during the steps of the procedure. First, fresh or frozen human AM was obtained, preferably from Bio-Tissue, Inc. (Miami, Fla.). Frozen AM was briefly washed 2-3 times with HBSS (Invitrogen, Carlsbad, Calif.) to remove the storage medium. Fresh human placenta or chorion was rinsed 3 times with HBSS to remove blood.

To prepare the water-soluble form of AM extracts, the AM (e.g., AM stroma, stroma-removed AM, placenta, chorion) was transferred to a sterile 50 ml centrifuge tube and centrifuged at 4° C. for 5 min at 5000×g to remove the excess fluid. The AM was weighed, transferred to a 100 mm or 150 mm sterile Petri dish, and frozen in the air phase of a liquid nitrogen container for 20 min to facilitate the subsequent homogenization. The frozen AM was then sliced into small pieces with a disposable scalpel or ground to fine particles using a BioPulverizer (Biospec Products, Inc., Bartlesville, Okla.) or other suitable device, and homogenized with Tissue Tearor (Biospec Products, Inc., Dremel, Wis.), or other suitable device, in phosphate buffered saline (PBS) or DMEM without phenol red (Invitrogen, Carlsbad, Calif.) at neutral pH. For biochemical characterization and purification, the above solutions were supplemented with the following proteinase inhibitors: 1 µg/ml aprotinin, 1 µg/ml leupeptin, 1 µg/ml pepstatin A, and 1 mM PMSF. However, if the extract was to be directly added to cell culture, no protease inhibitors were added. The homogenate was mixed at 4° C. for 30 min and centrifuged at 15,000×g for 30 min. The supernatant (i.e., AM extract) was collected and stored in aliquots (0.5 ml) at −80° C. The BCA assay (Pierce, Rockford, Ill.) was used to quantitate the total protein in each AM extract.

To prepare the lyophilized powder form of AM extracts, frozen AM was ground to fine particles using a BioPulverizer (Biospec Products, Inc., Bartlesville, Okla.), or other suitable device, and further homogenized as described herein. Aliquots of approximately 0.5 ml were lyophilized by SpeedVac (Savant Instruments Inc., Farmingdale, N.Y.) at 4° C. for 4 h to decrease the weight from 280 mg to 32 mg (about 89% reduction). The lyophilized powder was weighed and stored at −80° C. Before use, the lyophilized powder was reconstituted in a suitable buffer.

To prepare AM stromal extracts, the AM stroma was scraped from the stromal surface of intact total AM leaving the basement membrane and the amniotic epithelium intact, and the frozen AM stroma was ground using a BioPulverizer as described herein. The stroma was extracted with PBS at a neutral pH at 4° C. for 30 min and centrifuged at 15,000×g for 30 min. The supernatant was collected and stored in aliquots (0.5 ml) at −80° C. The BCA assay (Pierce, Rockford, Ill.) was used to quantitate the total protein in the AM stromal extract.

Example 16: Suppression of TGF-β1 Promoter Activity

Figure 8:
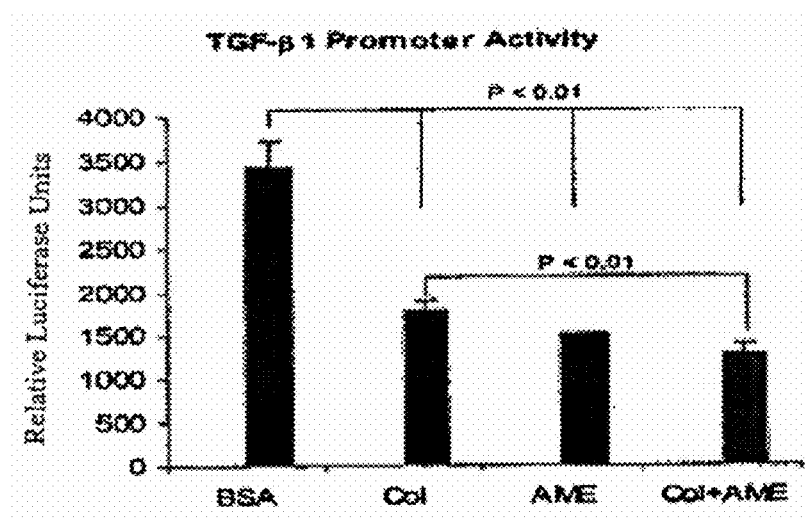
FIG. 8 illustrates the effect of the addition of collagen gel (Col), AM extract AME, or collagen gel mixed with AM extract (Col+AME) on the suppression of TGF-β promoter activity. BSA was used as a control.
Figure 9:
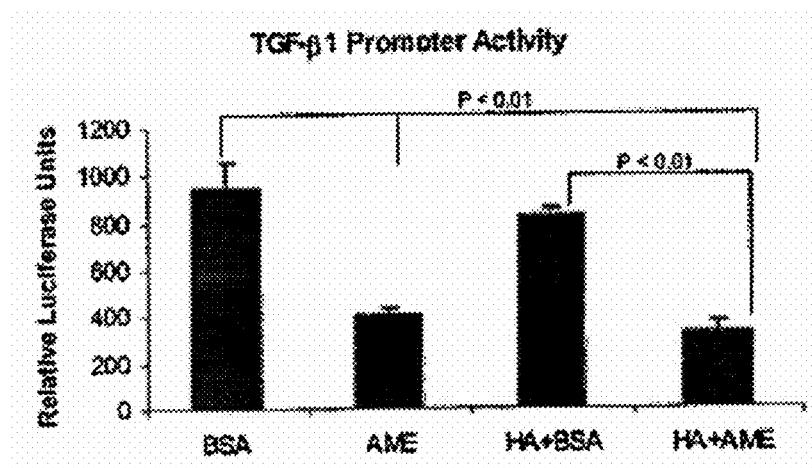
FIG. 9 illustrates the effect of treatment with AME, HA, or HA+AME, compared to a control assay with BSA alone, on the suppression of TGF-β activity. The promoter activity is displayed as relative luciferase units (RLU).

The fetal support preparations and compositions described herein suppress of TGF-β1 promoter activity as shown herein; thus the fetal support preparations and compositions described herein can be used for anti-scarring, anti-inflammatory, and anti-angiogenic therapies. The fetal portion of the frozen amniotic membrane has a significantly higher anti-scarring effect than that of fresh amniotic membrane; the placental portion of the frozen amniotic membrane also has a significantly higher anti-scarring effect than the fresh amniotic membrane. Therefore, the frozen fetal support tissue, either the placental or fetal portion, showed more potent suppressive effects in TGF-β than the fresh fetal support tissue. This suppressive effect mediated by total fetal support tissue extract obtained from frozen fetal support tissue was dose-dependent over a range of 0.4 to 125 µg/ml (FIG. 8). Furthermore, such a suppressive effect could not be substituted by high MW HA alone (exceeding 100× of equivalent AM extract), and was lost after digestion with hyaluronidase (FIG. 9), suggesting that it was mediated by a complex between HA-IαI. Centrifugation at low or high speed did not affect the suppressive effect significantly. However, subsequent lyophilization and reconstitution produced a more potent suppressive effect. Additionally, the overall suppressive effect of AM was more potent than that of AM jelly.

Example 17: Fetal Support Tissue Preparations and Purified Compositions Used to Culture Cells To examine the effect of fetal support tissue on the cell differentiation process, myofibroblasts differentiated from AMSCs at passage 2 were subcultured onto the stromal matrix of AM, and compared to those subcultured on collagen I-coated dish as a control. After 7 days of cultivation in DMEM with 10% FBS, AMSCs on collagen I still maintained a myofibroblastic shape. In contrast, cells seeded on fetal support tissue stromal matrix exhibited a mixture of round, spindle, elongated, and dendritic shapes. Thus, in some embodiments, fetal support tissue preparations have dedifferentiation abilities, and are used to slow cell differentiation.

Example 18: Effect of HC-HA/PTX3 on Cell Migration and Collagen Gel Contraction

Cell Culture and Treatment

ARPE-19, a human diploid RPE cell line, was cultured in HEPES-buffered DMEM and Ham's F-12 (1:1) supplemented with 10% FBS, 50 units/ml penicillin, and 50 µg/ml streptomycin at 37° C. in humidified air with 5% $CO_2$. For post-confluence experiments, cells were continuously cultured for 7 days upon 100% confluence before being tested. For low cell density assays, cells were seeded at $1 \times 10^4/cm^2$ or other densities overnight (20-24 h) followed by treatment with growth factors and cytokines for 24-120 h or 48 h (after optimization). In the case of serum starvation, cells were incubated in serum-free (SF) medium for 24 h followed by treatment with growth factors and cytokines for 24-120 h. BrdU (10 µM) labeling was performed for 4 h prior to the termination of the growth factors/cytokines treatment.

Purification of HC-HA/PTX3 from Human AM

HC-HA/PTX3 was prepared from cryopreserved human placentas provided by Bio-Tissue, Inc. (Miami, Fla.). AM from the same donor was extracted by PBS (pH 7.4) to generate the PBS extract as reported. The extract was then fractionated by ultracentrifugation in a CsCl gradient at an initial density of 1.35 g/ml in 4 M GnHCl at 35,000 rpm for 48 h at 15° C. (LM8 model, SW41 rotor, Beckman Coulter, Indianapolis, Ind.). A total of 12 fractions (1 ml/fraction) was collected from each ultracentrifuge tube. The weight of each fraction was measured to calculate the density. After the biochemical analysis (HA ELISA, BCA protein assay, and Western blot, see below), fractions containing HA but little or no proteins were pooled and subjected to the second run of ultracentrifugation in a CsCl gradient at an initial density of 1.40 g/ml. Selective fractions (containing HA but undetectable proteins measured by BCA assay and designated as HC-HA/PTX3) were pooled and dialyzed against distilled water, lyophilized, and stored at −80° C. Therefore, the amount of HC-HA/PTX3 was expressed based on the HA amount present in the complex.

Cell Migration

The migration assay was performed in 24-well transwell plate (8 µm pore size, Costar, Kennebunk, Me.) when 0.5 ml DMEM/F12 (1:1) without or with EGF (10 ng/ml), FGF-2 (20 ng/ml), and TGF-β1 (10 ng/ml) was added in the lower compartment while 0.1 ml of ARPE-19 cell re-suspended in DMEM/F12 ($2 \times 10^6$/ml) treated with PBS (vehicle control), HA (25 µg/ml), or HC-HA/PTX3 (25 µg/ml) was added to the upper compartment. After incubation at 37° C. for 4 h, cells not migrating through the pores were removed by a cotton swab, while cells on the filter facing the lower compartment were fixed with 5% glutaraldehyde, stained with 1% crystal violet, and counted from six random microscopic fields for each control or treatment group.

Collagen Gel Contraction 0.25 ml of collagen type I solution (Corning, Bedford, Mass.) in cold DMEM/F12 (2.5 mg/ml) was added to each well of 24-well plates, followed by incubation at 37° C. for 1 h before adding 0.5 ml of ARPE-19 cells or primary human RPE cells (each at $5 \times 10^5$/ml) without or with TGF-β1 (10 ng/ml) and treatment of PBS (vehicle control), HA (25 µg/ml), or HC-HA/PTX3 (25 µg/ml) on the top of collagen gel. After 24 h, the gels were freed from the walls of the culture wells with a small spatula. The photographic images of collagen gels were digitalized and the area was measured with NIH ImageJ 1.45 software. The percentage of gel contraction was determined by measuring the gel size at 72 h when compared to the initial size (at 0 h) and compared among groups.

Results

Figure 21:
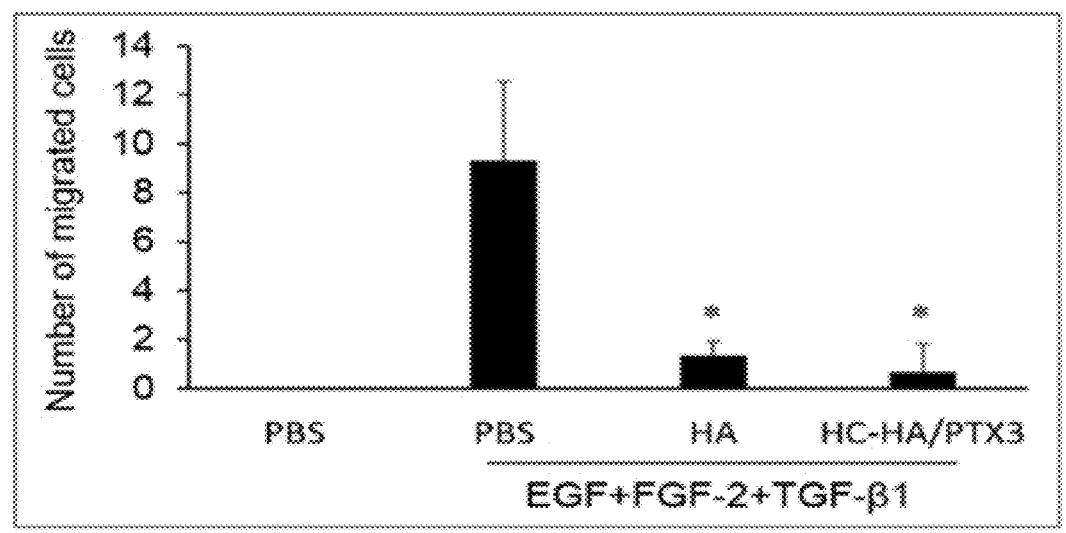
FIG. 21 illustrates the number of migrated cells counted from six random microscopic fields (n=4, * indicates p<0.05 when compared with PBS+EGF+FGF-2+TGF-β1).
Figure 22:
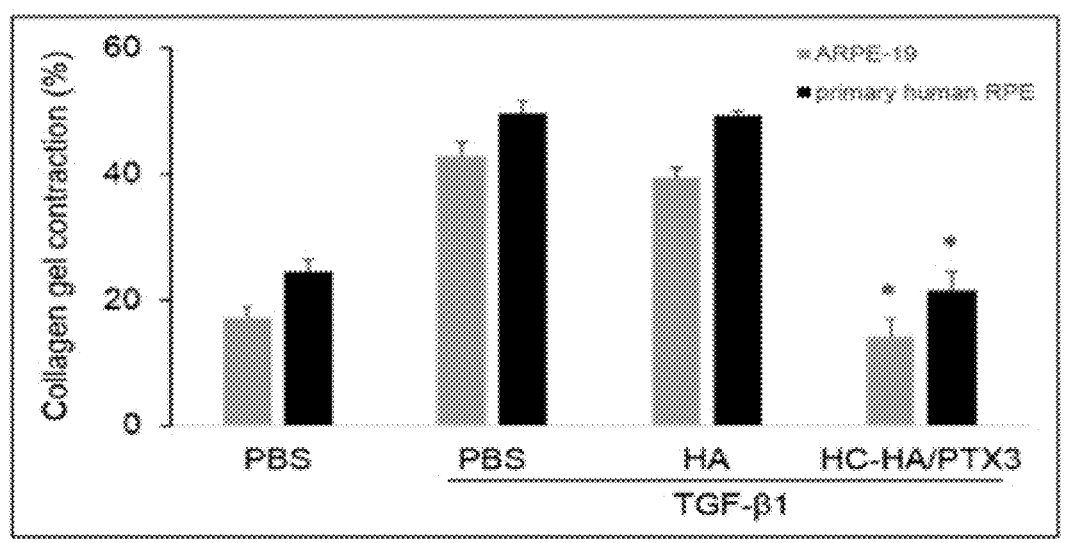
FIG. 22 illustrates the percentage of gel contraction compared among groups (n=4, * indicates p<0.05 compared with PBS+TGF-β1).

HC-HA/PTX3 (25 µg/ml) as well as HA (25 µg/ml) completely suppressed migration of ARPE-19 cells under the stimulation of EGF (10 ng/ml), FGF-2 (20 ng/ml), and TGF-β1 (10 ng/ml) (FIG. 21). In contrast, HC-HA/PTX3, but not HA, significantly reduced the TGF-β1-induced collagen gel contraction in both ARPE-19 cells and primary human RPE cells (FIG. 22).

While preferred embodiments have been shown and described herein, it will be obvious to those skilled in the art that such embodiments are provided by way of example only. Numerous variations, changes, and substitutions may now occur. It should be understood that various alternatives to the embodiments described herein can be employed in practicing the described methods. It is intended that the following claims define the scope of the embodiments and that methods and structures within the scope of these claims and their equivalents be covered thereby.

What is claimed is:

1. A method for preventing or reducing proliferation, cell migration, or epithelial-mesenchymal transition (EMT) of epithelial cells in an individual who has experienced retinal detachment, comprising: administering to the individual who has experienced retinal detachment a therapeutically effective amount of a composition, comprising:

(a) a preparation of fetal support tissue, wherein the preparation of fetal support tissue comprises heavy chain-hyaluronic acid/pentraxin 3 complex (HC-HA/PTX3); and (b) a pharmaceutically acceptable diluent, excipient, vehicle, or carrier, thereby preventing or reducing the proliferation, cell migration, or EMT of epithelial cells.

2. The method according to claim 1, wherein the fetal support tissue is placenta, placental amniotic membrane, umbilical cord, umbilical cord amniotic membrane, chorion, amnion-chorion, amniotic stroma, amniotic jelly, amniotic fluid, or a combination thereof.

3. The method of claim 1, wherein the fetal support tissue is frozen or previously frozen.

4. The method according to claim 1, wherein the epithelial cells are retinal pigment epithelial cells (RPE), conjunctival epithelial cells, corneal epithelial cells, limbal epithelial cells, retinal cells, or renal epithelial cells.

5. The method according to claim 1, wherein the epithelial cells are human epithelial cells.

6. The method of claim 1, wherein the preparation of fetal support tissue is an extract of fetal support tissue, micronized fetal support tissue, a homogenate, a powder, morselized fetal support tissue, pulverized fetal support tissue, ground fetal support tissue, purified heavy chain-hyaluronic acid/pentraxin 3 complex (HC-HA/PTX3), or a combination thereof.

7. The method according to claim 1, wherein the composition is a gel, a solution, or a suspension.

8. The method according to claim 1, wherein the composition is for local administration.

9. The method according to claim 1, wherein the composition is formulated for intraocular injection, subretinal injection, intravitreal injection, periocular injection, subconjunctival injection, retrobulbar injection, intracameral injection or sub-Tenon's injection.

* * * * *

UNITED STATES PATENT AND TRADEMARK OFFICE
CERTIFICATE OF CORRECTION

| | | |
|---|---|---|
| PATENT NO. | : 11,318,169 B2 | Page 1 of 1 |
| APPLICATION NO. | : 16/421191 | |
| DATED | : May 3, 2022 | |
| INVENTOR(S) | : Tseng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 27 days.

Signed and Sealed this
Tenth Day of June, 2025

Coke Morgan Stewart
*Acting Director of the United States Patent and Trademark Office*